(12) United States Patent
Borja et al.

(10) Patent No.: US 9,085,776 B2
(45) Date of Patent: Jul. 21, 2015

(54) METHOD FOR ENHANCING DROUGHT TOLERANCE IN PLANTS

(71) Applicants: Marisé Borja, Madrid (ES); Julio Bonet-Gigante, Madrid (ES); Antonio Molina, Madrid (ES); Rafael Catalá, Madrid (ES); Julio Salinas, Madrid (ES)

(72) Inventors: Marisé Borja, Madrid (ES); Julio Bonet-Gigante, Madrid (ES); Antonio Molina, Madrid (ES); Rafael Catalá, Madrid (ES); Julio Salinas, Madrid (ES)

(73) Assignees: Plant Response Biotech S.L., Madrid (ES); Consejo Superior De Investigaciones Cientificas, Madrid (ES)

( * ) Notice: Subject to any disclaimer, the term of this patent is extended or adjusted under 35 U.S.C. 154(b) by 0 days.

(21) Appl. No.: 14/142,285

(22) Filed: Dec. 27, 2013

(65) Prior Publication Data
US 2015/0052632 A1    Feb. 19, 2015

Related U.S. Application Data

(60) Provisional application No. 61/865,549, filed on Aug. 13, 2013.

(51) Int. Cl.
C12N 15/63     (2006.01)
C12N 15/82     (2006.01)
C07K 14/415    (2006.01)

(52) U.S. Cl.
CPC ..... *C12N 15/8273* (2013.01); *C12Y 114/13008* (2013.01)

(58) Field of Classification Search
None
See application file for complete search history.

(56) References Cited

U.S. PATENT DOCUMENTS

| | | | |
|---|---|---|---|
| 6,455,468 B1 | 9/2002 | Hsiang | |
| 2007/0124833 A1* | 5/2007 | Abad et al. | 800/278 |
| 2010/0011462 A1* | 1/2010 | Kliebenstein et al. | 800/278 |
| 2010/0205690 A1* | 8/2010 | Blasing et al. | 800/278 |
| 2013/0130902 A1 | 5/2013 | Roose | |
| 2013/0333068 A1* | 12/2013 | Coffin | 800/275 |

FOREIGN PATENT DOCUMENTS

| | | |
|---|---|---|
| ES | 2347399 A1 | 10/2010 |
| WO | 95/35022 A1 | 12/1995 |

(Continued)

OTHER PUBLICATIONS

GenBank Accession No. XM_001157345. Zea mays disulfide oxidoreductase/monooxygenase. Published Apr. 17, 2013. pp. 1-3.*

(Continued)

*Primary Examiner* — Cathy Kingdon Worley
*Assistant Examiner* — Ashley K Buran
(74) *Attorney, Agent, or Firm* — Bethany Reid Roahrig; Barbara Campbell; Cochran Freund & Young, LLC

(57) ABSTRACT

A method for increasing drought tolerance in a plant or photosynthetic organism is disclosed, where the tolerance is increased by introducing nucleic acid sequences coding for polypeptides with monooxigenase activity or by the modification of endogenous nucleic acid sequences that increase the endogenous TMAO content in plants as well as to nucleic acid constructs, recombinant vectors, cells, transgenic plants, crops, propagation material, compositions and harvestable parts of a plant comprising nucleic acid sequences in order to increase water stress tolerance and so on.

12 Claims, 4 Drawing Sheets

Photos of wild type Col-0 *Arabidopsis thaliana* plants, transgenic *Arabidopsis thaliana* plants over expressing FMO proteins and *Arabidopsis thaliana* plants overexpressing FMO proteins after drought recovery

FMO X8

FMO X3

Col-0

(56) References Cited

FOREIGN PATENT DOCUMENTS

| WO | 96/41532 A1 | 12/1996 |
|---|---|---|
| WO | 97/08951 A1 | 3/1997 |
| WO | WO2008023263 | 2/2008 |
| WO | 2008/060555 A2 | 5/2008 |
| WO | WO2010034862 | 4/2010 |
| WO | 2015/022365 A1 | 2/2015 |

OTHER PUBLICATIONS

Yancey, P.H., J. Exp. Biol., (2005), 208(15): 2819-30.
Li, J. et al., Plant Physiol., (2008), 148 (3):1721-33.
Schlaich, N. L., Trends Plant Sci., (2007), 12 (9): 412-8.
Hibino, T. et al., J. Biol. Chem., (2002), 277 (44): 41352-60.
Schlenk, D. et al., Biochem. Pharmacol., (1996), 52 (5): 815-8.
Lang, D. H. et al., Biochem. Pharmacol., (1998), 56 (8): 1005-12.
Larsen, B.K. et al., J. Comp. Physiol. B., (2001), 171 (50): 421-29.
Doan-Nguyen, V. et al., Protein Sci., (2007), 16(1): 20-9.
Lawton, M. P. et al Arch. Biochem. and Biophysics., (1994) 308 (1) 254-257.
Cushman, J.C., Amer. Zool., (2001), 41(4): 758-69.
O'Donnell et al., Plant Physiology and Biochemistry., (2013) 73: 83-92.
Fan et al., Trees. (1997) 11: 342-348.
Mondal et al., J. Phys. Chem. B. (2013) 117: 8723-8732.
Yang et al. Journal of Experimental Botany,(2010) 61, No. 12, pp. 3245-3258.
Kim, J. I., et al., Overexpression of Arabidopsis YUCCA6 in Potato Results in High-Auxin Developmental phenotypes and enhanced resistance to water deficit, Sep. 17, 2012, pp. 337-349, vol. 6(2).
Charrier, A. et al., The effect of carnitine on Arabidopsis development and recovery in salt stress conditions, Planta, Aug. 19, 2011, pp. 123-135, vol. 235(1).
Lee, M. et al., Activation of a flavin monooxygenase gene YUCCA7 enhances drought resistance in Arabidopsis, Nov. 23, 2011, pp. 923-938, vol. 235(5).

* cited by examiner

Photos of wild type Col-0 Arabidopsis thaliana plants, transgenic Arabidopsis thaliana plants over expressing FMO proteins and Arabidopsis thaliana plants overexpressing FMO proteins after drought recovery Figure 2a is a map of a DNA construct that may be used to obtain the *Arabidopsis thaliana* plants for constitutive overexpression FMO proteins Figure 2b is a second map of a DNA construct that may be used to obtain the *Arabidopsis thaliana* plants for stress induced overexpression of FMO proteins

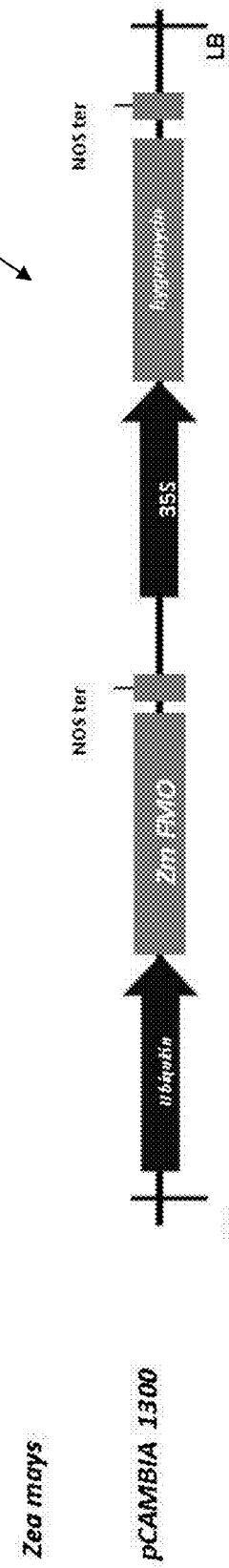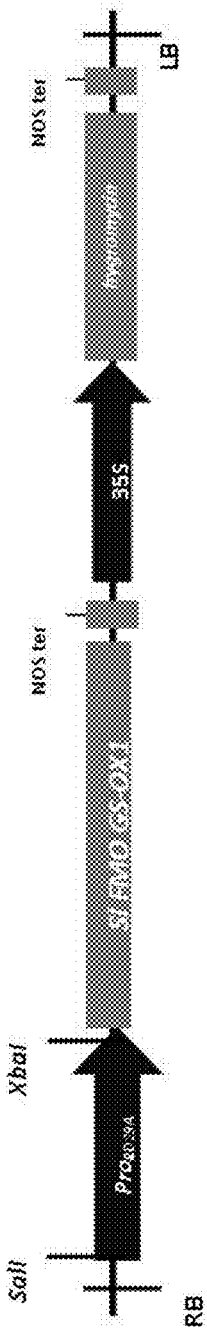

METHOD FOR ENHANCING DROUGHT TOLERANCE IN PLANTS

CROSS REFERENCE TO RELATED APPLICATIONS

This application is a non-provisional patent application of and claims the benefit of U.S. Provisional Application No. 61/865,549, filed Aug. 13, 2013, the entire contents of which are incorporated herein by reference for all purposes.

SUBMISSION OF SEQUENCE LISTING

The Sequence Listing associated with this application is filed in electronic format via EFS-Web and is hereby incorporated by reference into the specification in its entirety.

BACKGROUND

All publications cited in this application are herein incorporated by reference.

When plants are exposed to conditions where reduced water content in the soil due to a shortage of rainfall or irrigation leads to impaired water absorption, what could be called drought stress conditions, physiological functions of cells may deteriorate and thus various disorders may arise in the plant. When subjected to such stress factors plants display a variety of mechanistic responses as protective measures, with a resultant adverse effect on growth, development, and productivity. Significant losses in quality and yield are commonly observed.

While it has been known that phytohormones and some chemical substances such as plant growth regulators have effects on plants in reducing water stress such as drought stress or excessive moisture stress (see *Journal of Plant Growth Regulation* (2010) 29: 366-374), those effects are not necessarily satisfactory in practice. For example, organic osmolytes are small solutes used by cells of numerous water-stressed organisms and tissues to maintain cell volume. Similar compounds are accumulated by some organisms in anhydrobiotic, thermal and possibly pressure stresses. These solutes are amino acids and derivatives, polyols and sugars, methylamines, methylsulfonium compounds and urea. Except for urea, they are often called "compatible solutes", a term indicating lack of perturbing effects on cellular macromolecules and implying interchangeability. However, these features may not always exist, and the practical use cannot be taken for granted since high levels might cause overstabilization of proteins and some protective properties of osmolytes are harmful in the absence of a perturbant to offset (Yancey, P. H. (2005). *J. Exp. Biol.* 208 (Pt 15): 2819-30). For example the osmolite glycinebetaine (betaine) affords osmoprotection in bacteria, plants and animals, and protects cell components against harsh conditions in vitro, however, engineering of betaine production in three diverse species lacking it, *Arabidopsis, Brassica napus*, and tobacco (*Nicotiana tabacum*), by constitutive expression of a bacterial choline oxidase gene only conferred a moderate stress tolerance in some but not all betaine-producing transgenic lines and the responses to stresses such as salinity, drought, and freezing were variable among the three species. Furthermore, a fitness cost was observed in the three species (Jun H., Hariji et al. (2000) *Plant Physiol.* 122: 747-56).

The foregoing examples of related art and limitations related therewith are intended to be illustrative and not exclusive, and they do not imply any limitations on the inventions described herein. Other limitations of the related art will become apparent to those skilled in the art upon a reading of the specification and a study of the drawings.

SUMMARY

The following embodiments and aspects thereof are described and illustrated in conjunction with systems, tools and methods, which are meant to be exemplary and illustrative, not limiting in scope.

An embodiment of the present invention described herein provides a method for producing a plant or photosynthetic organism overexpressing one or more monooxygenase protein ("FMO") coding sequences in the plant or photosynthetic organism, where the method comprises growing a plant or photosynthetic organism having an FMO protein operably linked to a promoter and stably integrated into the plant or photosynthetic organism's nuclear genome or the plant or photosynthetic organism's chloroplast genome under conditions suitable for overexpression of the FMO protein in the plant or photosynthetic organism, wherein the overexpression of the FMO protein coding sequence in the plant or photosynthetic organism catalyzes the oxidation of endogenous metabolites containing nucleophilic nitrogen.

An embodiment of the present invention may comprise a water stress tolerant plant or photosynthetic organism, wherein the water stress tolerant plant or photosynthetic organism overexpresses FMO proteins in the plant's or photosynthetic organism's nuclear genome or the plant's chloroplast genome.

An embodiment of the present invention may comprise a DNA construct for the overexpression of an FMO protein coding sequences in photosynthetic organisms, wherein DNA construct comprises a promoter and the FMO protein coding sequence, wherein said promoter is operably linked to said FMO protein coding sequence, wherein the FMO protein coding sequence is selected from SEQ ID NO: 2, SEQ ID NO: 4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO: 26, SEQ ID NO:28, SEQ ID NO:30, SEQ ID NO:32, SEQ ID NO:34, SEQ ID NO:36, SEQ ID NO:38, SEQ ID NO:40, SEQ ID NO:42 and SEQ ID NO:43.

As used herein "gene expression" and "expression" are to be understood as being synonymous and mean the realization of the information which is stored in a nucleic acid molecule. The terms "polypeptide" and "protein" are used herein interchangeably.

Various components are referred to herein as "operably linked", "linked" or "operably associated." As used herein, "operably linked", "operative linkage", "linked" or "operably associated" refers to nucleic acid sequences on a single nucleic acid fragment so that the function of one is affected by the other. For example, a promoter is operably linked with a coding sequence when it is capable of affecting the expression of that coding sequence.

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

As used herein, "sometime" means at some indefinite or indeterminate point of time. So for example, as used herein, "sometime after" means following, whether immediately following or at some indefinite or indeterminate point of time following the prior act.

Various embodiments are set forth in the Detailed Description as provided herein and as embodied by the claims. It should be understood, however, that this Summary does not contain all of the aspects and embodiments of the present invention, is not meant to be limiting or restrictive in any manner, and that the invention(s) as disclosed herein is/are understood by those of ordinary skill in the art to encompass obvious improvements and modifications thereto.

Additional advantages of the present inventions will become readily apparent from the following discussion, particularly when taken together with the accompanying drawings and sequence listings.

BRIEF DESCRIPTION OF THE SEQUENCE LISTINGS

SEQ ID NO: 1 discloses the At FMO GS-OX5 nucleic acid sequence (NM_101086.41) (At1g12140).
SEQ ID NO: 2: discloses the At FMO GS-OX5 amino acid sequence (NM_101086.41) (At1g12140).
SEQ ID NO: 3 discloses the Br FMO GS-OX1 nucleic acid sequence (FJ376070.1).
SEQ ID NO: 4 discloses the Br FMO GS-OX1 amino acid sequence (FJ376070.1).
SEQ ID NO: 5 discloses the Cs FMO GS-OX3 nucleic acid sequence (XM_004150596.1) (LOC101212991).
SEQ ID NO: 6 discloses the Cs FMO GS-OX3 amino acid sequence (XM_004150596.1) (LOC101212991).
SEQ ID NO: 7 discloses the Cs FMO GS-OX3 nucleic acid sequence (XM_004150602.1) (LOC101220318).
SEQ ID NO: 8 discloses the Cs FMO GS-OX3 amino acid sequence (XM_004150602.1) (LOC101220318).
SEQ ID NO: 9 discloses the Cs FMO GS-OX3 nucleic acid sequence (XM_004170413.1) (LOC101220079).
SEQ ID NO: 10 discloses the Cs FMO GS-OX3 amino acid sequence (XM_004170413.1) (LOC101220079).
SEQ ID NO: 11 discloses the Cs FMO GS-OX3 nucleic acid sequence (XM_004164404.1) (LOC101227975).
SEQ ID NO: 12 discloses the Cs FMO GS-OX3 amino acid sequence (XM_004164404.1) (LOC101227975).
SEQ ID NO: 13 discloses the Mt FMO GS-OX5 nucleic acid sequence (XM_003611223.1) (MTR_5g012130).
SEQ ID NO: 14 discloses the Mt FMO GS-OX5 amino acid sequence (XM_003611223.1) (MTR_5g012130).
SEQ ID NO: 15 discloses the Os FMO nucleic acid sequence (NC 008403.2).
SEQ ID NO: 16 discloses the Os FMO amino acid sequence (NP 001065338.1).
SEQ ID NO: 17 discloses the Vv FMO GS-OX3-3 nucleic acid sequence (XM_003631392.1) (LOC100255688).
SEQ ID NO: 18 discloses the Vv FMO GS-OX3-3 amino acid sequence (XM_003631392.1) (LOC100255688).
SEQ ID NO: 19 discloses the Vv FMO GS-OX3-2 nucleic acid sequence (XM_003631391.1) (LOC100255688).
SEQ ID NO: 20 discloses the Vv FMO GS-OX3-2 amino acid sequence (XM_003631391.1) (LOC100255688).
SEQ ID NO: 21 discloses the Vv FMO GS-OX3-2 nucleic acid sequence (XM_003635084.1) (LOC100242032).
SEQ ID NO: 22 discloses the Vv FMO GS-OX3-2 amino acid sequence (XM_003635084.1) (LOC100242032).
SEQ ID NO: 23 discloses the Gh FMO-1 nucleic acid sequence (DQ122185.1).
SEQ ID NO: 24 discloses the Gh FMO-1 amino acid sequence (DQ122185.1).
SEQ ID NO: 25 discloses the Zm FMO nucleic acid sequence (NM_001157345.1).
SEQ ID NO: 26 discloses the Zm FMO amino acid sequence (NP_001150817.1).
SEQ ID NO: 27 discloses the Pt FMO GS-OX nucleic acid sequence (XM_002329873.1).
SEQ ID NO: 28 discloses the Pt FMO GS-OX amino acid sequence (XM_002329873.1).
SEQ ID NO: 29 discloses the Pt FMO GS-OX nucleic acid sequence (XM_002318967.1).
SEQ ID NO: 30 discloses the Pt FMO GS-OX amino acid sequence (XM_002318967.1).
SEQ ID NO: 31 discloses the Pt FMO GS-OX nucleic acid sequence (XM_002329874.1).
SEQ ID NO: 32 discloses the Pt FMO GS-OX amino acid sequence (XM_002329874.1).
SEQ ID NO: 33 discloses the Gm FMO nucleic acid sequence (NM_003538657.1).
SEQ ID NO: 34 discloses the Gm FMO amino acid sequence (XP_003538705.1).
SEQ ID NO: 35 discloses the Sl FMO GS-OX nucleic acid sequence (XM_004241959.1) (LEFL1075CA11).
SEQ ID NO: 36 discloses the Sl FMO GS-OX amino acid sequence (XP_004242007.1) (LEFL1075CA11).
SEQ ID NO: 37 discloses the Sl FMO GS-OX nucleic acid sequence (SGN-U584070) (Solyc06g060610).
SEQ ID NO: 38 discloses the Sl FMO GS-OX amino acid sequence (SGN-U584070) (Solyc06g060610).
SEQ ID NO: 39 discloses the Hs FMO-3 nucleic acid sequence (NC_000001.10 (171,060,018 . . . 171,086,961)).
SEQ ID NO: 40 discloses the Hs FMO-3 amino acid sequence (NP_001002294.1).
SEQ ID NO: 41 discloses the Oc FMO-3 nucleic acid sequence (NC_013681.1).
SEQ ID NO: 42 discloses the Oc FMO-3 amino acid sequence (NP_001075714.1).
SEQ ID NO: 43 discloses the consensus sequence of the polypeptide SEQ ID No. from 2 to 38.
SEQ ID NO: 44 discloses the 5'UTR in combination with the DNA sequence of AtFMO GS.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

FIG. 3a is a map of a DNA construct that may be used to obtain the *Zea mays* plants for constitutive overexpression of the Zm FMO protein coding sequence that includes (from 5' to 3'), constitutive promoter (Ubiqutin), an FMO protein coding sequence (Zm FMO), a second promoter (35S) and a selectable marker (hygromycin) stably integrated into a pCAMBIA 1300 vector.

FIG. 3b is a map of a DNA construct that may be used to obtain the *Solanum lycopersicum* plants for overexpression of the S1 FMO GS-OX1 protein coding sequence, that includes (from 5' to 3'), a stress inducible promoter (PRO$_{RD29A}$), an FMO protein coding sequence (SI FMO GS-OX1), a second promoter (35S) and a selectable marker (hygromycin) stably integrated into a pCAMBIA 1300 vector.

DETAILED DESCRIPTION OF THE EMBODIMENTS

Figure 1:
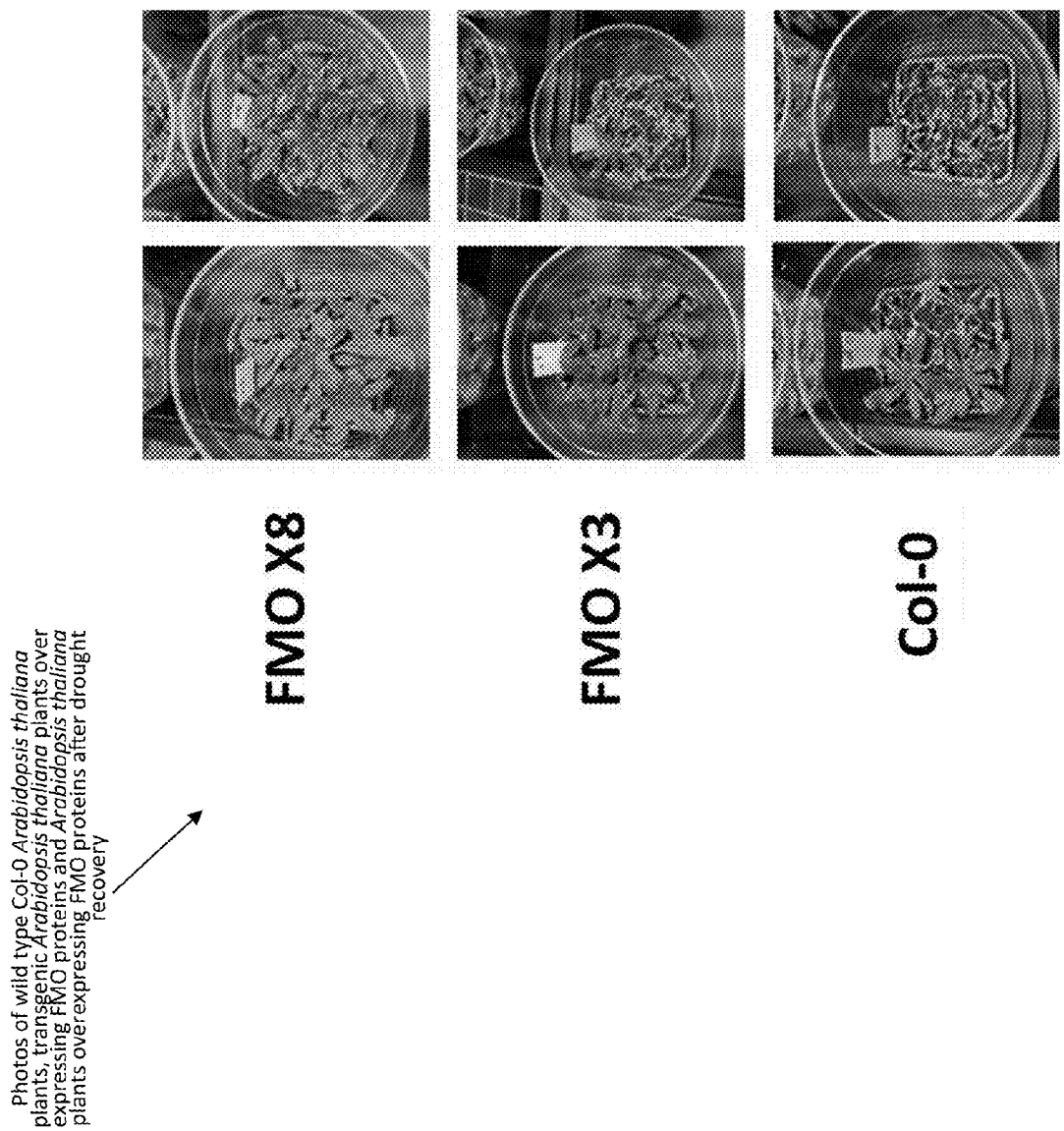
FIG. 1 shows, from the bottom, wild type Col-0 (labeled Col-0) *Arabidopsis thaliana* plants, in the middle (labels FOM X3), transgenic *Arabidopsis thaliana* plants over expressing three copies of the At FMO GS-OX5 sequence and in the upper panel (labeled FOM X8) transgenic *Arabidopsis thaliana* plants over expressing eight copies of the At FMO GS-OX5 sequence after drought recovery.

One or more embodiments described herein include methods for producing transgenic plants or photosynthetic organisms tolerant to water stress which include but is not limited to stably introducing a construct into the plant or photosynthetic organism where the construct includes a gene or genes such as SEQ ID NO:1 or SEQ ID NO: 2 encoding a monooxygenase protein or FMO protein such as the FMO GS-OX5 protein. The overexpression, either constitutive or stress induced, of the monooxygenase protein mediates an increased TMAO expression in a plant or photosynthetic organism through the catalyzation of the oxidation of endogenous metabolites containing nucleophilic nitrogen. Additional embodiments may comprise a transgenic plant or organism overexpressing a water stress tolerant gene, such as SEQ ID NO:1 or SEQ ID NO: 2 encoding an FMO protein, where the gene is operably linked to a constitutive promoter or a stress inducible promoter and has been stably integrated into the plant or organism's genome under conditions suitable for the overexpression of a water stress tolerance protein.

In another embodiment, a method is provided herein for producing a plant or photosynthetic organism with a tolerance to water stress, such as a monocotyledonous or dicotyledonous plant, which comprises introducing into and overexpressing in the plant or photosynthetic organism a nucleic acid or amino acid such as SEQ ID NO:1 or SEQ ID NO: 2 which codes for a monooxygenase protein, such as the FMO GS-OX5 protein.

The constitutive overexpression or stress induced overexpression of the monooxygenase or FMO protein mediates an increased TMAO expression in a plant or photosynthetic organism, increasing the plant or organism's tolerance to various forms of water stress when compared to wild type plants, wild type plant parts, wild type photosynthetic organisms or wild type plant cells. The monooxygenase or FMO protein may be overexpressed in the plant or photosynthetic organism as a whole or a part, is provided, for example in an organ, tissue, a cell, or a part of a plant cell, for example, in an organelle. The monooxygenase protein comprises an amino acid coding sequence having at least 80% identity with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43, and/or the 5'-untranslated region (5'UTR). The overexpression of the protein mediates an increased TMAO expression in a plant or photosynthetic organism, increasing the plant or organism's tolerance to various forms of water stress when compared to wild type plants. By way of example, human FMO1 and FMO3 proteins have an identity of 53% and 84% with the FMO3 proteins from rabbit (see Lawton et al, 1994, *Archives of Biochemistry and Biophysics*, Vol. 308, 254-257).

Further embodiments as disclosed herein provide for a DNA construct comprising one or more FMO protein coding sequences operably linked to a constitutive promoter or a stress inducible promoter wherein the FMO proteins are stably integrated into a plant or photosynthetic organism DNA genome under conditions suitable for overexpression of the DNA construct in the plant or photosynthetic organism. The constitutive promoter or stress inducible promoter in the DNA construct induces overexpression of the FMO proteins in the plant or photosynthetic organism thereby mediating an increased TMAO expression in a plant or photosynthetic organism, increasing the plant or photosynthetic organism's tolerance to various forms of water stress when compared to wild type plants or wild type photosynthetic organisms.

An embodiment of the present invention may comprise DNA constructs for the overexpression of FMO proteins in the transgenic plants or photosynthetic organisms. Such DNA constructs may be represented as shown in FIGS. 2a, 2b, 3a, and 3b.

Figure 2A:
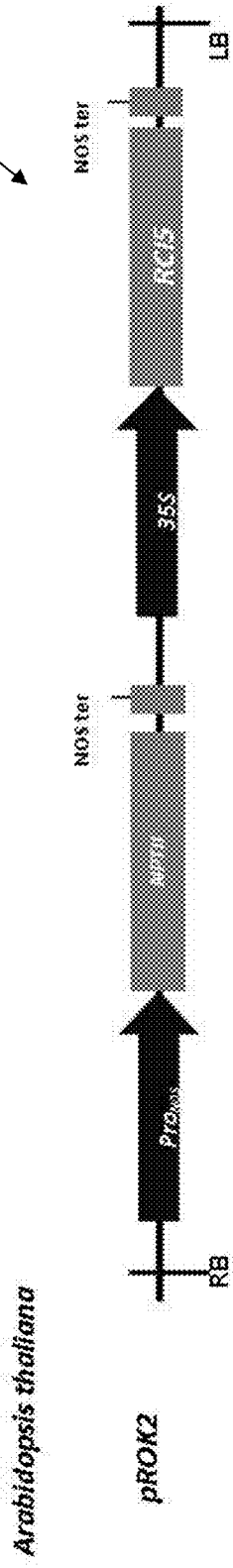
FIG. 2a is a map of a DNA construct that may be used to obtain the *Arabidopsis thaliana* plants for constitutive overexpression of the At FMO GS-OX5 sequence, which includes (from 5' to 3'), a promoter ($PRO_{NOS}$), a selectable marker (NPTII), a constitutive promoter (35S) and a FMO protein coding sequence (RCI5) stably integrated into a pROK2 vector.

As shown in FIG. 2a, a construct for overexpression of an FMO protein in an *Arabidopsis thaliana* plant is provided, where staring at the 5' end of the construct, a constitutive promoter coding sequence, such as PRO$_{NOS}$, is provided with a transcription start site. A selectable marker, such as NPTII is provided with a transcription termination region, NOS ter on the 3'end of the selectable marker. A constitutive promoter, such as the CaMv35S promoter, (35S) is provided with a transcription start site. The FMO protein coding sequence RCI5 (SEQ ID NO: 1 or SEQ ID NO:2) is provided with a transcription termination region, NOS ter on the 3'end of the FMO protein coding sequence. Each of these components is operably linked to the next, i.e., the constitutive promoter coding sequence, PRO$_{NOS}$, is operably linked to the 5' end of the selectable marker, NPTII, protein sequence and the selectable marker protein sequence is operably linked to the 5' end of the CaMv35S constitutive promoter coding sequence which is operably linked to the 5' end of the FMO protein coding sequence RCI5. For overexpression, the expression vector pROK2 may be used. The DNA construct is then integrated into a plant or photosynthetic organism such as an *Arabidopsis thaliana* plant and photosynthetic organisms overexpressing the At FMO GS-OX5 protein are produced, where the constitutive promoter induces the overexpression of the FMO protein. The overexpression of the FMO protein coding sequence in plant or photosynthetic organism catalyzes the oxidation of endogenous metabolites containing nucleophilic nitrogen.

Figure 2B:
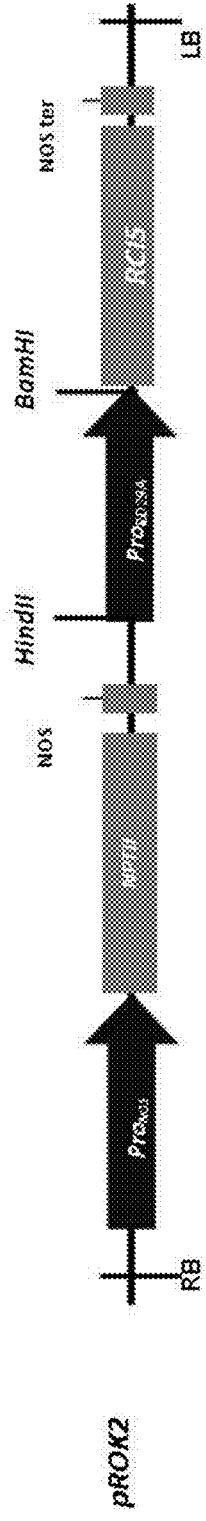
FIG. 2b is a second map of a DNA construct that may be used to obtain the *Arabidopsis thaliana* plants for constitutive overexpression the At FMO GS-OX5 sequence, that includes (from 5' to 3'), a promoter ($PRO_{NOS}$), a selectable marker (NPTII), a stress inducible promoter (PRO$_{RD29A}$) and a FMO protein coding sequence (RCI5) stably integrated into a pROK2 vector.

As shown in FIG. 2b, a construct for overexpression of an FMO protein in an *Arabidopsis thaliana* plant is provided, where staring at the 5' of the construct a promoter coding sequence, such as PRO$_{NOS}$, is provided with a transcription start site. A selectable marker, such as NPTII is provided with a transcription termination region, NOS site on the 3'end of the selectable marker. A stress inducible promoter, such as the PRO$_{RD29A}$ promoter, with a HindII site on the 5' end and BamHI site on the 3' end, is provided with a transcription start site. FMO protein coding sequence RCI5 (SEQ ID NO: 1 or SEQ ID NO:2) is provided with a transcription termination region, NOS ter site on the 3'end of the FMO protein coding sequence. Each of these components is operably linked to the next, i.e., the promoter coding sequence, PRO$_{NOS}$, is operably linked to the 5' end of the selectable marker, NPTII, protein coding sequence and the selectable marker protein coding sequence is operably linked to the 5' end of the PRO$_{RD29A}$ constitutive promoter coding sequence which is operably linked to the 5' end of the FMO protein coding sequence RCI5. For overexpression, the expression vector pROK2 may be used. The DNA construct is then integrated into a plant or photosynthetic organism such as an *Arabidopsis thaliana* plant and organisms overexpressing the At FMO GS-OX5 protein are produced, where the stress inducible promoter induces the overexpression of the FMO protein. The overexpression of the FMO protein coding sequence in photosynthetic organism catalyzes the oxidation of endogenous metabolites containing nucleophilic nitrogen.

As shown in FIG. 3a, a construct for overexpression of an FMO protein in a *Zea mays* plant is provided, where staring at the 5' a constitutive promoter coding sequence, such as the Ubiquitin promoter, is provided with a transcription start site. FMO protein coding sequence SI FMO GX-OX1 (SEQ ID NO: 25 or SEQ ID NO:26) is provided with a transcription termination region, NOS ter site on the 3'end of the FMO protein coding sequence. A constitutive promoter, such as the CaMv35S promoter, (35S) is provided with a transcription start site. A selectable marker, such as hygromycin is provided with a transcription termination region, NOS ter on the 3'end of the selectable marker. Each of these components is operably linked to the next, i.e., the constitutive promoter coding sequence, Ubiquitin, is operably linked to the 5' end of the FMO protein coding sequence ZM FMO, the FMO protein coding sequence is operably linked to the 5' end of the constitutive promoter, such as the CaMv35S promoter, (35S) coding sequence which is operably linked to the 5' end of the selectable marker protein coding sequence. For overexpression, the expression vector pCAMBIA 1300 may be used. The DNA construct is then integrated into a plant or photosynthetic organism such as a *Zea mays* plant and organisms overexpressing the ZM FMO protein are produced, where the constitutive promoter induces the overexpression of the FMO protein and the overexpression of the FMO protein coding sequence in photosynthetic organism catalyzes the oxidation of endogenous metabolites containing nucleophilic nitrogen.

As shown in FIG. 3b, a construct for overexpression of an FMO protein in a *Solanum lycopersicum* plant is provided, where staring at the 5' a stress inducible promoter, such as the PRO$_{RD29A}$ promoter, is provided with a transcription start site. FMO protein coding sequence SI FMO GS-OX1 (SEQ ID NO: 35, SEQ ID NO: 36, SEQ ID NO: 37 or SEQ ID NO: 38) is provided with a transcription termination region, NOS ter site on the 3'end of the FMO protein coding sequence. A constitutive promoter, such as the CaMv35S promoter, (35S) is provided with a transcription start site. A selectable marker, such as hygromycin is provided with a transcription termination region, NOS ter on the 3'end of the selectable marker. Each of these components is operably linked to the next, i.e., the stress inducible promoter coding sequence, PRO$_{RD29A}$ promoter, is operably linked to the 5' end of the FMO protein coding sequence SI FMO GS-OX1, the FMO protein coding sequence is operably linked to the 5' end of the constitutive promoter, such as the CaMv35S promoter, (35S) coding sequence which is operably linked to the 5' end of the selectable marker protein coding sequence. For overexpression, the expression vector pCAMBIA 1300 may be used. The DNA construct is then integrated into a photosynthetic organism such as a *Solanum lycopersicum* plant and organisms overexpressing the SI FMO GS-OX1 protein are produced, where the stress inducible promoter induces the overexpression of the FMO protein and the overexpression of the FMO protein coding sequence in photosynthetic organism catalyzes the oxidation of endogenous metabolites containing nucleophilic nitrogen.

As used herein, "nucleic acids" means biopolymers of nucleotides which are linked with one another via phosphodiester bonds (polynucleotides, polynucleic acids). Depending on the type of sugar in the nucleotides (ribose or deoxyribose), one distinguishes the two classes of the ribonucleic acids (RNA) and the deoxyribonucleic acids (DNA).

As introduced above, an embodiment of the present disclosure provides a method for producing plants tolerant to water stress, including but not limited to drought tolerance or excessive moisture, in plants wherein an application of trimethylamine N-oxide or "TMAO", wherein TMAO includes but is not limited to, TMAO dihydrate, TMAO chemical derivative, or a TMAO chemical analogue, to a plant or seed to reduce water stress in the plant when the plant is exposed to water stress conditions. This method of producing a plant tolerant to water stress is applicable to a variety of plants including monocotyledonous or dicotyledonous plants, including but not limited to transgenic plants. As used herein, transgenic plants include plants, or photosynthetic organism, which have been genetically modified to contain foreign DNA constructs as will be discussed further herein. The methods for producing a plant or organism tolerant to water stress may be applicable to the whole plant or organism or a part of a plant, for example in an organ, tissue, a cell or a part of a plant cell, for example in an organelle, which comprises introducing into, and expressing in, the plant or plant cell a nucleic acid which codes for a monooxygenase or FMO protein, and which mediates an increased production of endogenous TMAO and therefore a water stress tolerance, such as an increased tolerance to drought or an increased tolerance to excessive moisture.

Methylamines (e.g. trimethylamine N-oxide (TMAO)) can enhance protein folding and ligand binding and counteract perturbations by urea (e.g. in elasmobranchs and mammalian kidney), inorganic ions, and hydrostatic pressure in deep-sea animals (Yancey, 2005).

Another embodiment provided herein and as will be described in further detail is a method for water stress tolerance in a plant, a plant part, or a plant cell, where the method comprises the step of increasing the expression and/or activity of a monooxygenase protein in the plant, plant part, or plant cell in comparison to a wild type plant, wild type plant part or wild type plant cell.

As used herein the term "water stress" includes drought stress and excessive moisture stress. The term "drought stress" as used herein can be induced in plants under conditions where reduced water content in the soil, due to a shortage of rainfall or irrigation, leads to impaired or reduced water absorption by the plant. The term "excessive moisture" can be induced in plants where excessive water content of the soil also leads to impaired water absorption by the plant. Water stress may trigger in plants a deterioration of physiological functions of cells, thereby leading to various disorders. While the conditions which induce drought stress may vary depending on the kind of the soil where plants are cultivated, examples of the conditions include but are not limited to: a reduction in the water content in the soil of 15% by weight or less, more severely 10% by weight or less, and still more severely 7.5% by weight or less; or the pF value of the soil of 2.3 or more, more severely 2.7 or more, and still more severely 3.0 or more.

As used herein, water stress in plants may be recognized or identified by comparing a change in plant phenotypes described in more detail below between plants which have been exposed to water stress conditions and plants which have not been exposed to the same water stress conditions. Water stress in a plant or organism may be indicated by a change in one or more of the following plant phenotypes, which can serve as indicators of the water stress in plants: (1) germination percentage, (2) seedling establishment rate, (3) number of healthy leaves, (4) plant length, (5) plant weight, (6) leaf area, (7) leaf color, (8) number or weight of seeds or fruits, (9) quality of harvests, (10) flower setting rate or fruit setting rate, (11) chlorophyll fluorescence yield, (12) water content, (13) leaf surface temperature, and (14) transpiration capacity.

Water stress may be quantified as the "intensity of stress" represented by the following equation.

"Intensity of stress"=100×"any one of plant phenotypes in plants which have not been exposed to water stress"/"the plant phenotype in plants which have been exposed to water".

The methods described herein are applied to plants that have been exposed to or to be exposed to water stress conditions whose Intensity of Stress represented by the above equation is from 105 to 450, preferably from 110 to 200, and more preferably from 115 to 160. In a plant exposed to water stress conditions, an influence may be recognized on at least one of the above phenotypes. That is, observed as: (1) decrease in germination percentage, (2) decrease in seedling establishment rate, (3) decrease in number of healthy leaves, (4) decrease in plant length, (5) decrease in plant weight, (6) decrease in leaf area increasing rate, (7) leaf colour fading, (8) decrease in number or weight of seeds or fruits, (9) deterioration in quality of harvests, (10) decrease in flower setting rate or fruit setting rate, (11) decrease in chlorophyll fluorescence yield, (12) decrease in water content, (13) increase in leaf surface temperature, or (14) decrease in transpiration capacity, among others, and the magnitude of the water stress in the plant can be measured using that as an indicator.

As discussed above, the methods described herein are directed to methods for reducing water stress in a plant or organism by producing a plant or photosynthetic organism tolerant to water stress by overexpressing FMO to the plant that has been exposed to or will be exposed to water stress conditions. The effect of reducing the water stress of a plant or photosynthetic organism can be evaluated by comparing the above phenotypic indicators between a overexpressing FMO and a plant which does not overexpress FMO after the plants or photosynthetic organism are exposed to water stress conditions. Stages in which plants or photosynthetic organism overexpressing FMO can be exposed to the water stress conditions include, for example, all growth stages of plants, including a germination period, a vegetative growing period, a reproductive growing period and a harvesting period.

A variety of seeds or bulbs may be used in the methods described herein including but are not limited to plants in the families Solanaceae and Cucurbitaceae, as well as plants selected from the plant genera *Calibrachoa, Capsicum, Nicotiana, Nierembergia, Petunia, Solanum, Cucurbita, Cucumis, Citrullus, Glycine*, such as *Glycine max* (Soy), *Calibrachoa×hybrida, Capsicum annuum* (pepper), *Nicotiana tabacum* (tobacco), *Nierenbergia scoparia* (cupflower), *Petunia×hybrida, Solanum lycopersicum* (tomato), *Solanum tuberosum* (potato), *Solanum melongena* (eggplant), *Cucurbita maxima* (squash), *Cucurbita pepo* (pumpkin, zucchini), *Cucumis metuliferus* (Horned melon) *Cucumis melo* (Musk melon), *Cucumis sativus* (cucumber) and *Citrullus lanatus* (watermelon). Various monocotyledonous plants, in particular those which belong to the family Poaceae, may be used with the methods described herein, including but not limited to, plants selected from the plant genera *Hordeum, Avena, Secale, Triticum, Sorghum, Zea, Saccharum, Oryza, Hordeum vulgare* (barley), *Triticum aestivum* (wheat), *Triticum aestivum* subsp. *spelta* (spelt), *×Triticosecale* (Triticale), *Avena sativa* (oats), *Secale cereale* (rye), *Sorghum bicolor* (sorghum), *Zea mays*(maize), *Saccharum officinarum* (sugarcane) and *Oryza sativa* (rice). Additional examples of plants in which water stress may be produced using the methods described herein include the followings. crops: buckwheat, beet, canola, rapeseed, sunflower, sugar cane, tobacco, and pea, etc.; vegetables: solanaceous vegetables such as paprika and potato; cucurbitaceous vegetables; cruciferous vegetables such as Japanese radish, white turnip, horseradish, kohlrabi, Chinese cabbage, cabbage, leaf mustard, broccoli, and cauliflower, asteraceous vegetables such as burdock, crown daisy, artichoke, and lettuce; liliaceous vegetables such as green onion, onion, garlic, and asparagus; ammiaceous vegetables such as carrot, parsley, celery, and parsnip; chenopodiaceous vegetables such as spinach, Swiss chard; lamiaceous vegetables such as *Perilla frutescens*, mint, basil; strawberry, sweet potato, *Dioscorea japonica, colocasia*; flowers; foliage plants; grasses; fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, tangerine, lemon, lime, grapefruit, etc.), nuts (chestnuts, walnuts, hazelnuts, almond, pistachio, cashew nuts, macadamia nuts, etc.), berries (blueberry, cranberry, blackberry, raspberry, etc.), grape, kaki fruit, olive, Japanese plum, banana, coffee, date palm, coconuts, etc.; and trees other than fruit trees; tea, mulberry, flowering plant, roadside trees (ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidate*). Examples of plants in which water stress tolerance may be produced may include rice, corn, canola, soybean and wheat. The aforementioned "plants" include transgenic plants, expressing other gene traits.

As used herein, "plants" means all dicotyledonous or monocotyledonous plants, including but not limited to the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. "Mature plants" means plants at any developmental stage beyond the seedling stage. Seedling means a young, immature plant in an early developmental stage.

Dicotyledonous plants includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

"Plant" also comprises annual and perennial dicotyledonous or monocotyledonous plants and includes by way of example, but not by limitation, those of the genera *Glycine, Vitis, Asparagus, Populus, Pennisetum, Lolium, Oryza, Zea, Avena, Hordeum, Secale, Triticum, Sorghum, Saccharum* and *Lycopersicum*.

As used herein "photosynthetic organisms" may include but is not limited to organisms such as *Arthrospira* spp., *Spirulina* spp., *Synechococcus elongatus, Synechococcus* spp., *Synechosystis* spp., *Synechosystis* spp. and *Spirulina plantensis, Calothrix* spp., *Anabaena flosaquae, Aphanizomenon* spp., *Anabaena* spp., *Gleotrichia* spp., *Oscillatoria* spp. and *Nostoc* spp.; eukaryotic unicellular *algae* such as but not limited to *Chaetoceros* spp., *Chlamydomonas reinhardtii, Chlamydomonas* spp., *Chlorella vulgaris, Chlorella* spp., *Cyclotella* spp., *Didymosphenia* spp., *Dunaliella tertiolecta, Dunaliella* spp., *Botryococcus braunii, Botryococcus* spp., *Gelidium* spp., *Gracilaria* spp., *Hantzschia* spp., *Hematococcus* spp., *Isochrysis* spp., *Laminaria* spp., *Nannochloropsis* spp., *Navicula* spp., *Nereocystis luetkeana, Pleurochrysis* spp., *Postelsia palmaeformis*, and *Sargassum* spp.

As discussed above, another embodiment provides a method for producing a plant or photosynthetic organism, such as a monocotyledonous or dicotyledonous plant, with a tolerance to water stress, which comprises introducing into and expressing in the plant or photosynthetic organism a nucleic acid or amino acid such as SEQ ID NO:1 or SEQ ID NO: 2, which codes for a monooxygenase protein, such as the FMO GS-OX5 protein. An example of the monooxygenase protein may include but is not limited to an amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43, wherein the nucleotide sequence comprises at least one nucleic acid molecule. The amino acid sequence may have a percent identity of 80% or more of the sequences listed above and/or the 5'-untranslated region (5'UTR) in comparison with the original sequence.

The methods described herein also include a) introducing into a plant or photosynthetic organism cell a recombinant expression cassette comprising the nucleic acid molecule in an operable linkage with a promoter which is active in a plant or photosynthetic organisms; b) regenerating a plant or photosynthetic organism from the plant or photosynthetic organism cell, and c) expressing the nucleic acid molecule to generate or to increase a water tolerance in the plant or photosynthetic organism.

The methods described herein further provide a transgenic photosynthetic organisms or a plant, comprising a nucleic acid sequence such as an FMO protein (SEQ ID NOs: 1-43), a DNA expression cassette, or a vector comprising the DNA expression cassette, or comprising a cell comprising the nucleic acid molecule such as the FMO protein (SEQ ID NOs: 1-43), the expression cassette, or the vector. Examples may include generating a transgenic plant which is tolerant to water stress, which may comprise the nucleic acid molecule, such as an FMO protein coding sequence (SEQ ID NOs: 1-43), a DNA expression cassette, a vector comprising the expression cassette, or a cell comprising the nucleic acid molecule, the expression cassette, or the vector. A plant propagation material or composition may be generated comprising a nucleic acid molecule such as the FMO protein coding sequence (such as SEQ ID NOs: 1-43), a DNA expression cassette comprising the FMO protein coding sequence, or a vector comprising the expression cassette, or a cell comprising the nucleic acid molecule, the expression cassette, or the vector to provide a drought tolerant plant, plant part, or plant cell.

As discussed above and shown in FIG. 4, the FMO proteins described herein may include an exogenous nucleotide sequence which codes for an amino acid sequence having at least 50%, 60%, 70%, 75%, 80% 85%, 90%, 95% identity with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43, into a plant or photosynthetic organism, a part of a plant, or a plant cell, and expressing the nucleotide sequence in the plant or photosynthetic organism, the part of the plant, or the plant cell. Further the nucleotide sequence may be increased in the plant or photosynthetic organism, the part of the plant, or the plant cell when compared with the original, or wild-type plant, part of the plant, or plant cell.

Figure 4:
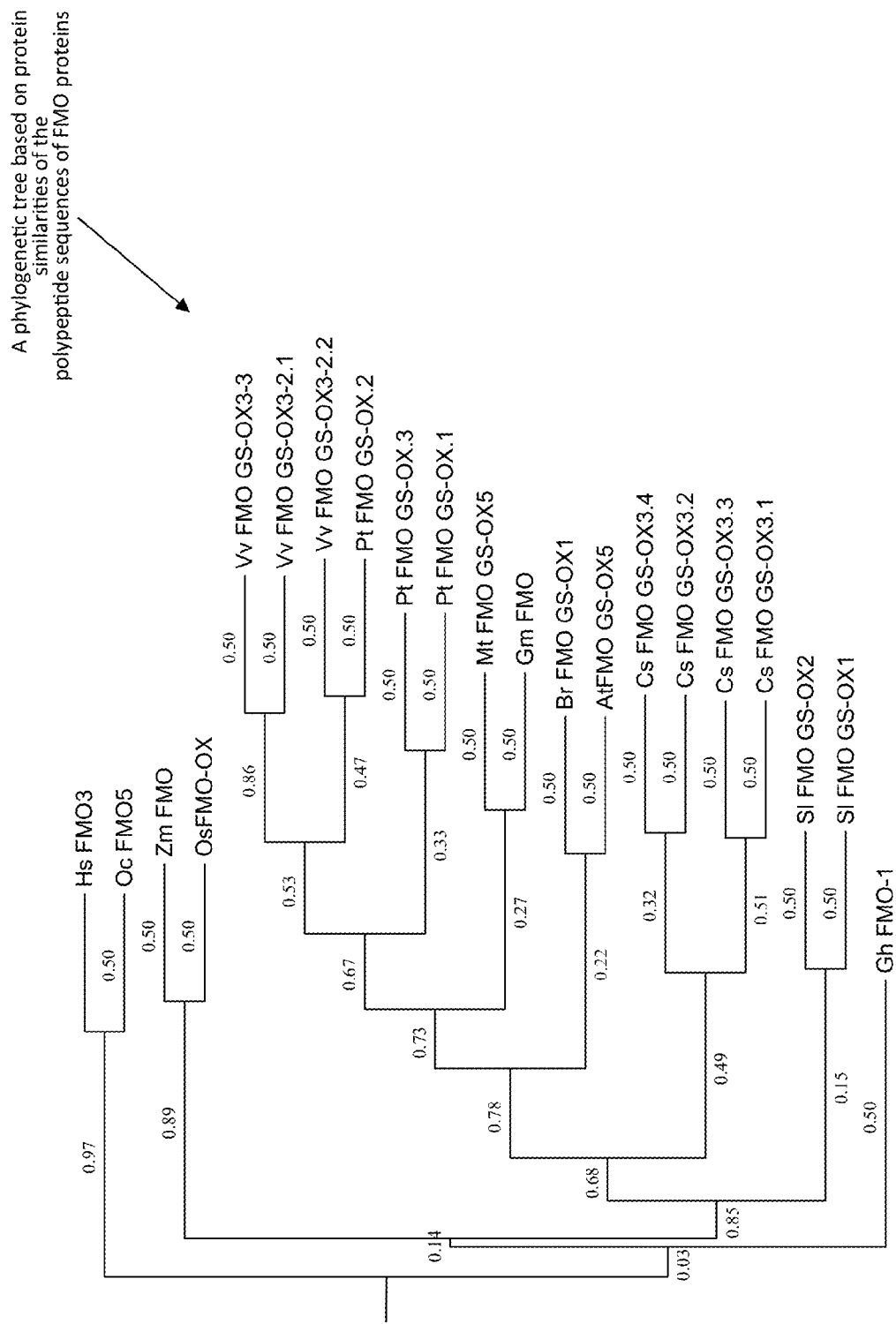
FIG. 4 shows a phylogenetic tree based on protein similarities using the alignment-free algorithm, named CLUSS, for clustering protein families of the polypeptide sequences of FMO from *Arabidopsis thaliana*, grapevine, *Populus trichocarpa*, rice, soybean, melon, tomato, *sorghum*, corn, wheat, barley, human and rabbit.

The methods of overexpression and increase of a FMO protein as described herein, including the one or more DNA constructs for use in the overexpression of FMO protein, stable integration of the FMO protein into a plant or photosynthetic organism DNA genome and overexpression of the DNA construct in the plant or photosynthetic organism, may be used in a variety of plants, including but not limited to: soybean, potato, cotton, rape, oilseed rape, canola, sunflower, alfalfa, clover, banana, blackberry, blueberry, strawberry, raspberry, cantaloupe, carrot, cauliflower, coffee, cucumber, eggplant, grape, honeydew, lettuce, mango, melon, onion, papaya, pepper, pineapple, pumpkin, spinach, squash, tobacco, tomato, tomatillo, watermelon, apple, peach, pear, cherry, plum, broccoli, cabbage, cauliflower, Brussels sprouts, kohlrabi, currant, avocado, orange, lemon, grapefruit, tangerine, artichoke, cherry, walnut, peanut, endive, leek, arrowroot, beet, cassava, turnip, radish, yam, sweet potato; pea, bean, sugarcane, turfgrass, Miscanthus, switchgrass, wheat, maize, sweet corn, rice, millet, sorghum, barley, and rye as well as various types of photosynthetic organisms including but not limited to diatoms, eukaryotic algae and cyanobacteria As shown in FIG. 4, genes with high identity to FMO GS-OX5 mediate similar functions. As shown in FIG. 4 the genes, used nucleic acids or expressed proteins may have 40% or more identity, including but not limited to at least 50%, at least 60%, at least 70%, at least 80%, at least 85%, at least 90%, at least 95%, at least 97%, at least 98%, at least 99% or more identity, in comparison with the respective FMO GS-OX5 sequence of *Arabidopsis* (At1g12140) (SEQ ID NO: 1) [cDNA sequence with UTR] or the protein sequence SEQ ID NO.: 2). The genes with the highest homologies to At1g12140 from *Solanum lycopersicum* SlFMO GS-OX1 (Solyc06g060610) (SEQ ID NO: 37 and SEQ ID NO: 38), SlFMO GS-OX2 (AK324297.1), *Vitis vinifera* VvFMO GS-OX3-1 (SEQ ID NO: 21 and SEQ ID NO: 22) (LOC100242032), VvFMO GS-OX3-2 (LOC100255688) (SEQ ID NO: 19 SEQ ID NO: 20), VvFMO GS-OX3-3 (LOC100255688) (SEQ ID NO: 17 and SEQ ID NO: 18), *Populus trichocarpa* PtFMO-GS-OX3 (XM_002329873.1) (SEQ ID NO: 27 and SEQ ID NO: 28), PtFMO GS-OX2 (XM_002318967.1) (SEQ ID NO: 29 and SEQ ID NO: 30), PtFMO GS-OX1 (XP002318210.1), *Oryza sativa* OsFMO-OX (Os10g40570.1) (SEQ ID NO: 15 and SEQ ID NO: 16), *Glycine max* GmFMO (Glyma11g03390.1) (SEQ ID NO: 33 and SEQ ID NO: 34), *Cucumus sativus* CsFMO GS-OX3-1 (LOC101227975) (SEQ ID NO: 11 and SEQ ID NO: 12), CsFMO GS-OX3-2 (LOC101220079) (SEQ ID NO: 9 and SEQ ID NO: 10), CsFMO GS-OX3-3 (LOC101220318) (SEQ ID NO: 7 and SEQ ID NO: 8), CsFMO GS-OX3-4 (LOC101212991) (SEQ ID NO: 5 and SEQ ID NO: 6), *Brassica rapa* subsp. *pekinensis* BrFMO GS-OX1 (FJ376070.1), *Medicago truncatula* MtFMO GS-OX5 (MTR_5g012130) (SEQ ID NO: 13 and SEQ ID NO: 14), *Zea mays* ZmFMO (GRMZM2G089121_P01) (SEQ ID NO: 25 and SEQ ID NO: 26), *Gossypium hirsutum* GhFMO-1 (DQ122185.1) SEQ ID NO: 23 and SEQ ID NO: 24) *Homo sapiens* HsFMO-3 (NP_001002294.1) (SEQ ID NO: 39 and SEQ ID NO: 40) and *Oryctolagus cuniculus* OcFMO-5 (NP_001075714.1) SEQ ID NO: 41 and SEQ ID NO: 42) probably exert similar functions in the plant or photosynthetic organism as FMO GS-OX5 polypeptide from *Arabidopsis* (AtFMO GS-OX5). As discussed above, FIG. 4 provides aphylogenetic tree of the polypeptide sequences listed above of FMO from *Arabidopsis thaliana*, grapevine, *Populus trichocarpa*, rice, soybean, melon, tomato, sorghum, corn, wheat, barley, human and rabbit.

As shown in FIG. 4, the equivalent expression of FMO proteins may be expected for sequences having 40% or more identity, including but not limited to at least 50%, at least 60%, at least 70%, at least 80%, at least 85%, at least 90%, at least 95%, at least 97%, at least 98%, at least 99% or more identity, in comparison with other FMO sequences such as the respective FMO GS-OX5 sequence of *Arabidopsis*.

As used herein, "FMO protein" or "FMO polypeptide" means a protein with 100% of the full or parts of the sequence, which mediates an increased TMAO expression in a plant or photosynthetic organism through the catalyzation of the oxidation of endogenous metabolites containing nucleophilic nitrogen and conferring enhanced water stress tolerance when expressed in plants or photosynthetic organisms. "FMO protein" is understood as meaning a sequence which comprises an N-terminal domain, a flavin-monooxygenase domain and a C-terminal domain (Li et al., *Plant Physiol.* 148(3):1721-33 (2008). For example, the polypeptide which is employed in the method, has an activity which is involved in the water stress defense responses and increases endogenous TMAO. The FMO protein is encoded for example, by a nucleic acid molecule comprising a nucleic acid molecule selected from the group consisting of: (a) nucleic acid molecule which codes for at least one polypeptide comprising the sequence shown in the nucleic acid sequence which codes for the FMO protein, such as FMO GS-OX5 protein (SEQ ID NO: 1) or the functional parts of the protein, expresses and mediates an increased water stress tolerance, including an increased tolerance to drought. As discussed in the methods above, the FMO protein is introduced into and expressed in the plant or photosynthetic organism or plant cell or a part thereof, or the FMO protein may be expressed endogenously according to the methods described herein.

By way of example the nucleic acid sequence which codes for the FMO protein may be selected from the group consisting of: (a) a nucleic acid molecule which codes for at least one polypeptide comprising the sequence shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43; (b) a nucleic acid molecule which comprises at least one polynucleotide of the sequence shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; (c) a nucleic acid molecule which codes for a polypeptide whose sequences has at least 50%, at least 60%, at least 70%, at least 80%, at least 85%, at least 90%, at least 95%, at least 97%, at least 98% or at least 99%, identity with any one of the sequences shown in paragraph (a) or (b) listed above where the nucleic acid molecule listed in paragraphs (a) and (b) above have the same or a similar biological function as a nucleic acid molecule encoding a polypeptide; (e) nucleic acid molecule according to (a) to (d) which codes for a fragment or an epitope of the sequences as shown in paragraphs (a) and (b), wherein the fragment is a functional fragment which confers water stress tolerance; (f) a nucleic acid molecule which codes for a polypeptide which is recognized by a monoclonal antibody directed against a polypeptide which is encoded by the nucleic acid molecules as shown in (a) to (d); (g) nucleic acid molecule which hybridizes under stringent conditions with the complement of a nucleic acid molecule as shown in (a) to (d); and (h) nucleic acid molecule which can be isolated from a DNA library using a nucleic acid molecule as shown in (a) to (d) or their part-fragments of at least 15 nt, 20 nt, 30 nt, 50 nt, 100 nt, 200 nt or 500 nt, as probe under stringent hybridization conditions; (i) a nucleic acid encoding the same FMO protein as the nucleic acids sequences listed in paragraphs (a) to (d) above, but differing from the sequences of (a) to (d) above due to the degeneracy of the genetic code; or a complementary sequence thereof.

Other heterologous proteins encoded by the chimeric gene include polypeptides that form immunologically active epitopes, and enzymes that catalyze conversion of intracellular metabolites, with the consequent build-up of selected metabolites in the cells.

As used herein, the term "sequence(s)" is used for simplification reasons, and refers, depending on the context, to the nucleic acid and/or amino acid sequences disclosed herein. The skilled worker will know from the context what they refer to. The term "DNA fragment" as used in herein is understood as meaning portions of the DNA which code for a protein when this biological activity consists in mediating an increase in the water stress tolerance. The term "fragments of the protein" as used herein refers to portions of the protein whose biological activity comprises mediating an increase in the water stress tolerance in plants.

"Polypeptide quantity" as used herein means for example, the number of molecules, or moles, of FMO polypeptide molecules in an organism, a tissue, a cell or a cell compartment. Increasing the polypeptide quantity means the molar increase in the number of the respective polypeptides in an organism, a tissue, a cell or a cell compartment. For example, by one of the methods described herein below, in comparison with a suitable control, for example, the wild type (control plant) of the same genus and species to which this method has not been applied, under otherwise identical conditions (such as, for example, culture conditions, age of the plants and the like). The increase in this context amounts to at least 5%, at least 10% or at least 20%, as well as at least 40% or 60%, at least 70% or 80%, and at least 90%, 95%, 99%, 100%, more than 100%, including 150%, 200% or 300%.

Identity between two nucleic acid sequences is understood as meaning the identity of the nucleic acid sequence over in each case the entire sequence length, which is calculated by comparison with the aid of the program algorithm GAP (Wisconsin Package Version 10.0, University of Wisconsin, Genetics Computer Group (GCG), Madison, USA; Altschul et al., Nucleic Acids Res. 25, 3389 (1997)), setting the following parameters:\

| Gap weight: 50 | Length weight: 3' |
|---|---|
| Average match: 10 | Average mismatch: 0 |

For example, a sequence which has at least 80% identity with the sequence SEQ ID NO: 1 at the nucleic acid level is understood as meaning a sequence which, upon comparison with the sequence SEQ ID NO: 1 by the above program algorithm with the above parameter set, has at least 80% identity.

Identity between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:

| Gap weight: 8 | Length weight: 2 |
|---|---|
| Average match: 2.912 | Average mismatch: −2.003 |

For example, a sequence which has at least 80% identity at the polypeptide level with the sequence SEQ ID NO: 2 is understood as meaning a sequence which, upon comparison with the sequence SEQ ID NO: 2 by the above program algorithm with the above parameter set, has at least 80% identity.

The water stress tolerance of a plant or organism as described herein is obtained by introducing and overexpressing a nucleic acid sequence such as but not limited to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43. Additionally, it is also possible to increase the endogenous overexpression or activity of these sequences in a plant or organism by methods known to one skilled in the art. For example an increase in endogenous overexpression may be obtained by mutating a UTR region, such as the 5'-UTR, a promoter region, a genomic coding region for the active center, for binding sites, for localization signals, for domains, clusters and the like, such as, for example, of coding regions for the N-terminal, the FMO protein or the C-terminal domains. The endogenous expression or activity may be increased in accordance with the invention by mutations which affect the secondary, tertiary or quaternary structure of the protein.

Mutations can be inserted for example, by an EMS mutagenesis. Domains can be identified by suitable computer programs such as, for example, SMART or InterPRO, for example as described in Andersen P., *The Journal of Biol. Chemistry*, 279, 38 or 39053, (2004) or Mudgil, Y., *Plant Physiology*, 134, 59, (2004), and literature cited therein. The suitable mutants can then be identified for example by TILLING (for example as described by Henikoff, S., et al., *Plant Physiol.* 135: 630-6 (2004)).

The introduction and overexpression of a sequence according to the methods described herein into a plant or photosynthetic organism, or increasing or modifying or mutating an endogenous sequence, if appropriate of one or both untranslated regions, in a plant or photosynthetic organism is combined with increasing the polypeptide quantity, activity or function of other resistance factors, such as a Bax inhibitor 1 protein (BI-1), such as a Bax inhibitor 1 protein from *Hordeum vulgare* (GenBank Acc.-No.: AJ290421), from, *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc N et al. (2003) *Planta* 216, 377 (2003)) or of ROR2 (for example from barley (GenBank Acc.-No.: AY246906), SnAP34 (for example, from barley (GenBank Acc.-No.: AY247208) and/or of the lumenal binding protein BiP for example from rice (GenBank Acc.-No. AF006825). An increase can be achieved for example, by mutagenesis or overexpression of a transgene, inter alia.

A nucleic acid molecule, as used herein, comprises the untranslated sequence at the 3' and at the 5' terminus of the coding gene region: at least 500, or 200, or 100 nucleotides of the sequence upstream of the 5' terminus of the coding region and at least 100, or 50, or 20 nucleotides of the sequence downstream of the 3' terminus of the coding gene region.

Moreover, nucleic acid sequences are isolated nucleic acid sequences. An "isolated" nucleic acid molecule is separated from other nucleic acid molecules which are present in the natural origin of the nucleic acid. An "isolated" nucleic acid preferably contains no sequences which naturally flank the nucleic acid in the genomic DNA of the organism from which the nucleic acid originates (for example sequences which are located at the 5' and 3' termini of the nucleic acid; however, this does not affect the abovementioned embodiments comprising 5'- and 3'-UTR regions). In different embodiments, the isolated molecule may comprise for example less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid originates. All the nucleic acid molecules mentioned here may be for example RNA, DNA or cDNA.

The nucleic acid molecules may be isolated using standard techniques of molecular biology and the sequence information provided herein. Using comparative algorithms, it is possible to identify for example a homologous sequence, or homologous, conserved sequence regions, at the DNA or amino acid level. Essential portions of this sequence or the entire homologous sequence can be used as hybridization probe using standard hybridization techniques (such as, for example, described in Sambrook et al.: *Molecular Cloning. A Laboratory Manual,* 2nd ed. Cold Spring Harbor Laboratory Press, Cold Spring Harbor, N.Y., 1989) for isolating further nucleic acid sequences which are useful in the method from other organisms by screening cDNA libraries and/or genomic libraries.

Moreover, a nucleic acid molecule or a part thereof can be isolated by means of polymerase chain reaction ("PCR"), where oligonucleotide primers based on the sequences specified herein or parts thereof are used (for example, it is possible to isolate a nucleic acid molecule comprising the complete sequence or part thereof by means of PCR using oligonucleotide primers which have been generated on the basis of the very same sequence). For example, mRNA can be isolated from cells (for example by the guanidinium thiocyanate extraction method by Chirgwin et al., *Biochemistry* 18, 5294 (1979)) and cDNA prepared therefrom by means of reverse transcriptase (for example Moloney MLV reverse transcriptase, obtainable from Gibco/BRL, Bethesda, Md. or AMV reverse transcriptase, available from Seikagaku Amerika, Inc., St. Petersburg, Fla.). Synthetic oligonucleotide primers for the amplification by means of PCR can be generated on the basis of the sequences disclosed herein. A nucleic acid can be amplified using cDNA or, alternatively, genomic DNA as template and suitable oligonucleotide primers by means of standard PCR amplification techniques. The nucleic acid amplified thus can be cloned into a suitable vector and characterized by means of DNA sequence analysis. Oligonucleotides which correspond to a nucleotide sequence coding for a protein can be prepared by synthetic standard methods, for example, using an automated DNA synthesizer.

As used herein "introduction" or "to introduce" comprises all methods, including but not limited to as transfection, transduction or transformation, which are suitable for directly or indirectly introducing, into a plant or a cell, compartment, tissue, organ or seed, a nucleic acid sequence, or generating it therein. The introduction may lead to a transient or to a stable presence of a nucleic acid sequence.

One embodiment described herein is the product derived from a plant or photosynthetic organism comprising a nucleic acid molecule, a DNA expression cassette, or a vector comprising the expression cassette, or comprising a cell comprising the nucleic acid molecule, the expression cassette, or the vector, or plant which is tolerant to water stress, obtained by the method comprising using the nucleic acid molecule, a DNA expression cassette, a vector comprising the expression cassette, or a cell comprising the nucleic acid molecule, the expression cassette, or the vector, from a plant or photosynthetic organism producible by the method described herein or from a plant, plant part, transgenic seed, photosynthetic organism or transgenic plant.

Another embodiment provides a method for the production of a product, herewith the method for the production of a product, comprising: a) growing a plant comprising the nucleic acid molecule disclosed herein, a DNA expression cassette as disclosed herein, or a vector comprising the expression cassette, or comprising a cell comprising the nucleic acid molecule, the expression cassette, or the vector or obtainable by the method of the invention; b) producing the product from or by the plant and/or part, or seeds of the plant.

Another embodiment is the method for the production of a product, which comprises: a) growing a plant comprising the nucleic acid molecule, a DNA expression cassette, or a vector comprising the expression cassette, or comprising a cell comprising the nucleic acid molecule, the expression cassette, or the vector or obtainable by the method and removing the plant, plant part, transgenic plant, or transgenic seed; and b) producing the product from or by the plant, plant part, transgenic plant, or transgenic seed of the plant.

As used herein "epitope" is understood as meaning the regions of an antigen which determine the specificity of the antibodies (the antigenic determinant). Accordingly, an epitope is the portion of an antigen which actually comes into contact with the antibody.

Such antigenic determinants are those regions of an antigen to which the T-cell receptors react and, as a consequence, produce antibodies which specifically bind the antigenic determinant/epitope of an antigen. Accordingly, antigens, or their epitopes, are capable of inducing the immune response of an organism with the consequence of the formation of specific antibodies which are directed against the epitope. Epitopes consist for example of linear sequences of amino acids in the primary structure of proteins, or of complex secondary or tertiary protein structures. A hapten is understood as meaning an epitope which is dissociated from the context of the antigen environment. Although haptens have by definition an antibody directed against them, haptens are, under certain circumstances, not capable of inducing an immune response in an organism, for example, after an injection. To this end, haptens are coupled with carrier molecules. An example which may be mentioned is dinitrophenol (DNP), which, after coupling to BSA (bovine serum albumin), has been used for generating antibodies which are directed against DNP (Bohn, A., König, W. (1982), *Immunology* 47 (2), 297).

Haptens are substances (frequently low-molecular weight substances or small substances) which, while they themselves do not trigger immune response, will indeed trigger such a response when coupled to a large molecular carrier. The antibodies generated thus also include those which can bind to the hapten alone.

Another embodiment described herein relates to an antibody against an FMO protein polypeptide as described, in particular to a monoclonal antibody which binds an FMO polypeptide which comprises an amino acid sequence or consists thereof, as shown in the sequences shown in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43.

These antibodies can be used for identifying and isolating polypeptides disclosed in accordance with the invention, from organisms, including plants, such as monocotyledonous plants, as well as dicotyledonous plants. The antibodies can either be monoclonal, polyclonal or synthetic in nature or else consist of antibody fragments such as Fab, Fv or scFv fragments, which are formed by proteolytic degradation. "Single chain" Fv (scFv) fragments are single-chain fragments which, linked via a flexible linker sequence, only comprise the variable regions of the heavy and light antibody chains. Such scFv fragments can also be produced as recombinant antibody derivatives. A presentation of such antibody fragments on the surface of filamentous phages makes possible the direct selection, from combinatory phage libraries, of scFv molecules which bind with high affinity. Monoclonal antibodies can be obtained in accordance with the method described by Köhler and Milstein in *Nature* 256, 495 (1975).

Screening cDNA libraries or genomic libraries of other organisms, including the plant and photosynthetic organisms mentioned herein, which are suitable as transformation hosts, using the nucleic acid sequences described in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; or parts of the same as probe is also a method known to the skilled worker for identifying homologs in other species. In this context, the probes derived from the nucleic acid sequence as shown in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: SEQ ID NO: 39, SEQ ID NO: 41 or SEQ ID NO: 44; have a length of at least 20 bp, or at least 50 bp, or at least 100 bp, or at least 200 bp, or at least 400 bp. The probe can also be one or more kilobases in length, for example, 1 kb, 1.5 kb or 3 kb. A DNA strand which is complementary to the sequences described in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44 or a fragment of same strand with a length of between 20 by and several kilobases may also be employed for screening the libraries.

In an additional embodiment, the FMO protein coding sequences may hybridize under standard conditions with the nucleic acid molecules described by SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; and which code for FMO proteins, with the nucleic acid molecules which are complementary to the above or with parts of the above and which, as complete sequences, code for polypeptides which essentially have identical properties, preferred functional properties, to the polypeptides described in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42 or SEQ ID NO: 43 may also be used.

As used herein "standard hybridization conditions" is to be understood in the broad sense and means, depending on the application, stringent or else less stringent hybridization conditions. Such hybridization conditions are described, inter alia, in Sambrook J, et al. 1989, pages 9.31-9.57 or in *Current Protocols in Molecular Biology*, John Wiley & Sons, N.Y. (1989), 6.3.1-6.3.6. One skilled in the art, based on his technical knowledge, would choose hybridization conditions which allow him to differentiate between specific and unspecific hybridizations.

For example, the conditions during the wash step can be selected from among low-stringency conditions (with approximately 2*SSC at 50° C.) and high-stringency conditions (with approximately 0.2*SSC at 50° C., preferably at 65° C.) (20*SSC: 0.3M sodium citrate, 3M NaCl, pH 7.0). Moreover, the temperature during the wash step can be raised from low-stringency conditions at room temperature, approximately 22° C., to higher-stringency conditions at approximately 65° C. The two parameters, salt concentration and temperature, can be varied simultaneously or else singly, keeping in each case the other parameter constant. During the hybridization, it is also possible to employ denaturant agents such as, for example, formamide or SDS. In the presence of 50% formamide, the hybridization is preferably carried out at 42° C. Some examples of preferred conditions for hybridization and wash step are detailed herein below:

(1) Hybridization conditions can be selected for example, among the following conditions:
 a) 4*SSC at 65° C.,
 b) 6*SSC at 45° C.,
 c) 6*SSC, 100 [mu]g/ml denatured fragmented fish sperm DNA at 68° C.,
 d) 6*SSC, 0.5% SDS, 100 [mu]g/ml denatured salmon sperm DNA at 68° C.,
 e) 6*SSC, 0.5% SDS, 100 [mu]g/ml denatured fragmented salmon sperm DNA, 50% formamide at 42° C.,
 f) 50% formamide, 4*SSC at 42° C.,
 g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C.,
 h) 2* or 4*SSC at 50° C. (low-stringency condition),
 i) 30 to 40% formamide, 2* or 4*SSC at 42° C. (low-stringency condition), or
 j) 500 mN sodium phosphate buffer pH 7.2, 7% SDS (g/V), 1 mM EDTA, 10 [mu]g/ml single stranded DNA, 0.5% BSA (g/V) (see Church and Gilbert, *Proc. Natl. Acad. Sci. U.S.A.* 81:1991 (1984))

(2) Wash steps can be selected for example, among the following conditions:
 a) 0.015 M NaCl/0.0015 M sodium citrate/0.1% SDS at 50° C.,
 b) 0.1*SSC at 65° C.,
 c) 0.1*SSC, 0.5% SDS at 68° C.,
 d) 0.1*SSC, 0.5% SDS, 50% formamide at 42° C.,
 e) 0.2*SSC, 0.1% SDS at 42° C., or
 f) 2*SSC at 65° C. (low-stringency condition).

Other examples of hybridization conditions are selected as follows:

A hybridization buffer comprising formamide, NaCl and PEG 6000 is chosen. The presence of formamide in the hybridization buffer destabilizes double-strand nucleic acid molecules, whereby the hybridization temperature can be lowered to 42° C. without thereby reducing the stringency. The use of salt in the hybridization buffer increases the renaturation rate of a duplex DNA, in other words the hybridization efficiency. Although PEG increases the viscosity of the solution, which has a negative effect on the renaturation rates, the presence of the polymer in the solution increases the concentration of the probe in the remaining medium, which increases the hybridization rate. The composition of the buffer is:

Hybridization buffer:
250 mM sodium phosphate buffer pH 7.2
1 mM EDTA
7% SDS (g/v)
250 mM NaCl
10 [mu]g/ml ssDNA
5% polyethylene glycol (PEG) 6000
40% formamide The hybridizations are carried out for approximately 12 hours at 42° C., for example overnight. The filters are then washed 3* with 2*SSC+0.1% SDS for in each case approximately 10 minutes.

As used herein the "modification" of nucleotide sequences or amino acid sequences comprises mutating them, or mutations. For the purposes described here, "mutations" means the modification of the nucleic acid sequence of a gene variant in a plasmid or in the genome of an organism. Mutations can be generated for example as the consequence of errors during replication, or by mutagens. The spontaneous mutation rate in the cell genome of organisms is very low; however, the skilled person in the art knows a multiplicity of biological, chemical or physical mutagens and methods of mutating nucleotide sequences in a random or targeted manner, and therefore ultimately potentially also for modifying the amino acid sequences which they encode.

Mutations comprise substitutions, additions, deletions of one or more nucleic acid residues. Substitutions are understood as meaning the exchange of individual nucleic acid bases, where one distinguishes between transitions (substitution of a purine base for a purine base, and of a pyrimidine base for a pyrimidine base) and transversions (substitution of a purine base for a pyrimidine base, or vice versa).

Addition or insertion is understood as meaning the incorporation of additional nucleic acid residues in the DNA, which may result in reading-frame shifts. In the case of such reading frame shifts, one distinguishes between in-frame insertions/additions and out-of-frame insertions. In the case of the in-frame insertions/additions, the reading frame is retained, and a polypeptide which is lengthened by the number of the amino acids encoded by the inserted nucleic acids is formed. In the case of out-of-frame insertions/additions, the original reading frame is lost, and the formation of a complete and functional polypeptide is in many cases no longer possible, which of course depends on the site of the mutation.

Deletions describe the loss of one or more base pairs, which likewise leads to in-frame or out-of-frame reading-frame shifts and the consequences which this entails with regard to the formation of an intact protein.

One skilled in the art would be familiar with the mutagenic agents (mutagens) which can be used for generating random or targeted mutations and both the methods and techniques which may be employed. Such methods and mutagens are described for example in van Harten A. M. ("*Mutation breeding: theory and practical applications*", Cambridge University Press, Cambridge, UK (1998)), Friedberg E., Walker G., Siede W. ("*DNA Repair and Mutagenesis*", Blackwell Publishing (1995)), or Sankaranarayanan K., Gentile J. M., Ferguson L. R. ("*Protocols in Mutagenesis*", Elsevier Health Sciences (2000)).

Customary methods and processes of molecular biology such as, for example, the in vitro mutagenesis kit, "LA PCR in vitro Mutagenesis Kit" (Takara Shuzo, Kyoto), or PCR mutagenesis using suitable primers, may be employed for introducing targeted mutations.

As mentioned above, a multiplicity of chemical, physical and biological mutagens exists. Those mentioned herein below are given by way of example, but not by limitation.

Chemical mutagens may be divided according to their mechanism of action. Thus, there are base analogs (for example 5-bromouracil, 2-aminopurine), mono- and bifunctional alkylating agents (for example monofunctional agents such as ethyl methyl sulfonate, dimethyl sulfate, or bifunctional agents such as dichloroethyl sulfite, mitomycin, nitrosoguanidine-dialkyl nitrosamine, N-nitrosoguanidine derivatives) or intercalating substances (for example acridine, ethidium bromide).

Examples of physical mutagens are ionizing radiations. Ionizing radiations are electromagnetic waves or corpuscular radiations which are capable of ionizing molecules, i.e. of removing electrons from them. The ions which remain are in most cases highly reactive so that they, in the event that they are formed in live tissue, are capable of inflicting great damage for example to the DNA and thereby inducing mutations (at low intensity). Examples of ionizing radiations are gamma radiation (photon energy of approximately one mega electron volt MeV), X-ray radiation (photon energy of several or many kilo electron volt keV) or else ultraviolet light (UV light, photon energy of over 3.1 eV). UV light causes the formation of dimers between bases, thymidine dimers are most common, and these give rise to mutations.

Examples of the generation of mutants by treating the seeds with mutagenizing agents may include ethyl methyl sulfonate (EMS) (Birchler, J. A. and Schwartz, D., *Biochem. Genet.* 17 (11-12), 1173 (1979); Hoffmann, G. R., *Mutat. Res.* 75 (1), 63 (1980)) or ionizing radiation there has now been added the use of biological mutagens, for example transposons (for example Tn5, Tn903, Tn916, Tn1000, May B. P. et al., *Proc. Natl. Acad. Sci USA.* 100 (20), 11541 (2003)) or molecular-biological methods such as the mutagenesis by T-DNA insertion (Feldman, K. A., *Plant Journal* 1, 71 (1991), Koncz, C., et al., *Plant Mol. Biol.* 20: 963-76 (1992)).

To generate mutated gene variants, chemical or biological mutagens may be used. Among the chemical agents, it is especially preferred to generate mutants by using EMS (ethyl methyl sulfonate) mutagenesis. Among the generation of mutants using biological mutagens, the T-DNA mutagenesis or the transposon mutagenesis may be used.

Thus, for example, it is also possible to employ polypeptides in the methods described herein, which are obtained as the result of a mutation of a nucleotide sequence such as SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 39, SEQ ID NO: 39, SEQ ID NO: 41 or SEQ ID NO: 44

As used herein the term "recombinant" means for example with regard to a nucleic acid sequence, an expression cassette or a vector comprising the nucleic acid sequence or an organism transformed with the nucleic acid sequence, expression cassette or vector, all those constructs or organisms which are the result of recombinant methods and in which either (a) the FMO protein nucleic acid sequence or (b) a genetic control sequence, for example a promoter, which is operably linked with the FMO protein nucleic acid sequence, or (c) (a) and (b) are not located in their-natural genetic environment or have been modified by recombinant methods, it being possible for the modification to be, for example, a substitution, addition, deletion, or insertion of one or more nucleotide residue(s).

Natural genetic environment means the natural chromosomal locus in the organism of origin, or the presence in a genomic library. In the case of a genomic library, the natural genetic environment of the nucleic acid sequence is preferably retained at least in part. The environment flanks the nucleic acid sequence at least on one side and has a sequence length of at least 50 bp, at least 500 bp, at least 1000 bp, at least 5000 bp. A naturally occurring expression cassette-for example the naturally occurring combination of the FMO protein constitutive promoter with the corresponding FMO protein gene-becomes a recombinant expression cassette when the latter is modified by means of non-natural, synthetic ("artificial") methods such as, for example, mutagenization. Suitable methods have been described (U.S. Pat. No. 5,565, 350; WO 00/15815).

As used herein, the term "transgenic" refers to an organism, e.g., a plant, plant cell, callus, plant tissue, or plant part that exogenously contains the nucleic acid, recombinant construct, vector or expression cassette described herein or a part thereof which is introduced by non-essentially biological processes, preferably by Agrobacteria transformation. The recombinant construct or a part thereof is stably integrated into a chromosome, so that it is passed on to successive generations by clonal propagation, vegetative propagation or sexual propagation.

A transgenic plant, plant cell or tissue for the purposes of the methods and products described here is thus understood as meaning that an exogenous FMO nucleic acid, recombinant construct, vector or expression cassette including one or more FMO nucleic acids is integrated into the genome by means of gene technology.

The term "exogenous" nucleic acid refers to a nucleic acid that has been introduced in a plant by means of gene technology. An "exogenous" nucleic acid can either not occur in a plant in its natural form, be different from the nucleic acid in question as found in a plant in its natural form, or can be identical to a nucleic acid found in a plant in its natural form, but integrated not within its natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the methods and products described herein includes an exogenous FMO nucleic acid integrated at any genetic loci and optionally the plant may also include the endogenous gene within the natural genetic background.

In an embodiment, a method for increasing water stress tolerance in a plant or organism may include increasing the levels of TMAO by increasing the expression of a FMO protein or a functional fragment thereof, or a splice variant thereof in the plant or photosynthetic organism, wherein the FMO protein is encoded by (i) an exogenous nucleic acid having at least 50% identity, at least 60% identity, at least 70% sequence identity, at least 80%, at least 90%, at least 95%, at least 98%, at least 99% sequence identity, or even 100% sequence identity with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; or a splice variant thereof; (ii) an exogenous amino acid encoding a protein having at least 50% identity, at least 60%, at least 70% sequence identity, at least 80%, at least 90%, at least 95%, at least 98%, at least 99% sequence identity, or even 100% sequence identity with SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 39, SEQ ID NO: 41, a functional fragment thereof; the encoded protein confers water stress tolerance relative to control plants; (iii) an exogenous nucleic acid capable of hybridizing under stringent conditions with a complementary sequence of any of the nucleic acids according to (i) or (ii); encoding a FMO protein; wherein the amino acid molecule codes for a polypeptide which has essentially identical properties to the polypeptide described in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 39; SEQ ID NO: 41; the encoded protein confers enhanced water stress tolerance relative to control plants; and/or by (iv) an exogenous nucleic acid encoding the same FMO protein as any of the nucleic acids of (i) to (iii) above, but differing from the nucleic acids of (i) to (iii) above due to the degeneracy of the genetic code is a further embodiment of the invention.

The increase of the water stress tolerance in the plant or photosynthetic organism can also be obtained by manipulating the expression of the plant's own protein, i.e. the endogenous protein, which corresponds to the protein, or of an endogenous nucleotide sequence, which constitutes a sequence, and which may also comprise the 5'- and/or 3'-UTR region. It is, then, an endogenous nucleotide or peptide sequence which mediates an increase of the water stress tolerance or it is an amino acid sequence which codes for such a protein. This manipulation can be achieved by any modification of the sequence, often a mutation, but also for example by a modification of the promoter DNA sequence of the protein-encoding gene. Such a modification, which results in a modified, increased, expression rate of the endogenous gene, can be effected by means of deletion or insertion of DNA sequences. As a rule, a modification of the 5'-UTR region in total and/or of the promoter sequence of endogenous genes will lead to a modification of the expressed amount of the gene and/or the function of the expressed gene or gene product, and therefore also to a modification of the activity which can be detected in the cell or in the plants. The modification of the 5'-UTR region in total and/or of the promoter sequence of the endogenous gene may also lead to a modification of the amount of, and/or the function of, a protein in the cell. Please note that an increase in the expression or function is understood as meaning herein both the activation or enhancement of the expression or function of the endogenous protein, including a de novo expression, increase of protein activity, and an increase or enhancement by expression of a transgenic protein or factor.

Another method of increasing the activity and the content of the endogenous protein may include up-regulate transcription factors which are involved in the transcription of the corresponding endogenous gene, for example by means of overexpression. The means for overexpressing transcription factors are known to the skilled worker and are also disclosed for proteins within the context of the present invention.

Moreover, an increased expression of the endogenous gene as described herein can be achieved by a regulator protein, which is not present in the untransformed organism, interacting with the promoter of these genes. Such a regulator may take the form of a chimeric protein which consists of a DNA binding domain and a transcription activator domain, as described for example in WO 96/06166.

The protein-encoding cDNA (or the mRNA including the UTR sequence(s)) sequence for expression in a cell of a plant or photosynthetic organism that, upon expression of the DNA to RNA and transcription of the RNA to produce an encoded peptide or polypeptide, enhances the ability of the plant or photosynthetic organism or plant cell to withstand an abiotic or biotic stress, or enhances the yield or value of the plant or photosynthetic organism, or a crop or product produced from the plant or photosynthetic organism.

The introduction into a plant or organism of an expression cassette comprising, for example, the FMO protein (SEQ ID NO: 1-44) into a photosynthetic organism or plant cells, plant tissue, plant organs such as chloroplast, parts or seeds thereof can advantageously be carried out using vectors which comprise the expression cassettes. The expression cassette can be introduced into the vector (for example the pROK2 vector, or the pCAMBIA vector) via a suitable restriction cleavage site. The plasmid obtained is first introduced into *E. coli* cells. Correctly transformed *E. coli* cells are selected, cultured, and the recombinant plasmid is obtained using methods with which the skilled worker is familiar. Restriction analysis and sequencing may be used for verifying the cloning step.

The vectors may take the form of, for example, plasmids, cosmids, phages, viruses or else agrobacteria and may be introduced by means of plasmid vectors. Examples of vectors are those which make possible a stable integration of the expression cassette into the host genome.

A variety of methods (Keown et al., *Methods in Enzymology* 185, 527(1990)) are available for the introduction of a desired construct into a plant or organism, which is referred to as transformation (or transduction or transfection). Thus, the DNA or RNA can be introduced for example, directly by means of microinjection or by bombardment with DNA-coated microparticles. Also, it is possible to chemically permeabilize the cell, for example using polyethylene glycol, so that the DNA can reach the cell by diffusion. The DNA can also be introduced into the cell by means of protoplast fusion with other DNA-comprising units such as minicells, cells, lysosomes or liposomes. A further suitable method of introducing DNA is electroporation, where the cells are reversibly permeabilized by means of an electrical pulse. Examples of such methods have been described in Bilang et al., *Gene* 100, 247 (1991); Scheid et al., *Mol. Gen. Genet.* 228, 104 (1991); Guerche et al., *Plant Science* 52, 111 (1987); Neuhause et al., *Theor. Appl. Genet.* 75, 30 (1987); Klein et al., *Nature* 327, 70(1987); Howell et al., *Science* 208, 1265 (1980); Horsch et al., *Science* 227, 1229 (1985); DeBlock et al., *Plant Physiology* 91, 694 (1989); "*Methods for Plant Molecular Biology*" (Weissbach and Weissbach, eds.) Academic Press Inc. (1988); and "*Methods in Plant Molecular Biology*" (Schuler and Zielinski, eds.) Academic Press Inc. (1989).

In plants, the above-described methods for the transformation and regeneration of plants from plant tissue or plant cells are exploited for the purposes of transient or stable transformation. Suitable methods are mainly protoplast transformation by means of polyethylene-glycol-induced DNA uptake, the biolistic method with the gene gun, known as the particle bombardment method, electroporation, the incubation of dry embryos in DNA-comprising solution, and microinjection.

Transformation may also be effected by bacterial infection by means of *Agrobacterium tumefaciens* or *Agrobacterium rhizogenes*. The methods are described for example in Horsch et al. *Science* 225, 1229 (1985).

If agrobacteria are used for transformation, the expression cassette may be integrated into specific plasmids, which may either be a shuttle or intermediate vector or a binary vector. If a Ti or Ri plasmid is used for the transformation, at least the right border, but in most cases both the right and the left border, of the Ti or Ri plasmid T-DNA as flanking region is linked with the expression cassette to be introduced.

Binary vectors are capable of replicating in a variety of organisms including but not limited to *E. coli* and in *agrobacterium*. As a rule, they comprise a selection marker gene and a linker or polylinker flanked by the right and left T-DNA border sequence. They can be transformed directly into *agrobacterium* (Holsters et al., *Mol. Gen. Genet.* 163, 181 (1978)). The selection marker gene, for example the nptII gene, which mediates resistance to kanamycin, permits transformed agrobacteria to be selected. The *agrobacterium* which, in the present case, acts as the host organism should already comprise a helper Ti plasmid with the vir region, which is required for transferring the T-DNA to the plant cell. An *agrobacterium* thus transformed can be used for transforming plant cells. The use of T-DNA for the transformation of plant cells has been studied and described in great detail (EP 120 516; Hoekema, in "The Binary Plant Vector System", *Offsetdrukkerij Kanters B. V.*, Alblasserdam, Chapter V; An et al. *EMBO J.* 4, 277 (1985)). Various binary vectors are known and in some cases commercially available, such as, for example, pBI101.2 or pBIN19 (Clontech Laboratories, Inc. USA).

In the event that DNA or RNA is injected or electroporated into plant cells, the plasmid used need not meet particular requirements. Simple plasmids such as those from the pUC series may be used. If intact plants are to be regenerated from the transformed cells, it is necessary for an additional selection marker gene to be located on the plasmid.

Stably transformed cells, i.e. those which comprise the introduced DNA integrated into the DNA of the host cell, can be distinguished from untransformed cells when a selection marker is constituent of the introduced DNA (McCormick et al, *Plant Cell Reports* 5, 81 (1986)). For example, any gene which is capable of mediating a resistance to antibiotics or herbicides (such as kanamycin, G 418, bleomycin, hygromycin or phosphinothricin) may act as a marker. Transformed cells which express such a marker gene are capable of surviving in the presence of concentrations of a suitable antibiotic or herbicide which destroy an untransformed wildtype. Examples include the bar gene, which mediates resistance to the herbicide phosphinothricin (Rathore et al., *Plant Mol. Biol.* 21 (5), 871 (1993)), the nptII gene, which mediates resistance to kanamycin, the hpt gene, which mediates resistance to hygromycin, or the EPSP gene, which mediates resistance to the herbicide glyphosate. The resulting plants can be bred and hybridized in the customary manner. Two or more generations should be cultivated in order to ensure that the genomic integration is stable and hereditary.

Additional methods may be described in Jones et al. ("Techniques for Gene Transfer", in "*Transgenic Plants*", Vol. 1, *Engineering and Utilization*, edited by Kung S. D. and Wu R., Academic Press, p. 128-143 (1993), and in Potrykus, *Annu. Rev. Plant Physiol. Plant Molec. Biol.* 42, 205 (1991)). It is preferred to clone the construct to be expressed into a vector which is suitable for transforming *Agrobacterium tumefaciens*, for example into pBin 19 (Bevan et al., *Nucl. Acids Res.* 12, 8711 (1984)).

When a transformed plant cell has been generated, an intact plant can be obtained using methods known to one skilled in the art. An example of a starting material used here are callus cultures. The formation of shoot and root from this as yet undifferentiated cell biomass can be induced in a known manner. The plantlets obtained can be planted out and bred.

A person skilled in the art also knows methods for regenerating plant parts and intact plants from plant cells. For example, methods described by Fennell et al., *Plant Cell Rep*, 11, 567 (1992); Stoeger et al., *Plant Cell Rep.* 14, 273 (1995); Jahne et al., *Theor. Appl. Genet.* 89, 525 (1994), are used for this purpose.

The recombinant nucleic acid molecules described herein comprise the following elements in 5'-3' orientation: regulatory sequences of a promoter which is active in plant cells, a DNA sequence in operative linkage therewith, if appropriate, regulatory sequences which, in the plant cell, may act as transcription, termination and/or polyadenylation signals in operable linkage therewith.

In the recombinant expression constructs/expression cassettes, a nucleic acid molecule whose expression (transcription and, if appropriate, translation) generates a FMO protein is in operable linkage with at least one genetic control element (for example a promoter) which ensures overexpression in plants. If the expression construct is to be introduced directly into the plant or photosynthetic organism and the FMO protein generated therein in plants or photosynthetic organisms, then plant-specific genetic control elements (for example promoters) are preferred. However, the FMO protein can also be generated in other organisms or in vitro and then introduced into the plant. In this context, preference is given to all prokaryotic or eukaryotic genetic control elements (for example promoters) which permit the overexpression in the plant selected in each case for the production.

A recombinant vector construct or expression construct/cassette is provided comprising: (i) a nucleic acid having at least 50% identity, at least 60% identity, at least 70% sequence identity, at least 80%, at least 90%, at least 95%, at least 98%, at least 99% sequence identity, or even 100% sequence identity with SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; or a splice variant thereof; (ii) an amino acid coding for a protein having at least 50% identity, at least 60% identity, at least 70% sequence identity, at least 80%, at least 90%, at least 95%, at least 98%, at least 99% sequence identity, or even 100% sequence identity with SEQ ID NOs: 2, 4, 6, 8, 10, 12, 14, 16, 18, 20, 22, 24, 26, 28, 30, 32, 34, 36, 38, 39 or 41; the encoded protein confers enhanced water stress tolerance relative to control plants; (iii) a nucleic acid capable of hybridizing under stringent conditions with a complementary sequence of any of the nucleic acids according to (i) or (ii); encoding an FMO protein; wherein the nucleic acid molecule codes for a polypeptide which has essentially identical properties to the polypeptide described in SEQ ID NOs: 2, 4, 6, 8, 10, 12, 14, 16, 18, 20, 22, 24, 26, 28, 30, 32, 34, 36, 38, 39 or 41; the encoded protein confers enhanced water stress tolerance relative to control plants; and/or (iv) a nucleic acid encoding the same FMO protein as any of the nucleic acids of (i) to (iii) above, but differing from the nucleic acids of (i) to (iii) above due to the degeneracy of the genetic code, operably linked with (b) a promoter and (c) a transcription termination sequence.

Arrangements are those in which the nucleic acid sequence to be expressed recombinantly is positioned after the sequence which acts as the promoter, so that the two sequences are bonded covalently with one another. In this context, it is the distance between the promoter sequence and the nucleic acid sequence to be expressed recombinantly is less than 200 base pairs, or less than 100 base pairs, or less than 50 base pairs.

The generation of a functional linkage and the generation of an expression cassette can be carried out by means of customary recombination and cloning techniques as described for example in Sambrook J. (1989), in Silhavy T. J., Berman M. L. and Enquist L. W. "*Experiments with Gene Fusions*", Cold Spring Harbor Laboratory, Cold Spring Harbor (N.Y.) (1984), in Ausubel F. M. et al., "*Current Protocols in Molecular Biology*", Greene Publishing Assoc. and Wiley Interscience (1987) and in Gelvin et al., in "*Plant Molecular Biology Manual*" (1990). However, it is also possible to position, between the two sequences, further sequences which exert for example the function of a linker with specific restriction enzyme cleavage sites, or of a signal peptide. The insertion of sequences may also lead to the expression of fusion proteins. It is preferred that the expression cassette, consisting of a linkage of promoter and nucleic acid sequence to be expressed, can be present in vector-integrated form and inserted into a plant genome by, for example, transformation.

The method described herein can advantageously be combined with other methods which bring about a pathogen resistance (for example against insects, fungi, bacteria, nematodes and the like), stress tolerance or another improvement of the plant characteristics. Examples are mentioned inter alia in Dunwell J. M., *J. Exp. Bot.* 51, (Spec No) 487 (2000).

The nucleic acid molecules described herein may comprise nucleic acid molecules coding for FMO GS-OX5 proteins from *Arabidopsis* according to the polynucleotides SEQ. ID NO: 1, and the nucleic acid sequences which are complementary thereto as shown in FIG. 4, and the sequences which are derived due to the degeneracy of the genetic code, where the nucleic acid molecules do not consist of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44. The nucleic molecules described herein may comprise nucleic acid molecules coding for FMO GS-OX3 proteins from cucumber plants according to the polynucleotides SEQ ID NOs: 5, 7, 9, 11, and the nucleic acid sequences which are complementary thereto, and the sequences which are derived due to the degeneracy of the genetic code, where the nucleic acid molecules do not consist of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44.

Transgenic expression cassettes may also be developed for the expression of FMO proteins where the cassettes may comprise one of the nucleic acid sequences nucleic acid molecule including but not limited to SEQ ID No: 1 SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; or a fragment thereof. In the transgenic expression cassettes, the nucleic acid sequence coding for the FMO proteins from *Arabidopsis* is linked with at least one genetic control element as defined above in such a manner that the expression (transcription and, if appropriate, translation) can be effected in any organism, usually in dicotyledonous plants. Genetic control elements which are suitable for this purpose are described above. The transgenic expression cassettes may also comprise further functional elements as defined above.

Such expression cassettes may comprise a nucleic acid sequence which is essentially identical to a nucleic acid molecule as shown in SEQ ID No.:1 SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41 or SEQ ID NO: 44; or a fragment thereof, where the nucleic acid sequence is in sense orientation or in antisense orientation relative to a promoter and can therefore lead to the expression of sense or antisense RNA, the promoter being a promoter which is active in plants, usually a promoter which can be induced by pathogen attack. Also provided herein are transgenic vectors which encompass the transgenic expression cassettes.

A promoter is a DNA region, which includes sequences sufficient to cause transcription of an associated (downstream) sequence. The promoter may be regulated, i.e., not constitutively acting to cause transcription of the associated sequence. If inducible, there are sequences present therein which mediate regulation of expression so that the associated sequence is transcribed only when an inducer molecule is present. The promoter may be any DNA sequence which shows transcriptional activity in the chosen plant cells, plant parts, or plants. The promoter may be inducible or constitutive. It may be naturally-occurring, may be composed of portions of various naturally-occurring promoters, or may be partially or totally synthetic. Also, the location of the promoter relative to the transcription start may be optimized. Many suitable promoters for use in plants or photosynthetic organisms are well known in the art, as are nucleotide sequences, which enhance expression of an associated expressible sequence.

A variety of promoters may be used in the methods described herein including a drought-inducible promoter, an epidermis promoter, a mesophyll-specific promoter, or a stress induced promoter (for example RD29 (Singh et al. *Plant Cell Rep* 30:1019-1028(2011)). The promoter may be selected from the group consisting of a promoter induced by: osmotic stress, drought stress, cold stress, heat stress, oxidative stress, nutrient deficiency, infection by a fungus, infection by an oomycete, infection by a virus, infection by a bacterium, nematode infestation, pest infestation, weed infestation, and herbivory.

The promoters can be selected based on the desired outcome. That is, the nucleic acids can be combined with constitutive, tissue-preferred, or other promoters for expression in the host cell of interest. The promoter may be inducible or constitutive. It may be naturally-occurring, may be composed of portions of various naturally occurring promoters, or may be partially or totally synthetic. Guidance for the design of promoters is commonly known in the art. In addition, the location of the promoter relative to the transcription start may be optimized. Many suitable promoters for use in plants are well known in the art, as are nucleotide sequences, which enhance expression of an associated expressible sequence. An example of a DNA construct with a suitable promoter may include a nucleotide sequence in operable linkage with a stress-inducible promoter or an epidermis- and/or mesophyll-specific promoter.

Plant-specific promoters mean in principle any promoter which is capable of controlling the expression of genes, in particular foreign genes, in plants or plant parts, plant cells, plant tissues, plant cultures. Here, the expression can be for example constitutional, inducible or development-dependent.

As used herein "constitutive" promoter means those promoters which ensure overexpression in numerous tissues over a relatively large period of plant development, at all times during plant development. In particular, a plant promoter or a promoter derived from a plant virus with the methods described herein including but not limited to the 35S transcript of the CaMV cauliflower mosaic virus (Franck et al. *Cell* 21, 285 (1980); Odell et al. *Nature* 313, 810 (1985); Shewmaker et al. *Virology* 140, 281 (1985); Gardner et al. *Plant Mol Biol* 6, 221 (1986)) or the 19S CaMV Promoter (U.S. Pat. No. 5,352,606; WO 84/02913; Benfey et al. *EMBO J.* 8, 2195-2202 (1989)). A further suitable constitutive promoter is the rubisco small subunit (SSU) promoter (U.S. Pat. No. 4,962,028), the promoter of *Agrobacterium* nopaline synthase, the TR double promoter, the *Agrobacterium* OCS (octopine synthase) promoter, the ubiquitin promoter (Holtorf S et al. *Plant Mol Biol* 29, 637 (1995)), the ubiquitin 1 promoter (Christensen et al. *Plant Mol Biol* 18, 675 (1992); Bruce et al. *Proc Natl Acad Sci USA* 86, 9692 (1989)), the Smas promoter, the cinnamyl-alcohol dehydrogenase promoter (U.S. Pat. No. 5,683,439), the promoters of vacuolar ATPase subunits or the promoter of a proline-rich protein from wheat (WO 91/13991), and further promoters of genes whose constitutive expression in plants is known to the skilled worker including the promoter of nitrilase-1 (nit1) gene from *A. thaliana* (GenBank Acc.-No.: Y07648.2, Nucleotide 2456-4340, Hillebrand et al. *Gene* 170, 197 (1996)).

Seed-specific promoters are, for example, the promoter of phaseolin (U.S. Pat. No. 5,504,200; Bustos et al. *Plant Cell* 1(9), 839 (1989)), of the 2S albumin gene (Joseffson et al. *J Biol Chem* 262, 12196 (1987)), of legumin (Shirsat et al. *Mol Gen Genet* 215(2), 326 (1989)), of the USP (unknown seed protein; Baumlein et al. *Mol Gen Genet* 225(3), 459 (1991)), of the napin gene (U.S. Pat. No. 5,608,152; Stalberg et al. *L Planta* 199, 515 (1996)), of the gene coding for the sucrose binding protein (WO 00/26388) or the legumin B4 promoter (LeB4; Baumlein et al. *Mol Gen Genet* 225, 121 (1991); Baumlein et al. *Plant Journal* 2(2), 233 (1992); Fiedler et al. *Biotechnology* (NY) 13(10), 1090 (1995)), the oleosin promoter from *Arabidopsis* (WO 98/45461), the Bce4 promoter from *Brassica* (WO 91/13980). Further suitable seed-specific promoters are those of the genes coding for the high molecular weight glutenin (HMWG), gliadin, branching enzyme, ADP glucose pyrophosphatase (AGPase) or starch synthase. Further promoters may include those allowing seed-specific expression in monocotyledons such as maize, barley, wheat, rye, rice etc. It is possible and advantageous to employ the promoter of the Ipt2 or Ipt1 gene (WO 95/15389, WO 95/23230) or the promoters described in WO 99/16890 (promoters of the hordein gene, of the glutelin gene, of the oryzin gene, of the prolamin gene, of the gliadin gene, of the zein gene, of the kasirin gene or of the secalin gene).

Tuber-, storage root- or root-specific promoters are, for example, the patatin class I promoter (B33) or the promoter of the potato cathepsin D inhibitor.

Leaf-specific promoters are, for example, the promoter of the cytosolic FBPase from potato (WO 97/05900), the SSU promoter (small subunit) of the rubisco (ribulose-1.5-bisphosphate carboxylase) or the ST-LSI promoter from potato (Stockhaus et al. *EMBO J.* 8, 2445 (1989)). Epidermis-specific promoters are, for example the promoter of the OXLP gene ("oxalate oxidase like protein"; Wei et al. *Plant Mol. Biol.* 36, 101 (1998)) and a promoter consisting of the GSTA1 promoter and the WIR1a intron (WO 2005/035766) and the GLP4 promoter (WO 2006/1288832 PCT/EP 2006/062747).

Examples of other tissue-specific promoters are: flower-specific promoters, for example the phytoene synthase promoter (WO 92/16635) or the promoter of the Prr gene (WO 98/22593) and anther-specific promoters, for example the 5126 promoter (U.S. Pat. Nos. 5,689,049, 5,689,051), the glob-I promoter and the [gamma]-zein promoter.

The expression cassettes may also comprise a chemically inducible promoter (review article: Gatz et al. *Annu. Rev. Plant Physiol Plant Mol Biol* 48, 89 (1997)) through which expression of the exogenous gene in the plant can be controlled at a particular point in time. Promoters of this type, such as, for example, the PRP1 promoter (Ward et al. *Plant Mol Biol* 22, 361 (1993)), a salicylic acid-inducible promoter (WO 95/19443), a benzenesulfonamide-inducible promoter (EP 0 388 186), a tetracycline-inducible promoter (Gatz et al. *Plant J* 2, 397 (1992)), an abscisic acid-inducible promoter (EP 0 335 528) and an ethanol- or cyclohexanone-inducible promoter (WO 93/21334) can likewise be used.

Pathogen-inducible promoters which make possible an expression only when required (i.e. in the case of attack by pathogens). In one embodiment, the method therefore uses promoters which are active in plants which are pathogen-inducible promoters. Pathogen-inducible promoters comprise the promoters of genes which are induced as a result of pathogen attack, such as, for example, genes of PR proteins, SAR proteins, [beta]-1.3-glucanase, chitinase etc. (for example Redolfi et al. *Neth J Plant Pathol* 89, 245 (1983); Uknes, et al. *Plant Cell* 4, 645 (1992); Van Loon *Plant Mol Viral* 4, 111 (1985); Marineau et al. *Plant Mol Bid* 9, 335 (1987); Matton et al. *Molecular Plant-Microbe Interactions* 2, 325 (1987); Somssich et al. *Proc Natl Acad Sci USA* 83, 2427 (1986); Somssich et al. *Mol Gen Genetics* 2, 93 (1988); Chen et al. *Plant J* 10, 955 (1996); Zhang and Sing *Proc Natl*

*Acad Sci USA* 91, 2507 (1994); Warner, et al. *Plant J* 3, 191 (1993); Siebertz et al. *Plant Cell* 1, 961 (1989)).

An additional promoter for the overexpression of the FMO proteins as described herein may include wounding-inducible promoters such as that of the pinII gene (Ryan *Ann Rev Phytopath* 28, 425 (1990); Duan et al. *Nat Biotech* 14, 494 (1996)), of the wun1 and wun2 gene (U.S. Pat. No. 5,428, 148), of the win1 and win2 gene (Stanford et al. *Mol Gen Genet* 215, 200 (1989)), of the systemin gene (McGurl et al. *Science* 225, 1570 (1992)), of the WIP1 gene (Rohmeier et al. *Plant Mol Biol* 22, 783 (1993); Eckelkamp et al. *FEBS Letters* 323, 73 (1993)), of the MPI gene (Corderok et al. *Plant J* 6(2), 141 (1994)) and the like.

A source of further pathogen-inducible promoters may include the pathogenesis-related (PR) gene family. A series of elements in these promoters have proved advantageous. Thus, the nucleotide region of nucleotide −364 to nucleotide −288 in the promoter of PR-2d mediates salicylate specificity (Buchel et al. *Plant Mol Biol* 30, 493 (1996)). In tobacco, this region binds a nuclear protein whose abundance is increased by salicylate. The PR-1 promoters from tobacco and *Arabidopsis* (EP-A 0 332 104, WO 98/03536) are also suitable as pathogen-inducible promoters. Also useful, since particularly specifically induced by pathogens, are the "acidic PR-5"- (aPR5) promoters from barley (Schweizer et al. *Plant Physiol* 114, 79 (1997)) and wheat (Rebmann et al. *Plant Mol Biol* 16, 329 (1991)). A PR5 proteins accumulate within approximately 4 to 6 hours after attack by pathogens and only show very little background expression (WO 99/66057). One approach for obtaining an increased pathogen-induced specificity is the generation of synthetic promoters from combinations of known pathogen-responsive elements (Rushton et al. *Plant Cell* 14, 749 (2002); WO 00/01830; WO 99/66057). Other pathogen-inducible promoters from different species are known to the skilled worker (EP-A 1 165 794; EP-A 1 062 356; EP-A 1 041 148; EP-A 1 032 684).

Further pathogen-inducible promoters comprise the Flachs Fis1 promoter (WO 96/34949), the Vst1 promoter (Schubert et al. *Plant Mol Biol* 34, 417 (1997)) and the tobacco EAS4 sesquiterpene cyclase promoter (U.S. Pat. No. 6,100,451).

Other promoters are those which are induced by biotic or abiotic stress, such as, for example, the pathogen-inducible promoter of the PRP1 gene (or gst1 promoter), for example from potato (WO 96128561; Ward et al. *Plant Mol Biol* 22, 361 (1993)), the heat-inducible hsp70 or hsp80 promoter from tomato (U.S. Pat. No. 5,187,267), the chill-inducible alpha-amylase promoter from potato (WO 96/12814) and the light-inducible PPDK promoter or the wounding-inducible pinII promoter (EP-A 0 375 091).

In one embodiment, the methods described herein employ mesophyll-tissue-specific promoters such as, for example, the promoter of the wheat germin 9f-3.8 gene (GenBank Acc.-No.: M63224) or the barley GerA promoter (WO 02/057412). The promoters are particularly advantageous since they are both mesophyll-tissue-specific and pathogen-inducible. Also suitable is the mesophyll-tissue-specific *Arabidopsis* CAB-2 promoter (GenBank Acc.-No.: X15222), and the *Zea mays* PPCZm1 promoter (GenBank Acc.-No.: X63869) or homologs thereof. Mesophyll-tissue-specific means that the transcription of a gene is limited to as few as possible plant tissues which comprise the mesophyll tissue as the result of the specific interaction of cis elements present in the promoter sequence and transcription factors binding to these elements; preferably, it means a transcription which is limited to the mesophyll tissue.

Additional mesophyll-specific promoters include PPCZm1 (=PEPC; Kausch, *Plant Mol. Biol.* 45, 1 (2001)); OsrbcS (Kyozuka et al., *Plant Phys.* 102, 991-(1993)); OsP-PDK, acc. AC099041; TaGF-2.8, acc. M63223 (Schweizer, *Plant J.* 20, 541 (1999)); TaFBPase, acc. X53957; TaWIS1, acc. AF467542 (US 20021115849); HvBIS1, acc. AF467539 (US 2002/115849); ZmMIS1, acc. AF467514 (US 2002/115849); HvPR1a, acc. X74939 (Bryngelsson et al., *Molecular Plant-Microbe Interactions* 7 (2), 267 (1994); HvPR1b, acc. X74940 (Bryngelsson et al., *Molecular Plant-Microbe Interactions* 7 (2), 267 (1994)); HvB1.3gluc; acc. AF479647; HvPrx8, acc. AJ276227 (Kristensen et al., *Molecular Plant Pathology* 2 (6), 311(2001)); and HvPAL, acc. X97313 (Wei, *Plant Molecular Biology* 36, 101 (1998)).

Examples of epidermis-specific promoters are, for example, WIR5 (=GstA1), acc. X56012 (Dudler & Schweizer, unpublished); GLP4, acc. AJ310534 (Wei, *Plant Molecular Biology* 36, 101 (1998)); GLP2a, acc. AJ237942 (Schweizer, *Plant J.* 20, 541 (1999).); Prx7, acc. AJ003141 (Kristensen, *Molecular Plant Pathology* 2 (6), 311(2001)); GerA, acc. AF250933 (Wu, *Plant Phys. Biochem.* 38 or 685 (2000)); OsROC1, acc. AP004656; RTBV, acc. AAV62708, AAV62707 (Klöti, PMB 40, 249 (1999)) and Cer3 (Hannoufa, *Plant J.* 10 (3), 459 (1996)).

Examples of additional promoters suitable for the expression of FMO proteins include fruit ripening-specific promoters such as, for example, the fruit ripening-specific promoter from tomato (WO 94/21794, EP 409 625). Development-dependent promoters include some of the tissue-specific promoters because the development of individual tissues naturally takes place in a development-dependent manner.

Constitutive, and leaf- and/or stem-specific, pathogen-inducible, root-specific, mesophyll-tissue-specific promoters may be used with constitutive, pathogen-inducible, mesophyll-tissue-specific and root-specific promoters.

A further possibility for further promoters which make expression possible in further plant tissues or in other organisms such as, for example, *E. coli* bacteria to be operably linked to the nucleic acid sequence to be expressed or overexpressed. All the promoters described above are in principle suitable as plant or photosynthetic organism promoters.

Other promoters which are suitable for expression in plants are described (Rogers et al. *Meth in Enzymol* 153, 253 (1987); Schardl et al. *Gene* 61, 1 (1987); Berger et al. *Proc Natl Acad Sci USA* 86, 8402 (1989)).

Moreover, the average person skilled in the art is capable of isolating further suitable promoters by means of routine methods. Thus, the person skilled in the art can identify for example further epidermis-specific regulatory nucleic acid elements, with the aid of customary methods of molecular biology, for example with hybridization experiments or with DNA-protein binding studies. Here, a first step involves, for example, the isolation of the desired tissue from the desired organism from which the regulatory sequences are to be isolated, wherefrom the total poly(A)+RNA is isolated and a cDNA library is established. In a second step, those clones from the first library whose corresponding poly(A)+RNA molecules only accumulate in the desired tissue are identified by means of hybridization with the aid of cDNA clones which are based on poly(A)+RNA molecules from another tissue. Then, promoters with tissue-specific regulatory elements are isolated with the aid of these cDNAs thus identified. Moreover, a person skilled in the art has available further PCR-based methods for the isolation of suitable tissue-specific promoters.

The nucleic acid sequences present in the expression cassettes or vectors described herein may be operably linked to further genetic control sequences besides a promoter. The term genetic control sequences has a wide meaning and means all sequences which have an influence on the coming into existence or the function of the recombinant nucleic acid molecule of the invention. For example, genetic control sequences modify transcription and translation in prokaryotic or eukaryotic organisms. The expression cassettes may further comprise a promoter with an abovementioned specificity 5'-upstream from the particular nucleic acid sequence which is to be expressed transgenically, and a terminator sequence as additional genetic control sequence 3'-downstream, and if appropriate further conventional regulatory elements, in each case operably linked to the nucleic acid sequence to be expressed transgenically.

Genetic control sequences also comprise further promoters, promoter elements or minimal promoters capable of modifying the expression-controlling properties. It is thus possible for example through genetic control sequences for tissue-specific expression to take place additionally dependent on particular stress factors. Corresponding elements are described, for example, for water stress, abscisic acid (Lam E and Chua N H, *J Biol Chem* 266(26): 17131(1991)) and heat stress (Schoffl F et al., *Molecular & General Genetics* 217(2-3): 246, 1989).

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions (5'-UTR), introns or noncoding 3' region of genes such as, for example, the actin-1 intron, or the Adh1-S introns 1, 2 and 6 (generally: *The Maize Handbook*, Chapter 116, Freeling and Walbot, Eds., Springer, New York (1994)). It has been shown that these may play a significant function in the regulation of gene expression. It has thus been shown that 5'-untranslated sequences are capable of enhancing transient expression of heterologous genes. An example of a translation enhancer which may be mentioned is the 5' leader sequence from the tobacco mosaic virus (Gallie et al. *Nucl Acids Res* 15, 8693 (1987)) and the like. They may in addition promote tissue specificity (Rouster J et al. *Plant J* 15, 435 (1998)). For example, is the natural 5'-UTR of the AtFMO GS-OX5 or ZmFMO gene, however the use of the promoter of the methods described herein induces the expression levels higher, for example drought stress induces an increase of three fold in the expression level, in particular that with the sequence of SEQ ID NO: 1, 25, or a sequence with at least 50%, 60%, 70%, 80%, 90%, 95%, 97% or in particular 99% or more identity thereto. The recombinant nucleic acid molecule may advantageously comprise one or more so-called enhancer sequences in operable linkage with the promoters, which make increased transgenic expression of the nucleic acid sequence possible. Additional advantageous sequences such as further regulatory elements or terminators can also be inserted at the 3' end of the nucleic acid sequences to be expressed recombinantly. The nucleic acid sequences to be expressed recombinantly may be present in one or more copies in the gene construct.

Polyadenylation signals suitable as control sequences are plant polyadenylation signals may include those which correspond essentially to T-DNA polyadenylation signals from *Agrobacterium tumefaciens*, in particular to gene 3 of the T-DNA (octopine synthase) of the Ti plasmid pTiACHS (Gielen et al. *EMBO J* 3:835(1984)) or functional equivalents thereof. Examples of particularly suitable terminator sequences are the OCS (octopine synthase) terminator and the NOS (nopaline synthase) terminator.

Control sequences mean those sequences which make homologous recombination or insertion into the genome of a host organism possible or allow deletion from the genome. In homologous recombination, for example, the natural promoter of a particular gene can be specifically replaced by a promoter with specificity for the embryonal epidermis and/or the flower.

A recombinant nucleic acid molecule and a vector derived from the molecule may comprise further functional elements. The term functional element has a wide meaning and means all elements which have an influence on the production, replication or function of the nucleic acid molecules, the vectors or the transgenic organisms of the invention. Non-restrictive examples which may be mentioned are selection markers which confer a resistance to a metabolism inhibitor such as 2-deoxyglucose 6-phosphate (WO 98/45456), antibiotics or biocides, herbicides, for example kanamycin, G 418, bleomycin, hygromycin or phosphinotricin. Examples which may be mentioned are: DNA sequences which code for phosphinothricin acetyltransferases (PAT), which inactivate glutamine synthase inhibitors (bar and pat gene), 5-enolpyruvylshikimate-3-phosphate synthase (EPSP synthase genes) which confer resistance to Glyphosat(R) (N-(phosphonomethyl)glycine), the gox gene, which codes for the Glyphosat (R)-degrading enzyme (glyphosate oxidoreductase), the deh gene (coding for a dehalogenase which inactivates dalapon), and bxn genes which code for bromoxynil-degrading nitrilase enzymes, the aasa gene, which confers a resistance to the antibiotic spectinomycin, the streptomycin phosphotransferase (SPT) gene, which makes possible a resistance to streptomycin, the neomycin phosphotransferase (NPTII) gene, which confers a resistance to kanamycin or geneticidin, the hygromycin phosphotransferase (HPT) gene, which mediates a resistance to hygromycin, the acetolactate synthase gene (ALS), which mediates a resistance to sulfonylurea herbicides (for example mutated ALS variants with, for example, the S4 and/or Hra mutation), and the acetolactate synthase gene (ALS), which mediates a resistance to imidazolinone herbicides.

Reporter genes or selectable markers are genes which code for easily quantifiable proteins and ensure via an intrinsic color or enzymic activity an assessment of the transformation efficiency or of the location or timing of expression including but not limited to reporter proteins (Schenborn E. and Groskreutz D. *Mol Biotechnol.;* 13(1):29 (1999) such as the green fluorescence protein (GFP) (Sheen et al. *Plant Journal* 8(5): 777 (1995); Haselhoff et al *Proc Natl Acad Sci USA* 94(6): 2122 (1997); Reichel et al. *Proc Natl Acad Sci USA* 93(12): 5888 (1996); Tian et al. *Plant Cell Rep* 16:267 (1997); WO 97/41228; Chui et al. *Curr Biol* 6:325 (1996); Leffel et al. *Biotechniques.* 23(5):912-8 (1997)), the chloramphenicoltransferase, a luciferase (Ow et al. *Science* 234:856 (1986); Millar et al. *Plant Mol Biol Rep* 10:324 (1992)), the aequorin gene (Prasher et al. *Biochem Biophys Res Commun* 126(3): 1259 (1985)), the [beta]-galactosidase, R-locus gene (codes for a protein which regulates the production of anthocyanin pigments (red coloration) in plant tissue and thus makes possible the direct analysis of the promoter activity without the addition of additional adjuvants or chromogenic substrates; Dellaporta et al., In: *Chromosome Structure and Function: Impact of New Concepts,* 18*th Stadler Genetics Symposium,* 11:263, (1988), with [beta]-glucuronidase (Jefferson et al., EMBO J., 6, 3901, 1987).

Origins of replication (ORI) which ensure replication of the expression cassettes or vectors may include for example *E. coli*. Examples which may be mentioned are ORI (origin of DNA replication), the pBR322 on or the P15A ori (Sambrook et al.: 1989).

Elements which are necessary for *agrobacterium*-mediated plant transformation, such as, for example, the right or left border of the T-DNA or the vir region.

To select successfully transformed cells, it is generally required to introduce a selection or selectable marker which confers to the successfully transformed cells a resistance to a biocide (for example a herbicide), a metabolism inhibitor such as 2-deoxyglucose 6-phosphate (WO 98/45456) or an antibiotic. The selection marker permits the selection of the transformed cells from untransformed cells (McCormick et al. *Plant Cell Reports* 5:81 (1969)).

An additional embodiment of the present disclosure relates to plants which, as the result of natural processes or artificial induction, comprise one or more mutations in a nucleic acid molecule which comprises the nucleic acid sequence as shown in SEQ ID NOs: 1, 3, 5, 7, 9, 11, 13, 15, 17, 19, 21, 23, 25, 27, 29, 31, 33, 35, 37, 39, 41 or 44, where the mutation brings about an increase of the activity, function or polypeptide quantity of one of the polypeptide encoded by the nucleic acid molecules as shown in SEQ ID NOs: 1, 3, 5, 7, 9, 11, 13, 15, 17, 19, 21, 23, 25, 27, 29, 31, 33, 35, 37, 39, 41 or 44. For example a mutation generated, and identified, by TILLING.

As a consequence, another embodiment may include a plant comprising a nucleic acid sequence which comprises a mutation which brings about, in the plants or parts thereof, an increase of the activity of one of the proteins encoded by the nucleic acid molecules of the invention. For example, the mutation concerns one or more amino acid residues which are identified in the consensus sequence in the figures as being conserved or highly conserved.

Consequently, an embodiment described herein provides a transgenic plant, transgenic plant part, or transgenic plant cell overexpressing an exogenous FMO, including the FMO protein overexpressed in the plant, plant part or plant cell is encoded by (i) an exogenous nucleic acid having at least 50% identity with SEQ ID NOs: 1, 3, 5, 7, 9, 11, 13, 15, 17, 19, 21, 23, 25, 27, 29, 31, 33, 35, 37 or 40, or a splice variant thereof; or by (ii) an exogenous amino acid encoding a protein having at least 50% identity with SEQ ID NOs: 2, 4, 6, 8, 10, 12, 14, 16, 18, 20, 22, 24, 26, 28, 30, 32, 34, 36, 38, 40 or 42, the encoded protein confers enhanced water stress tolerance relative to control plants; (iii) an exogenous nucleic acid capable of hybridizing under stringent conditions with a complementary sequence of any of the nucleic acids according to (i) or (ii); encoding a FMO protein; wherein the amino acid molecule codes for a polypeptide which has essentially identical properties to the polypeptide described in SEQ ID NO: 2, 4, 6, 8, 10, 12, 14, 16, 18, 20, 22, 24, 26, 28, 30, 32, 34, 36, 38, 40 or 42; the encoded protein confers enhanced water stress tolerance relative to control plants; and/or by (iv) an exogenous nucleic acid encoding the same FMO protein as any of the nucleic acids of (i) to (iii) above, but differing from the nucleic acids of (i) to (iii) above due to the degeneracy of the genetic code.

Also provided herein are transgenic plants transformed with at least a) a nucleic acid sequence which comprises the nucleic acid molecules as shown in SEQ ID NOs: 1, 3, 5, 7, 9, 11, 13, 15, 17, 19, 21, 23, 25, 27, 29, 31, 33, 35, 37, 39, 41 or 44; the nucleic acid sequences which are complementary thereto, or the amino acid molecules which code for the polypeptides as shown in SEQ ID NOs: 2, 4, 6, 8, 10, 12, 14, 16, 18, 20, 22, 24, 26, 28, 30, 32, 34, 36, 38, 40, 42 or 43; b) a transgenic expression cassette which comprises one of the nucleic acid sequences, or a vector, and cells, cell cultures, tissue, parts-such as for example leaves, roots and the like or propagation material in the case of plant organisms-derived from such organisms. Of note, this embodiment may also include a plant other than *Arabidopsis thaliana*.

Host organisms or starting organisms, herein "transgenic organisms" are plants as defined above. In one embodiment, the transgenic organism is a mature plant, seed, shoot and seedling, and parts, propagation material and cultures derived therefrom, for example cell cultures. As used herein "mature plant" means plants at any developmental stage beyond the seedling stage. "Seedling" means a young immature plant in an early developmental stage. Plants which are particularly preferred as host organisms are plants to which the method for obtaining a water stress tolerance in accordance with the abovementioned criteria can be applied. In one embodiment, the plant is a dicotyledonous plant as discussed above. In another embodiment of the present disclosure, the plant is a monocotyledonous plant as discussed above. The transgenic organisms can be generated with the above-described methods for the transformation or transfection of organisms.

Further embodiments described herein include the use of the transgenic organisms and of the cells, cell cultures, parts-such as, for example, roots, leaves and the like in the case of transgenic plant organisms, and transgenic propagation material such as seeds or fruits for the preparation of foodstuffs or feeding stuffs, pharmaceuticals or fine chemicals. Stack varieties are also included in which a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content are combined.

Parts of the transgenic plant are also provided herein and comprise the FMO nucleic acid or FMO protein. The may be seeds, roots, leaves and/or flowers comprising the FMO nucleic acid or FMO protein or parts thereof. Preferred parts of soy plants are soy beans comprising the FMO nucleic acid or FMO protein. Products derived from transgenic plants as described herein, parts thereof or harvestable parts thereof are also provided, including meal or oil, such as soybean meal or soybean oil, comprising the FMO nucleic acid or FMO protein. One embodiment is the method for the production of a product, wherein the product is meal or oil, preferably, soybean meal or soybean oil.

In one embodiment described herein, the method for the production of a product comprise: a) growing the plants described herein or obtainable by the methods of described herein and b) producing the product from or by the plants of the invention and/or parts, e.g. seeds, of these plants.

In another embodiment the products produced by the methods described herein are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In a further embodiment the method comprises the steps a) growing the plants of the invention, b) removing the harvestable parts as defined above from the plants and c) producing the product from or by the parts of the transgenic plant or organism.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In another embodiment the methods for the production are used to make agricultural products such as, but not limited to, plant extracts, proteins, amino acids, carbohydrates, fats, oils, polymers, vitamins, and the like. Please note that it is possible that a plant product consists of one or more agricultural products to a large extent.

The transgenic plants produced as described herein may be crossed with similar transgenic plants or with transgenic plants lacking the nucleic acids of the invention or with non-transgenic plants, using known methods of plant breeding, to prepare seeds. Further, the transgenic plant cells or plants described herein may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the FMO nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Therefore another embodiment may include a method for breeding a water stress tolerant plant comprising the steps of: (a) crossing a transgenic plant described herein or a plant obtainable by a method described herein with a second plant; (b) obtaining a seed or seeds resulting from the crossing step described in (a); (c) planting the seed or seeds and growing the seed or seeds to plants; and (d) selecting from the plants the plants expressing a FMO protein, encoded by (i) an exogenous nucleic acid having at least 60% identity with SEQ ID NOs: 1, 3, 5, 7, 9, 11, 13, 15, 17, 19, 21, 23, 25, 27, 29, 31, 33, 35, 37, 39, 41 or 44, or a splice variant thereof; (ii) an exogenous nucleic acid encoding a protein having at least 60% identity with SEQ ID NOs: 2, 4, 6, 8, 10, 12, 14, 16, 18, 20, 22, 24, 26, 28, 30, 32, 34, 36, 38, 40, 42 or 43; the encoded protein confers enhanced water tolerance relative to control plants; (iii) an exogenous nucleic acid capable of hybridizing under stringent conditions with a complementary sequence of any of the nucleic acids according to (i) or (ii); encoding a FMO protein; wherein the nucleic acid molecule codes for a polypeptide which has essentially identical properties to the polypeptide described in SEQ ID NOs: 2, 4, 6, 8, 10, 12, 14, 16, 18, 20, 22, 24, 26, 28, 30, 32, 34, 36, 38, 40, 42 or 43; preferably the encoded protein confers enhanced water stress tolerance relative to control plants; and/or by (iv) an exogenous nucleic acid encoding the same FMO protein as any of the nucleic acids of (i) to (iii) above, but differing from the nucleic acids of (i) to (iii) above due to the degeneracy of the genetic code.

Another embodiment provided herein is a method for plant improvement comprising (a) obtaining a transgenic plant by any of the methods of the present invention; (b) combining within one plant cell the genetic material of at least one plant cell of the plant of (a) with the genetic material of at least one cell differing in one or more gene from the plant cells of the plants of (a) or crossing the transgenic plant of (a) with a second plant; (c) obtaining seed from at least one plant generated from the one plant cell of (b) or the plant of the cross of step (b); (d) planting the seeds and growing the seeds to plants; and (e) selecting from the plants, plants expressing the nucleic acid encoding the FMO GS-OX5 protein; and optionally (f) producing propagation material from the plants expressing the nucleic acid encoding the FMO GS-OX5 protein. The transgenic plants may be selected by known methods as described above (e.g., by screening for the presence of one or more markers which are encoded by plant-expressible genes co-transferred with the FMO gene or screening for the FMO nucleic acid itself), the expression of a structural gene can, of course, also be effected, or influenced, independently of the embodiment of the methods described herein or the use of the subject matter described herein.

The practice described herein employs, unless otherwise indicated, conventional techniques of chemistry, molecular biology, microbiology, recombinant DNA, genetics, immunology, cell biology, cell culture and transgenic biology, which are within the skill of the art. (See, e.g., Maniatis, et al., *Molecular Cloning*, Cold Spring Harbor Laboratory Press, Cold Spring Harbor, N.Y. (1982); Sambrook, et al., (1989); Sambrook and Russell, *Molecular Cloning*, 3rd Ed., Cold Spring Harbor Laboratory Press, Cold Spring Harbor, N.Y. (2001); Ausubel, et al., *Current Protocols in Molecular Biology*, John Wiley & Sons (including periodic updates) (1992); Glover, *DNA Cloning*, IRL Press, Oxford (1985); Russell, *Molecular biology of plants: a laboratory course manual*, Cold Spring Harbor Laboratory Press, Cold Spring Harbor, N.Y. (1984); Anand, *Techniques for the Analysis of Complex Genomes*, Academic Press, NY (1992); Guthrie and Fink, *Guide to Yeast Genetics and Molecular Biology*, Academic Press, NY (1991); Harlow and Lane, *Antibodies*, Cold Spring Harbor Laboratory Press, Cold Spring Harbor, N.Y. (1988); *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, A. R. Liss, Inc. (1987); *Immobilized Cells And Enzymes*, IRL Press (1986); B. Perbal, *A Practical Guide To Molecular Cloning* (1984); the treatise, *Methods In Enzymology*, Academic Press, Inc., NY); *Methods In Enzymology*, Vols. 154 and 155, Wu, et al., eds.; *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds. (1986); Riott, Essential Immunology, 6th Edition, Blackwell Scientific Publications, Oxford (1988); Fire, et al., *RNA Interference Technology: From Basic Science to Drug Development*, Cambridge University Press, Cambridge (2005); Schepers, *RNA Interference in Practice*, Wiley VCH (2005); Engelke, RNA Interference (RNAi): *The Nuts & Bolts of siRNA Technology*, DNA Press (2003); Gott, *RNA Interference, Editing, and Modification: Methods and Protocols (Methods in Molecular Biology)*, Human Press, Totowa, N.J. (2004); and Sohail, *Gene Silencing by RNA Interference: Technology and Application*, CRC (2004)).

EXAMPLES

The following examples are provided to illustrate further the various applications and are not intended to limit the invention beyond the limitations set forth in the appended claims.

1. General Methods
a. Biological Material and Growth Conditions

For the FMO protein overexpression, transgenic *Arabidopsis* plants over expressing the FMO GS-OX5 gene (SEQ ID NO: 1 or SEQ ID NO:2) and described as RCI5-OE (ES 2347399B1) (FMOX3 and FMOX8 genotypes shown in FIG. 1) and wild type (Col-0) seeds of *Arabidopsis thaliana* were obtained using the following method.

RCI5 cDNA was ligated into the SmaI site, downstream of the CaMv35S promoter in the pROK2 vector (Baulcombe et al., 1986) (shown in the construct of FIG. 2a), to obtain the X3 and X8. Once the presence of the construct (such as the construct described in FIG. 2a and FIG. 2b) was verified in the recombinant plasmid by DNA sequencing, were introduced into the *Agrobacterium tumefaciens* strain C58C1 (Deblaere et al., 1985). Transformation of *Arabidopsis* Col was performed following the floral dip method (Clough and Bent, 1998). The plants were sown in plastic pots containing the same amount of water saturated substrate. Trays containing 16 pots with 5 plants per pot were placed in a grow chamber under short-day light conditions until the plants developed 12 leaves. Then, the trays were transferred to the greenhouse under long-day light conditions and the pots were individually placed in transparent plastic glasses in order to avoid water spillage during irrigations. Normal irrigated plants for each genotype were also placed on the trays, as controls. A total of 4 trays were used, with differently distributed genotypes within each tray. No phenotypic differences were observed among genotypes.

In order to determine the plant biomass analysis, *Arabidopsis* plants were grown for three (3) weeks under short day (10 hours light, 14 hours dark, 21° C. light and 20° C. at night, 65% humidity) conditions. Fresh weight from individual rosettes was obtained, Col-0 (n=10) and RCI5-OE (ES 2347399B1) (FMOX3 and FMOX8 genotypes) two weeks after sowing (n=10). Seeds yield of fully grown plants that were grown for 3 weeks under short day conditions and then transferred for 3 additional weeks to long day conditions was recorded. Seeds were harvested 4 weeks later from individual plants (n=10).

b. Nuclear Magnetic Resonance Spectroscopy (NMR)

TMAO content in plants was determined by harvesting three leaves per treatment and freezing them in liquid nitrogen before the NMR determination. At least three independent plants were treated per experiment.

Example 1

TMAO accumulates in pepper and barley after 1 week drought treatment. 'Murano' pepper and 'Bomi' barley seeds were sown and grown as described above. Control plants (six weeks old) were irrigated with 40 ml of water twice in the week, while "drought" treated plants were not irrigated. Leaves were harvested and TMAO was determined by NMR as described. As shown in Table 1, TMAO levels increase almost three fold compared to the control in both pepper and barley after drought treatment.

TABLE 1

| TMAO accumulation after 1 week drought | | | |
|---|---|---|---|
| Crop | TMAO (uM) | SD | % Control |
| Pepper Control | 446.68 | 215.86 | 100 |
| Pepper Drought 7 days | 1224.23 | 243.10 | 274 |
| Barley Control | 422.10 | 43.36 | 100 |
| Barley Drought 7 days | 1252.73 | 251.99 | 297 |

Example 2

As shown in Table 2 and Table 3 below, over-expression of FMO GS-OX5 increasing endogenous production of TMAO di-hydrate does not have trade-offs in *Arabidopsis*. Plant biomass and seed yield was determined in transgenic (X3 and X8 genotypes) and wild type (Col-0) seeds of *Arabidopsis thaliana* were sown, grown and treated as described above in order to evaluate the trade-off costs of the increase of the TMAO endogenous production with no water stress. However, as shown in Tables 2 and 3, no significant difference was observed in the plant biomass or seed weight or yield. The vegetative mean weight increased with the number of copies of the FMO GS-OX5, being significantly larger when 8 copies of the gene are present compared to the 3 copies genotype. The seed mean weight increased with the number of copies of the FMO GS-OX5, being larger when 8 copies of the gene are present compared to the 3 copies genotype.

TABLE 2

Plant Biomass was evaluated as average weight value (in grams) ± S.E. for three different groups of plants grown under no stress conditions: wild type (Col-0) and transgenic (X3 and X8) plants of *Arabidopsis thaliana*.

| Genotype | N | BIOMASS MEAN WEIGHT VALUE ± S.E | ANOVA P-value |
|---|---|---|---|
| Col-0 | 10 | 2.0637 ± 0.2240 | |
| RCI5-OE.FMOX3 | 10 | 1.9199 ± 0.1383 | 0.5917 |
| RCI5-OE.FMOX8 | 10 | 2.5815 ± 0.1191 | 0.023* |

TABLE 3

Plant seed weight or yield was evaluated as average weight value (in mg) ± S.E. for three different groups of seeds and siliques from *Arabidopsis* plants grown under no stress conditions: wild type (Col-0) and transgenic (38.3 and 38.8) plants of *Arabidopsis thaliana*.

| Genotype | N | SEED MEAN WEIGHT VALUE ± S.E | ANOVA P-value |
|---|---|---|---|
| Col-0 | 10 | 522.8 ± 22.64 | |
| RCI5-OE.FMOX3 | 10 | 495.1 ± 37.22 | 0.5330 |
| RCI5-OE.FMOX 8 | 10 | 546.3 ± 35.09 | 0.5806 |

Example 3

As shown in Table 4 below, over-expression of FMO GS-OX5 increases plant survival in *Arabidopsis* under limited water irrigation: Control plants (six weeks old) were irrigated with 40 ml of water twice in the week, while "limited water irrigation" treated plants were irrigated with 30 ml of water once a week. Transgenic (X3 and X8 genotypes) and wild type (Col-0) seeds of *Arabidopsis thaliana* were sown, grown and treated as described. The fitness value increased with the number of copies of the FMO GS-OX5, being larger when 8 copies of the gene are present compared to the 3 copies genotype. Fitness values were assigned using the following criteria: 0: Dead plant; 1: Critically damaged plant symptoms; 2: Moderate damaged plant symptoms; 3: Slightly damaged plant symptoms; 4: Healthy plant. As shown in Table 4, the transgenic plants had a significantly higher fitness value than the non-transgenic plants.

TABLE 4

Average fitness value ± S.E. for three different genotypes grown under limited water irrigation: wild type (Col-0) and transgenic (X3 and X8) plants of *Arabidopsis thaliana*.

| GENOTYPE | NUMBER OF PLANTS | FITNESS VALUE | ANOVA P-value |
|---|---|---|---|
| Col-0 | 60 | 1.75 ± 0.09 | — |
| RCI5-OE.FMOX3 | 60 | 2.533 ± 0.09 | 0.0000* |
| RCI5-OE.FMOX8 | 60 | 3.066 ± 0.09 | 0.0000* |

Example 4

Over-expression of FMO GS-OX5 increases plant survival in *Arabidopsis* under drought conditions: Control plants (six weeks old) were irrigated with 40 ml of water twice in the week; while "drought" treated plants were not irrigated until all the plants were wilted. (TMAO dihydrate applied exogenously is able to recover plant survival in wild type drought stressed plants. Transgenic (FMOX3 and FMOX8 genotypes) and wild type (Col-0) seeds of *Arabidopsis thaliana* were sown, grown and treated as described. After the first cycle of wilting wild type plants were sprayed with 1 g/L TMAO di-hydrate to determine if the wilted wild type plants could recover and perform as well as the transgenic plants in the following cycles of wilting with the exogenous application. Fitness values were assigned using the following criteria: 0: Dead plant; 1: Critically damaged plant symptoms; 2: Moderate damaged plant symptoms; 3: Slightly damaged plant symptoms; 4: Healthy plant. As shown in Table 5, the transgenic plants treated with TMAO had a significantly higher fitness value than the non-transgenic plants treated with TMAO.

TABLE 5

Average fitness value ± S.E. for three different genotypes grown under drought conditions: wild type (Col-0) and transgenic (X3 and X8) plants of *Arabidopsis thaliana*.

| GENOTYPE | NUMBER OF PLANTS | MEAN FITNESS VALUE ± S.E. | ANOVA P-value |
|---|---|---|---|
| Col-0 | 36 | 1.14 ± 0.17 | — |
| Col-0 + 1 g/L SPRAYED TMAO dihydrate SOLUTION | 36 | 1.83 ± 0.21 | 0.0129* |
| RCI5-OE.FMOX3 | 36 | 2.67 ± 0.08 | 0.0000* |
| RCI5-OE.FMOX8 | 36 | 2.64 ± 0.08 | 0.0000* |

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions, and sub-combinations as are within their true spirit and scope.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

What is claimed is:

1. A method of producing a transgenic drought tolerant plant, plant cell, or plant tissue, wherein the method comprises transforming a plant, plant cell, or a plant tissue with a nucleic acid sequence encoding an FMO protein comprising SEQ ID NO: 2 operably linked to a promoter, and selecting a transgenic plant, plant cell, or plant tissue having said sequence stably integrated into said plant's genome, wherein said selecting comprises determining the number of copies of said nucleic acid sequence and selecting a plant having three or eight copies of said nucleic acid sequence integrated into the plant's genome.

2. The method of claim 1, wherein the promoter is a constitutive promoter.

3. The method of claim 1, wherein the promoter is a stress inducible promoter.

4. The method of claim 3, wherein said stress inducible promoter is induced by drought stress.

5. A method for producing a transgenic drought tolerant plant, plant cell, or plant tissue, wherein the method comprises transforming a plant, plant cell, or plant tissue with a nucleic acid sequence encoding an FMO protein operably linked to a promoter, wherein said nucleic acid sequence comprises SEQ ID NO: 1, and selecting a transgenic plant, plant cell, or plant tissue having said sequence stably integrated into said plant's genome, wherein said selecting comprises determining the number of copies of SEQ ID NO: 1 integrated into the plant's genome and selecting a plant having three or eight copies of said nucleic acid sequence integrated into the plant's genome.

6. The method of claim 5, wherein said sequence and promoter are stably integrated into said plant's nuclear genome or chloroplast genome.

7. The method of claim 5, wherein the promoter is a constitutive promoter.

8. The method of claim 5, wherein the promoter is a stress inducible promoter.

9. The method of claim 8, wherein said stress inducible promoter is induced by drought stress.

10. The method of claim 1, wherein said sequence and promoter are stably integrated into said plant's nuclear genome or chloroplast genome.

11. A method for producing a transgenic plant having increased biomass under non-stressed conditions as compared to wild type comprising transforming a plant, plant cell, or a plant tissue with a nucleic acid sequence comprising SEQ ID NO: 1 or a nucleic acid sequence encoding SEQ ID NO: 2 operably linked to a promoter, and selecting a transgenic plant, plant cell, or plant tissue having said sequence stably integrated into said plant's genome, wherein said selecting comprises determining the number of copies of said nucleic acid sequence and selecting a plant for eight copies of said nucleic acid sequence integrated into said plant's genome and, producing a transgenic plant having increased biomass under non-stressed conditions compared to wild type.

12. The method of claim 11, wherein said transgenic plant has an increase in seed weight or yield.

* * * * *

SEQUENCE LISTING

```
<160> NUMBER OF SEQ ID NOS: 44

<210> SEQ ID NO 1
<211> LENGTH: 1380
<212> TYPE: DNA
<213> ORGANISM: Arabidopsis thaliana

<400> SEQUENCE: 1
atggcaccag cacgaacccg agtcaactca ctcaacgtgg cagtgatcgg agccggagcc      60
gccggactcg tagctgcaag agagctccgc cgcgagaatc acaccgtcgt cgttttcgaa     120
cgtgactcaa aagtcggagg tctctgggta tacacaccta acagcgaacc agacccgctt     180
agcctcgatc caaaccgaac catcgtccat tcaagcgtct atgattctct ccgaaccaat     240
ctcccacgag agtgcatggg ttacagagac ttccccttcg tgcctcgacc tgaagatgac     300
gaatcaagag actcgagaag gtaccctagt cacagagaag ttcttgctta cctttgaagac    360 ttcgctagag aattcaaact tgtggagatg gttcgattta agaccgaagt agttcttgtc     420
gagcctgaag ataagaaatg gagggttcaa tccaaaaatt cagatgggat ctccaaagat     480
gagatctttg atgctgttgt tgtttgtaat ggacattata cagaacctag agttgctcat     540
gttcctggta tagattcatg gccagggaag cagattcata gccacaatta ccgtgttcct     600
gatcaattca aagaccaggt ggtggtagtg ataggaaatt ttgcgagtgg agctgatatc     660
agcagggaca taacgggagt ggctaaagaa gtccatatcg cgtctagatc gaatccatct     720
```

```
aagacatact caaaacttcc cgggtcaaac aatctatggc ttcactctat gatagaaagt    780
gtacacgaag atgggacgat tgtttttcag aacggtaagg ttgtacaagc tgataccatt    840
gtgcattgca ctggttacaa atatcacttc ccatttctca acaccaatgg ctatattact    900
gttgaggata actgtgttgg accgctttac gaacatgtct ttccgcctgc gcttgctccc    960
gggctttcct tcatcggttt accctggatg acactgcaat tctttatgtt tgagctccaa   1020
agcaagtggg tggctgcagc tttgtctggc cgggtcacac ttccttcaga agagaaaatg   1080
atggaagacg ttaccgccta ctatgcaaag cgtgaggctt cgggcaacc taagagatac    1140 acacatcgac ttggtggagg tcaggttgat taccttaatt ggatagcaga gcaaattggt   1200
gcaccgcccg gtgaacaatg gagatatcag gaaataaatg gcggatacta cagacttgct   1260
acacaatcag acacttttcc gtataagtgg gacgatgatc atctcatagt tgaggcttat   1320
gaggatttct tgagacagaa gctgattagt agtcttcctt ctcagttatt ggaatcttga   1380
```

<210> SEQ ID NO 2
<211> LENGTH: 459
<212> TYPE: PRT
<213> ORGANISM: Arabidopsis thaliana

<400> SEQUENCE: 2

```
Met Ala Pro Ala Arg Thr Arg Val Asn Ser Leu Asn Val Ala Val Ile
 1               5                  10                  15

Gly Ala Gly Ala Ala Gly Leu Val Ala Ala Arg Glu Leu Arg Arg Glu
            20                  25                  30

Asn His Thr Val Val Phe Glu Arg Asp Ser Lys Val Gly Gly Leu
        35                  40                  45

Trp Val Tyr Thr Pro Asn Ser Glu Pro Asp Pro Leu Ser Leu Asp Pro
    50                  55                  60

Asn Arg Thr Ile Val His Ser Ser Val Tyr Asp Ser Leu Arg Thr Asn
65                  70                  75                  80

Leu Pro Arg Glu Cys Met Gly Tyr Arg Asp Phe Pro Phe Val Pro Arg
                85                  90                  95

Pro Glu Asp Asp Glu Ser Arg Asp Ser Arg Arg Tyr Pro Ser His Arg
            100                 105                 110

Glu Val Leu Ala Tyr Leu Glu Asp Phe Ala Arg Glu Phe Lys Leu Val
        115                 120                 125

Glu Met Val Arg Phe Lys Thr Glu Val Val Leu Val Glu Pro Glu Asp
    130                 135                 140

Lys Lys Trp Arg Val Gln Ser Lys Asn Ser Asp Gly Ile Ser Lys Asp
145                 150                 155                 160

Glu Ile Phe Asp Ala Val Val Val Cys Asn Gly His Tyr Thr Glu Pro
                165                 170                 175

Arg Val Ala His Val Pro Gly Ile Asp Ser Trp Pro Gly Lys Gln Ile
            180                 185                 190

His Ser His Asn Tyr Arg Val Pro Asp Gln Phe Lys Asp Gln Val Val
        195                 200                 205

Val Val Ile Gly Asn Phe Ala Ser Gly Ala Asp Ile Ser Arg Asp Ile
    210                 215                 220

Thr Gly Val Ala Lys Glu Val His Ile Ala Ser Arg Ser Asn Pro Ser
225                 230                 235                 240

Lys Thr Tyr Ser Lys Leu Pro Gly Ser Asn Asn Leu Trp Leu His Ser
                245                 250                 255
```

Met Ile Glu Ser Val His Glu Asp Gly Thr Ile Val Phe Gln Asn Gly
            260                 265                 270

Lys Val Val Gln Ala Asp Thr Ile Val His Cys Thr Gly Tyr Lys Tyr
        275                 280                 285

His Phe Pro Phe Leu Asn Thr Asn Gly Tyr Ile Thr Val Glu Asp Asn
    290                 295                 300

Cys Val Gly Pro Leu Tyr Glu His Val Phe Pro Ala Leu Ala Pro
305                 310                 315                 320

Gly Leu Ser Phe Ile Gly Leu Pro Trp Met Thr Leu Gln Phe Phe Met
                325                 330                 335

Phe Glu Leu Gln Ser Lys Trp Val Ala Ala Leu Ser Gly Arg Val
            340                 345                 350

Thr Leu Pro Ser Glu Glu Lys Met Met Glu Asp Val Thr Ala Tyr Tyr
        355                 360                 365

Ala Lys Arg Glu Ala Phe Gly Gln Pro Lys Arg Tyr Thr His Arg Leu
    370                 375                 380

Gly Gly Gly Gln Val Asp Tyr Leu Asn Trp Ile Ala Glu Gln Ile Gly
385                 390                 395                 400

Ala Pro Pro Gly Glu Gln Trp Arg Tyr Gln Glu Ile Asn Gly Gly Tyr
                405                 410                 415

Tyr Arg Leu Ala Thr Gln Ser Asp Thr Phe Arg Asp Lys Trp Asp Asp
            420                 425                 430

Asp His Leu Ile Val Glu Ala Tyr Glu Asp Phe Leu Arg Gln Lys Leu
        435                 440                 445

Ile Ser Ser Leu Pro Ser Gln Leu Leu Glu Ser
    450                 455

<210> SEQ ID NO 3
<211> LENGTH: 1552
<212> TYPE: DNA
<213> ORGANISM: Brassica rapa

<400> SEQUENCE: 3
gcacgaggca aaaaacaaa cataacatta acatttgaaa aatggcacca gctcaaaacc        60
tagtcagttc gaaacacgta gcggtgatcg gagccggagc atccgggtta atagcggcca       120
gagagctcca tcgtgaaggt cacaccgtcg tcgttttga gcgggagaaa caagtgggag        180
gtctctggat ttactcacct aaatctgaat ccgacccgct tggtctcgac ccgacaagac       240
ctatagttca ctcgagtgtc tacgagtctc tccgaaccaa cctcccgaga gagtgtatgg       300
gtttcaggga ttttccgttc gtgccatgtg ttgatgactt tcaagagac tcgagaaggt       360 atccgagcca cagggaagtt cttgcgtacc ttcaagactt tgctagagag tttaaaatag      420
aggagatggt ccggttcgag accgaggtgg ttcgggttga gccggttgat ggaaaatgga      480
gggtccgatc caaaaactcc gatgatctct ccgaagatga gatctttgac gcagtcgttg      540
tttgcagtgg gcattatacc gaaccttatg ttgctcatat tcctgggata aaatcatggc      600
caggaaagca gatccatagc cataactaca gagttccggg tccattcaaa aatgaggtgg      660
tggtggtcat cggaaatttt gcgagcggtg ccgatattag tagagacgta gctaaggtcg      720
ccaaagaagt ccacgttgcg tctagaggga gtgaagctag tacgtatgag aagctttccg      780
tgcccaccaa caatctatgg attcattctg agatagagac tgcatgtgat gatggttcaa      840
ttgttttcaa aaatgggaag gcggttcatg cagatactgt tgtgtattgt accgggtaca      900
agtataagtt tccatttctt gaaaccaatg gttatatgag cattgatgat aaccgcgttg      960

-continued

```
aacctttgta caaacatgtc tttccaccgg cgcttgcccc agggctttct tttgttggtt    1020
taccagggat gggcatacaa ttcgtcatgt ttgaaatcca agcaaatgg gtagctgcag     1080 ttttgtctgg acgagttaca cttcctgcac cagaaaaaat gatggaagat cttattgcat   1140
cgtatgccat gcttgaagcg ttaggtattc ccaagagata tacacataaa ttgggtaaaa   1200
ttcagtctaa ttatcttgac tgggtcgcag aagaatgtgg ttgtcagcct gttgagcctt   1260
ggagaactca acaagttgac cgtggttatg agagacttgt ttctaaccct gaaaattacc   1320
gcgatgaatg ggacgacgat gatctcataa aagaagcgta cgaggatttt gctagtaaga   1380
agttgattag ctttcttcct tcttatttcc ccaaatcagg aagatgatat cccataatgg   1440
tgcctacttg tttttaaggg tctacttgta ttattttaa aaatgttggt tttaataaag    1500
ctgaatgtaa gggttgcttg ttatacaatg gctactactt ttccctcgtg cc            1552
```

<210> SEQ ID NO 4
<211> LENGTH: 461
<212> TYPE: PRT
<213> ORGANISM: Brassica rapa

<400> SEQUENCE: 4

```
Met Ala Pro Ala Gln Asn Leu Val Ser Ser Lys His Val Ala Val Ile
1               5                   10                  15

Gly Ala Gly Ala Ser Gly Leu Ile Ala Ala Arg Glu Leu His Arg Glu
                20                  25                  30

Gly His Thr Val Val Phe Glu Arg Glu Lys Gln Val Gly Gly Leu
            35                  40                  45

Trp Ile Tyr Ser Pro Lys Ser Glu Ser Asp Pro Gly Leu Asp Pro
    50                  55                  60

Thr Arg Pro Ile Val His Ser Ser Val Tyr Glu Ser Leu Arg Thr Asn
65                  70                  75                  80

Leu Pro Arg Glu Cys Met Gly Phe Arg Asp Phe Pro Phe Val Pro Cys
                85                  90                  95

Val Asp Asp Phe Ser Arg Asp Ser Arg Arg Tyr Pro Ser His Arg Glu
            100                 105                 110

Val Leu Ala Tyr Leu Gln Asp Phe Ala Arg Glu Phe Lys Ile Glu Glu
        115                 120                 125

Met Val Arg Phe Glu Thr Glu Val Val Arg Val Glu Pro Val Asp Gly
    130                 135                 140

Lys Trp Arg Val Arg Ser Lys Asn Ser Asp Asp Leu Ser Glu Asp Glu
145                 150                 155                 160

Ile Phe Asp Ala Val Val Val Cys Ser Gly His Tyr Thr Glu Pro Tyr
                165                 170                 175

Val Ala His Ile Pro Gly Ile Lys Ser Trp Pro Gly Lys Gln Ile His
            180                 185                 190

Ser His Asn Tyr Arg Val Pro Gly Pro Phe Lys Asn Glu Val Val Val
        195                 200                 205

Val Ile Gly Asn Phe Ala Ser Gly Ala Asp Ile Ser Arg Asp Val Ala
    210                 215                 220

Lys Val Ala Lys Glu Val His Val Ala Ser Arg Gly Ser Glu Ala Ser
225                 230                 235                 240

Thr Tyr Glu Lys Leu Ser Val Pro Thr Asn Asn Leu Trp Ile His Ser
                245                 250                 255

Glu Ile Glu Thr Ala Cys Asp Asp Gly Ser Ile Val Phe Lys Asn Gly
            260                 265                 270
```

```
Lys Ala Val His Ala Asp Thr Val Val Tyr Cys Thr Gly Tyr Lys Tyr
            275                 280                 285

Lys Phe Pro Phe Leu Glu Thr Asn Gly Tyr Met Ser Ile Asp Asp Asn
            290                 295                 300

Arg Val Glu Pro Leu Tyr Lys His Val Phe Pro Ala Leu Ala Pro
305                 310                 315                 320

Gly Leu Ser Phe Val Gly Leu Pro Gly Met Gly Ile Gln Phe Val Met
            325                 330                 335

Phe Glu Ile Gln Ser Lys Trp Val Ala Ala Val Leu Ser Gly Arg Val
            340                 345                 350

Thr Leu Pro Ala Pro Glu Lys Met Met Glu Asp Leu Ile Ala Ser Tyr
            355                 360                 365

Ala Met Leu Glu Ala Leu Gly Ile Pro Lys Arg Tyr Thr His Lys Leu
            370                 375                 380

Gly Lys Ile Gln Ser Asn Tyr Leu Asp Trp Val Ala Glu Glu Cys Gly
385                 390                 395                 400

Cys Gln Pro Val Glu Pro Trp Arg Thr Gln Gln Val Asp Arg Gly Tyr
            405                 410                 415

Glu Arg Leu Val Ser Asn Pro Glu Asn Tyr Arg Asp Glu Trp Asp Asp
            420                 425                 430

Asp Asp Leu Ile Lys Glu Ala Tyr Glu Asp Phe Ala Ser Lys Lys Leu
            435                 440                 445

Ile Ser Phe Leu Pro Ser Tyr Phe Pro Lys Ser Gly Arg
            450                 455                 460

<210> SEQ ID NO 5
<211> LENGTH: 1526
<212> TYPE: DNA
<213> ORGANISM: Cucumis sativus

<400> SEQUENCE: 5
gaaaacatga ataaacgaat cttatcataa tttgcaaaaa tcgaaaccaa attagttgac      60
aaccacatcg aacaagaatc atcaataatc caattccctt ttctaatcgg aaaatcaaac     120
ggatgttatc tcctctcaat ttcctcccaa cttcccgccg cgtggcagta atcggcgccg     180
gtgccggtgg cctcgtcact gcccgtgagc tcggccgcga gggccaccat gtcgtcgttt     240
tcgaacgtaa tactcgaatc ggagggacct gggtatattc ctcagagatt gaatccgacc     300
cacttggact cgacccaaat cggacccgaa ttcacagcag tctctacaaa tctctacgca     360
ccaatctccc cagagaactc atgggggtcc gcgattaccc ttttgttcct cgagaagggg     420
aggatcgaga tcccaggcga tttccaagtc accgggaggt tctgaagtat ttagaagatt     480
cgctaatga atttgggatt tgtaaattgg tgagatttgg aactgaggtg gtatttgctg     540
gtctggagga ggttgggaaa tggaggattg aatttagatg tgaaaatggg gatgttgaag     600
aagacctttt tgatgctctg gttgtttgtg ttggcaatta ttcacagcct cgagtggcag     660
agattcctgg gattgatgga tggcctgggg agcaagtgca tagtcacaat tatcgtgatc     720
ccgaaccatt tcgggggtaa gttgttgtct tgataggtta ttcttcgagt ggtacagaca     780
tttctcagga gctcattggg gttgccaaag aaattcatat tgcttggaga tcaactaaaa     840
cagagctttt gaacacagaa tcaattaaca gtaatgtgtc atttcatcca atgattgaaa     900
gtgtccataa agatggggca gtggttttt aagacgggtg cgttgttttg ctgatatta     960
ttctgcattg cactgggtac aaatatcatt tccctttttct tgaaaccaat ggcattgtta    1020
cggtggacaa caaccgtgta ggaccctat acaagcatgt cttccccca gcattggccc     1080
```

```
caggqcttc cttttgttggg ttaccattta aggctgttcc tttgcccatc tttgagcttc   1140
aaagcaattg gattgctggt gttttatcaa acaggattgc acttccatca aaagaggaaa   1200
tgttggcaga tgttaaagct ttctatgaaa atcttgaagc ttttgggaag cccaagcatc   1260
ggacccatga attgggtgat gatatgcctg tgtattgtaa ctggcttgca acaacttgtg   1320
gttgtccagc ctttgaagaa tggaggaaga aaatgtacat tgctattggt atttataaaa   1380
aggccaatct cgagacatat cgtgatgatt ggcaggacaa tgagttgatt cgtcaagctt   1440
acgaggaatt cagcaagtat aaatacaaat gaaaggacac tcaaaaccac atagttttga   1500
atgcttcata agattggttc tatatg                                        1526
```

<210> SEQ ID NO 6
<211> LENGTH: 449
<212> TYPE: PRT
<213> ORGANISM: Cucumis sativus

<400> SEQUENCE: 6

```
Met Leu Ser Pro Leu Asn Phe Leu Pro Thr Ser Arg Arg Val Ala Val
1               5                   10                  15

Ile Gly Ala Gly Ala Gly Gly Leu Val Thr Ala Arg Glu Leu Gly Arg
            20                  25                  30

Glu Gly His His Val Val Val Phe Glu Arg Asn Thr Arg Ile Gly Gly
        35                  40                  45

Thr Trp Val Tyr Ser Ser Glu Ile Glu Ser Asp Pro Leu Gly Leu Asp
    50                  55                  60

Pro Asn Arg Thr Arg Ile His Ser Ser Leu Tyr Lys Ser Leu Arg Thr
65                  70                  75                  80

Asn Leu Pro Arg Glu Leu Met Gly Val Arg Asp Tyr Pro Phe Val Pro
                85                  90                  95

Arg Glu Gly Glu Asp Arg Asp Pro Arg Arg Phe Pro Ser His Arg Glu
            100                 105                 110

Val Leu Lys Tyr Leu Glu Asp Phe Ala Asn Glu Phe Gly Ile Cys Lys
        115                 120                 125

Leu Val Arg Phe Gly Thr Glu Val Val Phe Ala Gly Leu Glu Glu Val
    130                 135                 140

Gly Lys Trp Arg Ile Glu Phe Arg Cys Glu Asn Gly Asp Val Glu Glu
145                 150                 155                 160

Asp Leu Phe Asp Ala Leu Val Val Cys Val Gly Asn Tyr Ser Gln Pro
                165                 170                 175

Arg Val Ala Glu Ile Pro Gly Ile Asp Gly Trp Pro Gly Glu Gln Val
            180                 185                 190

His Ser His Asn Tyr Arg Asp Pro Glu Pro Phe Arg Gly Lys Val Val
        195                 200                 205

Val Leu Ile Gly Tyr Ser Ser Ser Gly Thr Asp Ile Ser Gln Glu Leu
    210                 215                 220

Ile Gly Val Ala Lys Glu Ile His Ile Ala Trp Arg Ser Thr Lys Thr
225                 230                 235                 240

Glu Leu Leu Asn Thr Glu Ser Ile Asn Ser Asn Val Ser Phe His Pro
                245                 250                 255

Met Ile Glu Ser Val His Lys Asp Gly Ala Val Val Phe Gln Asp Gly
            260                 265                 270

Cys Val Val Leu Ala Asp Ile Ile Leu His Cys Thr Gly Tyr Lys Tyr
        275                 280                 285
```

```
His Phe Pro Phe Leu Glu Thr Asn Gly Ile Val Thr Val Asp Asn Asn
    290                 295                 300

Arg Val Gly Pro Leu Tyr Lys His Val Phe Pro Pro Ala Leu Ala Pro
305                 310                 315                 320

Gly Leu Ser Phe Val Gly Leu Pro Phe Lys Ala Val Pro Leu Pro Ile
                325                 330                 335

Phe Glu Leu Gln Ser Asn Trp Ile Ala Gly Val Leu Ser Asn Arg Ile
            340                 345                 350

Ala Leu Pro Ser Lys Glu Glu Met Leu Ala Asp Val Lys Ala Phe Tyr
        355                 360                 365

Glu Asn Leu Glu Ala Phe Gly Lys Pro Lys His Arg Thr His Glu Leu
    370                 375                 380

Gly Asp Asp Met Pro Val Tyr Cys Asn Trp Leu Ala Thr Thr Cys Gly
385                 390                 395                 400

Cys Pro Ala Phe Glu Glu Trp Arg Lys Lys Met Tyr Ile Ala Ile Gly
                405                 410                 415

Ile Tyr Lys Lys Ala Asn Leu Glu Thr Tyr Arg Asp Asp Trp Gln Asp
            420                 425                 430

Asn Glu Leu Ile Arg Gln Ala Tyr Glu Glu Phe Ser Lys Tyr Lys Tyr
        435                 440                 445

Lys

<210> SEQ ID NO 7
<211> LENGTH: 1541
<212> TYPE: DNA
<213> ORGANISM: Cucumis sativus

<400> SEQUENCE: 7
atggaattca tcgctacttg ccaccctgac tttcctcccc ctccggcctc acctcaaccc      60
acgacgatgc aacactcccg ccgcgtggca gtgatcggcg ccggtggcgc aggcctcatc     120
tccgcccgcc aactttcccg ggagggccac caagtcgtgg tcttcgaacg gaataatcag     180
atcggagggg tctgggtata ttcgcccgaa attgaatccg acccacttgg agttcaccct     240
aagcggactc gaatacatag cagcctctac aaatctctac gaaccaatat ccccagagaa     300
gtcatggggg tccgtgattt ccccttttgtt cctcgagaag gggaggatcg agatcccagg     360
cgatttccaa gtcaccggga ggttctgaag tatttagaag atttcgctaa tgaatttggg     420
atttgtaaat tggtgagatt tagaactgag gtggtgtttg ctggtttgga aagcttggc     480 aaatggaggg ttgaattcag atgtgagaat ggggatgttc attatgacat ttttgatgct     540
gtagttgttt gtgttggcaa tttttcgcag cctcgagtag cagagattcc agggattgat     600
ggatggcctg gggagcaagt gcatagtcac aattatcgtg atcccgaacc atttcgcggt     660
aaggttgttg tgttgatagg ttattcttcg agtggtacgg acatttctca ggagctcatt     720
ggggttgcca agaaaattca tattgcttgc aggccagcta aacagagtc ttcggacgaa     780 aaatcaatta ttagtaacgt ctcatttcat ccaatgatcg aaagtgtcca taaagatgga     840
acggtggtct ttcaagacgg gtccgtcgtt tcggctgatg ttattctgca ttgtactggg     900
tacaaatatc atttcccgtt tcttgaaacc aatggcactg ttacggtgga cgacaaccgt     960
gtaggacctc tttttcaagca tgtcttcccc ccagcattgg ccccagggct tccttcgtt    1020 gggttaccat ttaaggttgt tccttttgtc atatttgagc ttcaaagcaa ttggattgct    1080
ggtgttttat caaacaggat tgcacttcca tcaaaagagg aaatgttggc agatgttaaa    1140 gcttttatg aagaactcga agctcgtggc aagcccaagc atcggaccca taaattgggt    1200
```

```
ggttatacgc ctgcctactg taactggctt gcagcaactt gtggttgtcc tccctatgaa    1260
gaatggagaa aggaaatgtt tgttgctact gatattaata aagtggccaa tcttgagtca    1320
taccgtgatg attggcatga cgatgagttg attcatcaag cttatgaaga atttggcaag    1380
tatactacta caaatgaagg aagtcaaaac cactcgaatt tgaatgttta ataagtttgg    1440
ttctatatat ttgtacattg cacaatcatg tgtcttgatt ataaatgttg gatcttgatt    1500
tataaataaa aatgaaaata atattagacc agattatgac a                       1541
```

<210> SEQ ID NO 8
<211> LENGTH: 476
<212> TYPE: PRT
<213> ORGANISM: Cucumis sativus

<400> SEQUENCE: 8

```
Met Glu Phe Ile Ala Thr Cys His Pro Asp Phe Pro Pro Pro Pro Ala
1               5                   10                  15

Ser Pro Gln Pro Thr Thr Met Gln His Ser Arg Arg Val Ala Val Ile
            20                  25                  30

Gly Ala Gly Gly Ala Gly Leu Ile Ser Ala Arg Gln Leu Ser Arg Glu
        35                  40                  45

Gly His Gln Val Val Phe Glu Arg Asn Asn Gln Ile Gly Gly Val
    50                  55                  60

Trp Val Tyr Ser Pro Glu Ile Glu Ser Asp Pro Leu Gly Val His Pro
65                  70                  75                  80

Lys Arg Thr Arg Ile His Ser Ser Leu Tyr Lys Ser Leu Arg Thr Asn
                85                  90                  95

Ile Pro Arg Glu Val Met Gly Val Arg Asp Phe Pro Phe Val Pro Arg
            100                 105                 110

Glu Gly Glu Asp Arg Asp Pro Arg Arg Phe Pro Ser His Arg Glu Val
        115                 120                 125

Leu Lys Tyr Leu Glu Asp Phe Ala Asn Glu Phe Gly Ile Cys Lys Leu
    130                 135                 140

Val Arg Phe Arg Thr Glu Val Val Phe Ala Gly Leu Glu Lys Leu Gly
145                 150                 155                 160

Lys Trp Arg Val Glu Phe Arg Cys Glu Asn Gly Asp Val His Tyr Asp
                165                 170                 175

Ile Phe Asp Ala Val Val Val Cys Val Gly Asn Phe Ser Gln Pro Arg
            180                 185                 190

Val Ala Glu Ile Pro Gly Ile Asp Gly Trp Pro Gly Glu Gln Val His
        195                 200                 205

Ser His Asn Tyr Arg Asp Pro Glu Pro Phe Arg Gly Lys Val Val Val
    210                 215                 220

Leu Ile Gly Tyr Ser Ser Gly Thr Asp Ile Ser Gln Glu Leu Ile
225                 230                 235                 240

Gly Val Ala Lys Glu Ile His Ile Ala Cys Arg Pro Ala Lys Thr Glu
                245                 250                 255

Ser Ser Asp Glu Lys Ser Ile Ile Ser Asn Val Ser Phe His Pro Met
            260                 265                 270

Ile Glu Ser Val His Lys Asp Gly Thr Val Val Phe Gln Asp Gly Ser
        275                 280                 285

Val Val Ser Ala Asp Val Ile Leu His Cys Thr Gly Tyr Lys Tyr His
    290                 295                 300

Phe Pro Phe Leu Glu Thr Asn Gly Thr Val Thr Val Asp Asp Asn Arg
```

```
            305                 310                 315                 320
Val Gly Pro Leu Phe Lys His Val Phe Pro Ala Leu Ala Pro Gly
                325                 330                 335

Leu Ser Phe Val Gly Leu Pro Phe Lys Val Val Pro Phe Val Ile Phe
                340                 345                 350

Glu Leu Gln Ser Asn Trp Ile Ala Gly Val Leu Ser Asn Arg Ile Ala
                355                 360                 365

Leu Pro Ser Lys Glu Glu Met Leu Ala Asp Val Lys Ala Phe Tyr Glu
    370                 375                 380

Glu Leu Glu Ala Arg Gly Lys Pro Lys His Arg Thr His Lys Leu Gly
385                 390                 395                 400

Gly Tyr Thr Pro Ala Tyr Cys Asn Trp Leu Ala Ala Thr Cys Gly Cys
                    405                 410                 415

Pro Pro Tyr Glu Glu Trp Arg Lys Glu Met Phe Val Ala Thr Asp Ile
                420                 425                 430

Asn Lys Val Ala Asn Leu Glu Ser Tyr Arg Asp Asp Trp His Asp Asp
                435                 440                 445

Glu Leu Ile His Gln Ala Tyr Glu Glu Phe Gly Lys Tyr Thr Thr Thr
    450                 455                 460

Asn Glu Gly Ser Gln Asn His Ser Asn Leu Asn Val
465                 470                 475

<210> SEQ ID NO 9
<211> LENGTH: 1570
<212> TYPE: DNA
<213> ORGANISM: Cucumis sativus

<400> SEQUENCE: 9
atgtggagta gagttggtag cacttcagct atcattcata cttttatcaa aaaagattcc      60
catttcttac ccataaatcc atgttctact caattagcta cactcaattt cctcccctcc     120
cctcaaccat caacgatgcc tcactccagc cgcgtggcag tgatcggcgc cggcgccgga     180
ggcctcgtct cagcccggga actttccgg gaggaccacc atgtggttgt attcgaacgg      240
aatactcaaa ttggaggggc ctgggtatat tcaccggaaa ttgaatccga cccacttgga     300
gtcgacccgg atcgacccg aatccatagc agcctcttca aatctcttcg aaccaatata      360
cctagagaac tcatgggggt ccgggatttc ccgtttgttc ctcgagaagg ggaggatcga     420
gatccgaggc gatttccaag tcatcaggag gttcgcaagt atttggaaga tttcgctaat     480
gaatttgggg tttacaaatt tgtgagattt ggaactgagg ttgtgtttgc tggtttggag     540
gagcttggga aatggaggat tgaatttaga tgtgaaaatg gggacgttga ttatgagatt     600
tttgatgctg tggttgtttg tgttgggaat tattcgcagc ctcgagtagc agagattcct     660
gggattgatg gatggcctgg agagcaagtg catagtcaca attatcgtga tcccgaacca     720
tttcggggta aggttgttgt gttgataggt tattcttcga gtggaacaga catttctcag     780
gagctcattg gggttgccaa agaaattcat attgtttgga gatcacctaa acagagctt     840
ttggacagag aatcaattat tagtaatgtt tcatttcatc caatgattga agtgtgtgt      900
aaagatggga cagtggtctt tcaagacggg tgtgttgttt cggctgatgt aattttgcat     960
tgcactgggt acaactatca tttcccttc cttgaaacca atggcaatgt tacagtggac    1020
gacaaccgtg taggacctct atacaagcat gtcttccccc cagcattggc ccgggggctt    1080
tcctttgttg gattaccatt caaggttatt ccttttccct gttgagct tcaaagcaat     1140
tgggttgctg gtgttttatc aaaaaggatt gcacttccat caaaagagga aatgttggca    1200
```

-continued

```
gatgttaaag ctttctatga agatcttgaa gctcttggca agcccaagca tcggacccat    1260
ttattgggtg attatatgat gcctgcctat tgtaattggg ttgcaacaac ttgtggttgt    1320
cctccctatg aagaatggag aaaggaaatg aacatttctg ttcatcttta tagattgccc    1380
aatctcaaga cgtaccgtga tgattggcac gatgatgagt tgattcgtca agcttacgag    1440
gagtttagca agtataatac aaatgtaaga agtcaaaaca actcaaattt gaatgcttca    1500
taagatttgt tgtatatgtg tacatttaca tatttatgtt gtcattgatc cttcctcctc    1560
gttacaaata                                                            1570
```

<210> SEQ ID NO 10
<211> LENGTH: 500
<212> TYPE: PRT
<213> ORGANISM: Cucumis sativus

<400> SEQUENCE: 10

```
Met Trp Ser Arg Val Gly Ser Thr Ser Ala Ile Ile His Thr Phe Ile
 1               5                  10                  15

Lys Lys Asp Ser His Phe Leu Pro Ile Asn Pro Cys Ser Thr Gln Leu
            20                  25                  30

Ala Thr Leu Asn Phe Leu Pro Ser Pro Gln Pro Ser Thr Met Pro His
        35                  40                  45

Ser Ser Arg Val Ala Val Ile Gly Ala Gly Ala Gly Leu Val Ser
50                  55                  60

Ala Arg Glu Leu Ser Arg Glu Asp His His Val Val Phe Glu Arg
65                  70                  75                  80

Asn Thr Gln Ile Gly Gly Ala Trp Val Tyr Ser Pro Glu Ile Glu Ser
                85                  90                  95

Asp Pro Leu Gly Val Asp Pro Asp Arg Thr Arg Ile His Ser Ser Leu
            100                 105                 110

Phe Lys Ser Leu Arg Thr Asn Ile Pro Arg Glu Leu Met Gly Val Arg
        115                 120                 125

Asp Phe Pro Phe Val Pro Arg Glu Gly Glu Asp Arg Asp Pro Arg Arg
130                 135                 140

Phe Pro Ser His Gln Glu Val Arg Lys Tyr Leu Glu Asp Phe Ala Asn
145                 150                 155                 160

Glu Phe Gly Val Tyr Lys Phe Val Arg Phe Gly Thr Glu Val Val Phe
                165                 170                 175

Ala Gly Leu Glu Glu Leu Gly Lys Trp Arg Ile Glu Phe Arg Cys Glu
            180                 185                 190

Asn Gly Asp Val Asp Tyr Glu Ile Phe Asp Ala Val Val Cys Val
        195                 200                 205

Gly Asn Tyr Ser Gln Pro Arg Val Ala Glu Ile Pro Gly Ile Asp Gly
210                 215                 220

Trp Pro Gly Glu Gln Val His Ser His Asn Tyr Arg Asp Pro Glu Pro
225                 230                 235                 240

Phe Arg Gly Lys Val Val Leu Ile Gly Tyr Ser Ser Ser Gly Thr
                245                 250                 255

Asp Ile Ser Gln Glu Leu Ile Gly Val Ala Lys Glu Ile His Ile Val
            260                 265                 270

Trp Arg Ser Pro Lys Thr Glu Leu Leu Asp Arg Glu Ser Ile Ile Ser
        275                 280                 285

Asn Val Ser Phe His Pro Met Ile Glu Ser Val Cys Lys Asp Gly Thr
290                 295                 300
```

```
Val Val Phe Gln Asp Gly Cys Val Ser Ala Asp Val Ile Leu His
305                 310                 315                 320

Cys Thr Gly Tyr Asn Tyr His Phe Pro Phe Leu Glu Thr Asn Gly Asn
            325                 330                 335

Val Thr Val Asp Asp Asn Arg Val Gly Pro Leu Tyr Lys His Val Phe
                340                 345                 350

Pro Pro Ala Leu Ala Pro Gly Leu Ser Phe Val Gly Leu Pro Phe Lys
            355                 360                 365

Val Ile Pro Phe Pro Leu Phe Glu Leu Gln Ser Asn Trp Val Ala Gly
370                 375                 380

Val Leu Ser Lys Arg Ile Ala Leu Pro Ser Lys Glu Glu Met Leu Ala
385                 390                 395                 400

Asp Val Lys Ala Phe Tyr Glu Asp Leu Glu Ala Leu Gly Lys Pro Lys
                405                 410                 415

His Arg Thr His Leu Leu Gly Asp Tyr Met Met Pro Ala Tyr Cys Asn
            420                 425                 430

Trp Val Ala Thr Thr Cys Gly Cys Pro Pro Tyr Glu Glu Trp Arg Lys
            435                 440                 445

Glu Met Asn Ile Ser Val His Leu Tyr Arg Leu Pro Asn Leu Lys Thr
    450                 455                 460

Tyr Arg Asp Asp Trp His Asp Asp Glu Leu Ile Arg Gln Ala Tyr Glu
465                 470                 475                 480

Glu Phe Ser Lys Tyr Asn Thr Asn Val Arg Ser Gln Asn Asn Ser Asn
                485                 490                 495

Leu Asn Ala Ser
            500

<210> SEQ ID NO 11
<211> LENGTH: 1590
<212> TYPE: DNA
<213> ORGANISM: Cucumis sativus

<400> SEQUENCE: 11
aacatgaata aacgaatctt atcataattt gcaaaaatcg aaaccaaatt agttgacaac      60
cacatcgaac aagaatcatc aataatccaa ttccctttc taatcggaaa atcaaacgga     120
tgttatctcc tctcaatttc ctcccaactt cccgccgcgt ggcagtaatc ggcgccggtg     180
ccggtggcct cgtcactgcc cgtgagctcg gccgcgaggg ccaccatgtc gtcgttttcg     240
aacgtaatac tcgaatcgga gggacctggg tatattcctc agagattgaa tccgacccac     300
ttggactcga cccaaatcgg acccgaattc acagcagtct ctacaaatct ctacgcacca     360
atctccccag agaactcatg ggggtccgcg attacccttt tgttcctcga agggggaggt     420
atagagatcc gaggcgattt ccaagtcacc gggaggttcc gaagtattta aagatttcg      480 ctaatgaatt tgggatttgt aaattggtga gatttggaac tgaggtggta tttgctggtc     540
tggaggaggt tgggaaatgg aggattgaat ttagatgtga aaatgggggat gttgaagaag    600 accttttga tgctctggtt gtttgtgttg gcaattattc acagcctcga gtggcagaga     660
ttcctgggat tgatgaggg cctggggagc aattacatag tcacaattat cgtgatcccg     720
aaccatttcg gggtaaggtt gttgtcttga taggttattc ttcgagtggt acagacattt     780
ctcaggagct cattgggggtt gccaaagaaa ttcatattgc ttggagatca actaaaacag     840
agcttttgaa cacagaatca attaacagta atgtgtcatt tcatccaatg attgaaagtg     900
tccataaaga tggggcagtg gtttttcaag acgggtgcgt tgttttggct gatattattc     960
```

```
tgcattgcac tgggtacaaa tatcatttcc cttttcttga aaccaatggc attgttacgg   1020
tggacaacaa ccgtgtaggg cccctataca agcatgtctt ccccccagca ttggccccag   1080
ggctttcctt tgttgggtta ccatttaagg ttgttccttt tcccttgttt gagcttcaaa   1140
gcaattggat tgctggtgtt ttatcaaaca ggattgcact tccatcaaaa gaggaaatgt   1200
tggcagatgt taaagctttc tatgaaaatc ttgaagcttt tgggaagccc aagcatcgga   1260
cccatgaatt gggtgatgat atgcctgcct acttggactg gcttgcagca gtatgtggtt   1320
gtcctgccta tgaagaatgg agaaaggaaa tgtacattgc tactcatatg aataaagtgg   1380
ccaatctcag gtcataccgt gacgattggc acgacaatga gttgattcgt caagcttatg   1440
aagaatttag caagtatgca acaaatgaag gaagtgggaa ccactcaaaa ttgagtgttt   1500
gataagattg gttgtataca tgttacataa tttatgtgtt gttgattaat gaaaataata   1560
gtagtatggg atcgcccatt ttctttacaa                                   1590
```

<210> SEQ ID NO 12
<211> LENGTH: 460
<212> TYPE: PRT
<213> ORGANISM: Cucumis sativus

<400> SEQUENCE: 12

```
Met Leu Ser Pro Leu Asn Phe Leu Pro Thr Ser Arg Arg Val Ala Val
1               5                   10                  15

Ile Gly Ala Gly Ala Gly Gly Leu Val Thr Ala Arg Glu Leu Gly Arg
            20                  25                  30

Glu Gly His His Val Val Phe Glu Arg Asn Thr Arg Ile Gly Gly
        35                  40                  45

Thr Trp Val Tyr Ser Ser Glu Ile Glu Ser Asp Pro Leu Gly Leu Asp
    50                  55                  60

Pro Asn Arg Thr Arg Ile His Ser Ser Leu Tyr Lys Ser Leu Arg Thr
65                  70                  75                  80

Asn Leu Pro Arg Glu Leu Met Gly Val Arg Asp Tyr Pro Phe Val Pro
                85                  90                  95

Arg Glu Gly Glu Asp Arg Asp Pro Arg Arg Phe Pro Ser His Arg Glu
            100                 105                 110

Val Leu Lys Tyr Leu Glu Asp Phe Ala Asn Glu Phe Gly Ile Cys Lys
        115                 120                 125

Leu Val Arg Phe Gly Thr Glu Val Phe Ala Gly Leu Glu Glu Val
    130                 135                 140

Gly Lys Trp Arg Ile Glu Phe Arg Cys Glu Asn Gly Asp Val Glu Glu
145                 150                 155                 160

Asp Leu Phe Asp Ala Leu Val Cys Val Gly Asn Tyr Ser Gln Pro
                165                 170                 175

Arg Val Ala Glu Ile Pro Gly Ile Asp Gly Trp Pro Gly Gln Leu
            180                 185                 190

His Ser His Asn Tyr Arg Asp Pro Glu Pro Phe Arg Gly Lys Val Val
        195                 200                 205

Val Leu Ile Gly Tyr Ser Ser Ser Gly Thr Asp Ile Ser Gln Glu Leu
    210                 215                 220

Ile Gly Val Ala Lys Glu Ile His Ile Ala Trp Arg Ser Thr Lys Thr
225                 230                 235                 240

Glu Leu Leu Asn Thr Glu Ser Ile Asn Ser Asn Val Ser Phe His Pro
                245                 250                 255
```

Met Ile Glu Ser Val His Lys Asp Gly Ala Val Phe Gln Asp Gly
                260                 265                 270

Cys Val Val Leu Ala Asp Ile Ile Leu His Cys Thr Gly Tyr Lys Tyr
            275                 280                 285

His Phe Pro Phe Leu Glu Thr Asn Gly Ile Val Thr Val Asp Asn Asn
    290                 295                 300

Arg Val Gly Pro Leu Tyr Lys His Val Phe Pro Ala Leu Ala Pro
305                 310                 315                 320

Gly Leu Ser Phe Val Gly Leu Pro Phe Lys Val Pro Phe Pro Leu
                325                 330                 335

Phe Glu Leu Gln Ser Asn Trp Ile Ala Gly Val Leu Ser Asn Arg Ile
            340                 345                 350

Ala Leu Pro Ser Lys Glu Glu Met Leu Ala Asp Val Lys Ala Phe Tyr
    355                 360                 365

Glu Asn Leu Glu Ala Phe Gly Lys Pro Lys His Arg Thr His Glu Leu
        370                 375                 380

Gly Asp Asp Met Pro Ala Tyr Leu Asp Trp Leu Ala Ala Val Cys Gly
385                 390                 395                 400

Cys Pro Ala Tyr Glu Glu Trp Arg Lys Glu Met Tyr Ile Ala Thr His
                405                 410                 415

Met Asn Lys Val Ala Asn Leu Arg Ser Tyr Arg Asp Asp Trp His Asp
            420                 425                 430

Asn Glu Leu Ile Arg Gln Ala Tyr Glu Glu Phe Ser Lys Tyr Ala Thr
    435                 440                 445

Asn Glu Gly Ser Gly Asn His Ser Lys Leu Ser Val
        450                 455                 460

<210> SEQ ID NO 13
<211> LENGTH: 1600
<212> TYPE: DNA
<213> ORGANISM: Medicago truncatula

<400> SEQUENCE: 13
atgaatgaac atgttcatac tgtaagcatt caattcgatt ccaagccaat gaaattcatc      60
atgtccaccg caacaccact tctcacaccc cgccacgtgg cagtcatcgg agccggcgcc     120
ggaggcttag tagcagcacg cgagctccga cgagaaggac atcaagtagt agtcttcgag     180
cgaggagaag aattgggcgg ttcatgggtc tacacttcag aggtagaatc cgacccactc     240
ggtttggacc cgaaccggaa gcttatccac tcgagcctat acaattcact ccgaaccaat     300
ttgcctcggg agagtatggg tttccgagat tacccttta ggaggaaaga agagaagggg     360
agagattcta gaaggttccc gagtcatgga gaggtattga tgtatttgaa ggattttgct     420
gcggattttg agattagtga tttggtgagg ttgaagacag aggtggtgtt tgctggggtg     480
ggtgaaggtg gaaaatggac ggtgagatct agatcagtgg agagagaatg tgtggatgag     540
atttatgatg ctgttgttgt ttgcaatgga cattattttc aaccaagact tcccaatatt     600
cctggcatta atgcatggcc agggaagcaa atgcatagcc ataattacag aacacccgag     660
ccctttcaag atcaagttgt agttctaatt ggtggtgctg ccagtgcggt tgatatttct     720
cgagacgtgg caaccgttgc taagaagtt catattgcag ctaggtctgt tgaagaagat     780
aagcttggaa agttacctgg ccatgataac atgtggcttc attctatgat tgacagtgtt     840
catgaagatg gtgcagtggt ttttaaagat ggaaatgcag ttatcgctga cttcattgta     900
cattgcacag ggtacaagta tgattttcct ttccttgaaa ccaacagcgt ggtgactgta     960

-continued

```
gatgacaatc gtgttggacc actctacaag catgttttc caccggcgtt agctccatgg    1020
ctttcctttg ttgggttacc ttggaaggtt gctcccttcc ctttgtttga attgcagagt    1080
aagtggatag ctggagtttt gtctaatcgc attgcccttc cttcagaaga ggagatgact    1140
aaagatattg aagcttttta cttgtcactt gaagaatctg gcattcctaa gaggcacact    1200
cataatatgg gcacgggcac ggccgatgtt cagtgggact acaataactg gcttgcagat    1260
cagtgtggtg ttcctgctat ggaagaatgg agaaggcaaa tgtatatggc tacatcgaag    1320
aacaggctct tgcgacctga gacttatcgt gatgagtggg acgatgatga cattgttcaa    1380
ctagctgagc atgaatttgc taagtatcag atataatgtt gtattgtttt gagatttacc    1440
aagtacaagt cattcatgcg ttatacgcct agttcagtgt tattcttaac gatcaaaaat    1500
cagctttaaa gtgcaaataa gaatgtaaat tatatatgtt tggaatactt tcaataattc    1560
attaatgaac atgtgataat gatgtgatct cttttatttt                         1600
```

<210> SEQ ID NO 14
<211> LENGTH: 471
<212> TYPE: PRT
<213> ORGANISM: Medicago truncatula

<400> SEQUENCE: 14

```
Met Asn Glu His Val His Thr Val Ser Ile Gln Phe Asp Ser Lys Pro
1               5                  10                  15

Met Lys Phe Ile Met Ser Thr Ala Thr Pro Leu Leu Thr Pro Arg His
            20                  25                  30

Val Ala Val Ile Gly Ala Gly Ala Gly Gly Leu Val Ala Ala Arg Glu
        35                  40                  45

Leu Arg Arg Glu Gly His Gln Val Val Phe Glu Arg Gly Glu Glu
    50                  55                  60

Leu Gly Gly Ser Trp Val Tyr Thr Ser Glu Val Glu Ser Asp Pro Leu
65                  70                  75                  80

Gly Leu Asp Pro Asn Arg Lys Leu Ile His Ser Ser Leu Tyr Asn Ser
                85                  90                  95

Leu Arg Thr Asn Leu Pro Arg Glu Ser Met Gly Phe Arg Asp Tyr Pro
            100                 105                 110

Phe Arg Arg Lys Glu Glu Lys Gly Arg Asp Ser Arg Arg Phe Pro Ser
        115                 120                 125

His Gly Glu Val Leu Met Tyr Leu Lys Asp Phe Ala Ala Asp Phe Glu
    130                 135                 140

Ile Ser Asp Leu Val Arg Leu Lys Thr Glu Val Phe Ala Gly Val
145                 150                 155                 160

Gly Glu Gly Gly Lys Trp Thr Val Arg Ser Arg Ser Val Glu Arg Glu
                165                 170                 175

Cys Val Asp Glu Ile Tyr Asp Ala Val Val Val Cys Asn Gly His Tyr
            180                 185                 190

Phe Gln Pro Arg Leu Pro Asn Ile Pro Gly Ile Asn Ala Trp Pro Gly
        195                 200                 205

Lys Gln Met His Ser His Asn Tyr Arg Thr Pro Glu Pro Phe Gln Asp
    210                 215                 220

Gln Val Val Leu Ile Gly Gly Ala Ala Ser Ala Val Asp Ile Ser
225                 230                 235                 240

Arg Asp Val Ala Thr Val Ala Lys Glu Val His Ile Ala Ala Arg Ser
                245                 250                 255

Val Glu Glu Asp Lys Leu Gly Lys Leu Pro Gly His Asp Asn Met Trp
```

```
                 260              265              270
Leu His Ser Met Ile Asp Ser Val His Glu Asp Gly Ala Val Val Phe
             275              280              285

Lys Asp Gly Asn Ala Val Ile Ala Asp Phe Ile Val His Cys Thr Gly
         290              295              300

Tyr Lys Tyr Asp Phe Pro Phe Leu Glu Thr Asn Ser Val Val Thr Val
305              310              315              320

Asp Asp Asn Arg Val Gly Pro Leu Tyr Lys His Val Phe Pro Pro Ala
                 325              330              335

Leu Ala Pro Trp Leu Ser Phe Val Gly Leu Pro Trp Lys Val Ala Pro
             340              345              350

Phe Pro Leu Phe Glu Leu Gln Ser Lys Trp Ile Ala Gly Val Leu Ser
         355              360              365

Asn Arg Ile Ala Leu Pro Ser Glu Glu Met Thr Lys Asp Ile Glu
     370              375              380

Ala Phe Tyr Leu Ser Leu Glu Glu Ser Gly Ile Pro Lys Arg His Thr
385              390              395              400

His Asn Met Gly Thr Gly Thr Ala Asp Val Gln Trp Asp Tyr Asn Asn
                 405              410              415

Trp Leu Ala Asp Gln Cys Gly Val Pro Ala Met Glu Glu Trp Arg Arg
             420              425              430

Gln Met Tyr Met Ala Thr Ser Lys Asn Arg Leu Leu Arg Pro Glu Thr
         435              440              445

Tyr Arg Asp Glu Trp Asp Asp Asp Ile Val Gln Leu Ala Glu His
     450              455              460

Glu Phe Ala Lys Tyr Gln Ile
465              470

<210> SEQ ID NO 15
<211> LENGTH: 2747
<212> TYPE: DNA
<213> ORGANISM: Oryza sativa

<400> SEQUENCE: 15
catgcctacg cagcctcatg tccagtcgag tgtaaccaca agcccacggg aatttgctgt      60
ccaatgaaga ccccacaaaa cgacaaactc caataccaca cacctccgct tccctccaaa    120
tcgcaacaga aatccgaagc gaaatcgcgc acgaccgtc tcgcgatgcc gtccccgtcg      180
ctccgcctcg ccgtcgtcgg cgcgggcgcc gccggcctgg tggcggcgcg ggagctccgc    240
cgggagggcc actcccccgt ggtgttcgag cgcgccgcct ccgtgggcgg cacgtggctc    300
tacgacgccg cccccgccac ctccgacccg ctcgccgccg cgccgcccca ctccagcctc    360
tacgcctcgc tccgcaccaa cctgccgcgg gaggtgatgg gcttcctcga ctttcccttc    420
gcctcctccg ccgcggaggc cggcggcggc ggcgacacgc gcaggttccc cggccacgac    480
gaggtgctcc ggtatctgga ggagttcgcg cggcggttcg acctgtacgg cctcgtccgc    540
ttcgggacgg aggtggttag ggttcggagg gatggcggcg gcggcggcgg gaggtgggcg    600
gtgacgtcga ggaagatcgg ggagaagggg aggcgtgagg aggaggagga ggtgtatgat    660
gccatcgtgg tttgcaatgg ccattacacg gagcctcgcg tcgcccacat acctggtaat    720
ctcctcgtca ctagcaaagt tgcaatctaa tcaattttgc ttgaactact cctaatcatg    780
gacagattca aggaattaaa taattttggta cttcgtactg ttgccaatgt atggttgcaa    840
tgttgtgatc gtcgaatcca ggaaggttaa tttaactcca aattgaactc aaccgtttga    900
```

-continued

```
agttttgaaa atagattggg attgatttca aatctgtatt tttttaacac tgttatgatg      960
atcatcaaat ccaggaaggt taagtaaact caaaattaaa ctcaactgtt aggttgggat     1020
tgacttcaaa tatgtattct ttaaacactg acagggtgg aggcttggcc tggaaagcag      1080
atgcatagcc acaattaccg cgttccagag ccttccacg atcaagtaac tgtctttctt      1140
tacctgtgca atctttccta tcatgcattt gtgcttaaat gttatcttgg ttgatgcgtt     1200
gcacttgtag gtagtgatca taatcggggc atcagcaagt gcagtagaca tctcaaggga     1260
ccttgcaggt gttgcagaag aggttcatgt tgctgataga tcagcacctg cctgcacttg     1320
caaaaggcag cctggatatg ataatatgtg gctccattcc atggtaaacg ccctttttctc    1380
gtggtgagtg atagcatatg gtagctttat ccgctgaaag ggctgccaca tttagcacaa     1440
ctagaaaact aattttcaag ctgcagattg atcatgcaca agaagatggc tgcgtggtgt     1500
ttcaggatgg cagctcaatc aaagccgatg tcatcatgca ctgtactggg tatgtaaacc     1560
tgcactaccc tgcaacccat ttctcggctt cttgtgcgaa attgcatttt tgttactacc     1620
tccgtttcag gttatgccta gattcattaa tatcaatatg aatatgagca atgctagaaa     1680
gtcttataac ctaaaacgga ggaagtactt cagttgaaac taacaatgtg ttcctttcat     1740
ctgcctgtcg actagctact tgtatgattt tccattcctt gaggatgata gcgccatcac     1800
cgttgatgac aactgtgtcg atccactata caagcacgtt ttcccaccag aagtagcacc     1860
tcacctgtcc ttcatcggat tgccatggaa ggtcattatg tgtgcaaaaa gtgatgccat     1920
tcactttaga tgcacttgta attaagttgt cttgatcttg tgatgatcat aggatgtaaa     1980
gcattcccct gccttgcttc ttgcaggtca ttccttttcc attgtttgaa ctccaaagca     2040
aatgggttgc cggcgtgcta tcaggacgag tcaagcttcc ttcgagcgaa gaaatgatgg     2100
aagatgtgaa agccttccac tcgaaaaatgg aagcgcgtgg atggcctaag agatacgccc    2160
acaactttc agactgtcag gtagcctgga gatgctttga gtgtcagtta ccaaagttct     2220
aatgttttga aacgaaatta ataaatatga ttgtcatcta cctgcaattt ttcagtagtt     2280
tcgtttatgc tcccttgata agcttgtttt catttccagt ttgaatatga tgattggctt     2340
gcggagcaat gtggccatcc accaattgaa caatggagga agctgatgta tgctgctaat     2400
tcagagaaca aggctgctcg tccggagagt taccgcgatg agtgggacga tgatcatctt     2460
gtggcagaag cagcagaaga tttcaagaaa tacttgtaaa atctcaagaa gatttcattc     2520
aatgtacatg attgcaaatt tgcaatgcag aaaacatcag agaataattc tgtacaccca     2580
aaatctcaat tcatgtctgg aatgggcaca atgctcgtc atcagatagt tggtttactt      2640
gtgtattatt tgatcatttg atgcctgtag attgtaataa taacctgaag caaaaacaag     2700
agaataattc tgtgcatgag aaaggagaaa ccttgagtct ggaacgg                   2747
```

<210> SEQ ID NO 16
<211> LENGTH: 482
<212> TYPE: PRT
<213> ORGANISM: Oryza sativa

<400> SEQUENCE: 16

```
Met Lys Thr Pro Gln Asn Asp Lys Leu Gln Tyr His Thr Pro Pro Leu
1               5                   10                  15

Pro Ser Lys Ser Gln Gln Lys Ser Glu Ala Lys Ser Arg Thr His Arg
            20                  25                  30

Leu Ala Met Pro Ser Pro Ser Leu Arg Leu Ala Val Val Gly Ala Gly
        35                  40                  45
```

```
Ala Ala Gly Leu Val Ala Ala Arg Glu Leu Arg Arg Glu Gly His Ser
 50                  55                  60
Pro Val Val Phe Glu Arg Ala Ala Ser Val Gly Gly Thr Trp Leu Tyr
 65                  70                  75                  80
Asp Ala Ala Pro Ala Thr Ser Asp Pro Leu Ala Gly Ala Ala His
                 85                  90                  95
Ser Ser Leu Tyr Ala Ser Leu Arg Thr Asn Leu Pro Arg Glu Val Met
                100                 105                 110
Gly Phe Leu Asp Phe Pro Phe Ala Ser Ala Ala Glu Ala Gly Gly
                115                 120                 125
Gly Gly Asp Thr Arg Arg Phe Pro Gly His Asp Glu Val Leu Arg Tyr
130                 135                 140
Leu Glu Glu Phe Ala Arg Arg Phe Asp Leu Tyr Gly Leu Val Arg Phe
145                 150                 155                 160
Gly Thr Glu Val Val Arg Val Arg Asp Gly Gly Gly Gly Gly
                165                 170                 175
Arg Trp Ala Val Thr Ser Arg Lys Ile Gly Glu Lys Gly Arg Arg Glu
                180                 185                 190
Glu Glu Glu Glu Val Tyr Asp Ala Ile Val Val Cys Asn Gly His Tyr
                195                 200                 205
Thr Glu Pro Arg Val Ala His Ile Pro Gly Val Glu Ala Trp Pro Gly
210                 215                 220
Lys Gln Met His Ser His Asn Tyr Arg Val Pro Glu Pro Phe His Asp
225                 230                 235                 240
Gln Val Val Ile Ile Ile Gly Ala Ser Ala Ser Ala Val Asp Ile Ser
                245                 250                 255
Arg Asp Leu Ala Gly Val Ala Glu Glu Val His Val Ala Asp Arg Ser
                260                 265                 270
Ala Pro Ala Cys Thr Cys Lys Arg Gln Pro Gly Tyr Asp Asn Met Trp
                275                 280                 285
Leu His Ser Met Ile Asp His Ala Gln Glu Asp Gly Cys Val Val Phe
                290                 295                 300
Gln Asp Gly Ser Ser Ile Lys Ala Asp Val Ile Met His Cys Thr Gly
305                 310                 315                 320
Tyr Leu Tyr Asp Phe Pro Phe Leu Glu Asp Asp Ser Ala Ile Thr Val
                325                 330                 335
Asp Asp Asn Cys Val Asp Pro Leu Tyr Lys His Val Phe Pro Pro Glu
                340                 345                 350
Val Ala Pro His Leu Ser Phe Ile Gly Leu Pro Trp Lys Val Ile Pro
                355                 360                 365
Phe Pro Leu Phe Glu Leu Gln Ser Lys Trp Val Ala Gly Val Leu Ser
370                 375                 380
Gly Arg Val Lys Leu Pro Ser Ser Glu Glu Met Met Glu Asp Val Lys
385                 390                 395                 400
Ala Phe His Ser Lys Met Glu Ala Arg Gly Trp Pro Lys Arg Tyr Ala
                405                 410                 415
His Asn Phe Ser Asp Cys Gln Phe Glu Tyr Asp Asp Trp Leu Ala Glu
                420                 425                 430
Gln Cys Gly His Pro Pro Ile Glu Gln Trp Arg Lys Leu Met Tyr Ala
                435                 440                 445
Ala Asn Ser Glu Asn Lys Ala Ala Arg Pro Glu Ser Tyr Arg Asp Glu
450                 455                 460
Trp Asp Asp Asp His Leu Val Ala Glu Ala Ala Glu Asp Phe Lys Lys
```

Tyr Leu

<210> SEQ ID NO 17
<211> LENGTH: 1552
<212> TYPE: DNA
<213> ORGANISM: Vitis vinifera

<400> SEQUENCE: 17

| | | | | | |
|---|---|---|---|---|---|
| ctctactatc | ttcccatggc | gccctccatc | tccctgttca | atcacgtga | cgttgccgtc | 60 |
| atcggggctg | gcgctgccgg | tttagtcgcc | gcccgtgagc | tccgccgtga | aggccacaag | 120 |
| gtcgttgtct | tcgagcggga | acgccaagtg | ggtgggacct | gggtctacac | gcccacagtg | 180 |
| gagacggatc | cacttggctc | cgacccgtct | cgacacatag | tccactccag | cctctacgcc | 240 |
| tccctccgca | ccaacctccc | tagagaggtc | atgggttttc | tggactaccc | cttcgtatcc | 300 |
| actggtgaac | cacataggga | ccccagaagg | tttccgggtc | accgagaggt | ctcgctttat | 360 |
| ctcaaggatt | ttgcggttgg | gtttggactc | aatgaattaa | tccgcttcga | gacggaggta | 420 |
| gtttatgctg | gtttggtcga | ggatgagaag | tggagggtga | agtctagaag | cggaaacgat | 480 |
| gcggcaattg | atgtggagga | gattttttgat | gctgtggttg | tttgcaatgg | ccattacaca | 540 |
| gagccccgtc | ttgcagaaat | tcctggcatt | gatgcatggc | caggaaagca | tatgcatagt | 600 |
| cacaattatc | gtattcctga | gcccttcga | gatcaggtta | tagttttgat | agggggtgct | 660 |
| gcaagtgctg | tcgacatctc | tatggacatt | gctcaagttg | ctaaagcagt | tcatattgca | 720 |
| tctagatcag | ttgaggctgg | aatcttgaaa | aagttatctg | gcaatgccat | tgataacatg | 780 |
| tggcttcatc | ctatgataga | aagtgtccag | aaagatggta | ctgtgatatt | ttatgatggg | 840 |
| agtgtggttc | ttgctgatgt | aattctgcac | tgcacgggat | acaagtatca | tttcccttt | 900 |
| cttgacacca | gtggaattgt | gactgtggat | gacaatcgtg | tgggacctct | atacaagcat | 960 |
| atttttccac | cacatttggc | tccagggctt | tcctttgttg | gtttgccatg | gaaggtcctc | 1020 |
| cctttcccca | tgtttgaatt | ccaaagcaaa | tggatagcag | gtgctctctc | aggtcggatt | 1080 |
| ggactcccat | cgcaggagga | gatgatggca | gatgtttcag | cctttatttt | gtcactagaa | 1140 |
| gcttctgaca | caccaaagca | ctacactcac | aacttggctg | attctcaggt | aaatttgaac | 1200 |
| tcttatataa | gtgggttagg | atactgtcat | gttcattttt | cttactggtt | atctctcaaa | 1260 |
| gtaatgttga | aactgttctt | ggatggcatt | ttgcagtttg | agtatgatga | ttggcttgcc | 1320 |
| ttggaatgcg | ggattccagg | cgttgaagaa | tggagaaaga | aaatgtatga | agcaactgcc | 1380 |
| aagaacaaga | aggtccgacc | agacaaatac | cgcgacaaat | gggaagatga | agacttaatg | 1440 |
| ttggaagctc | agaaggactt | cgctggatgc | cgcctgaatg | gggctggtga | caattgaaac | 1500 |
| caacctcccc | tacaaaataa | gcaatgaaaa | aaaaaaaaa | gcccgataaa | ga | 1552 |

<210> SEQ ID NO 18
<211> LENGTH: 493
<212> TYPE: PRT
<213> ORGANISM: Vitis vinifera

<400> SEQUENCE: 18

Met Ala Pro Ser Ile Ser Leu Phe Lys Ser Arg Asp Val Ala Val Ile
1               5                   10                  15

Gly Ala Gly Ala Ala Gly Leu Val Ala Ala Arg Glu Leu Arg Arg Glu
            20                  25                  30

Gly His Lys Val Val Val Phe Glu Arg Glu Arg Gln Val Gly Gly Thr

-continued

```
            35                  40                  45
Trp Val Tyr Thr Pro Thr Val Glu Thr Asp Pro Leu Gly Ser Asp Pro
 50                  55                  60

Ser Arg His Ile Val His Ser Ser Leu Tyr Ala Ser Leu Arg Thr Asn
 65                  70                  75                  80

Leu Pro Arg Glu Val Met Gly Phe Leu Asp Tyr Pro Phe Val Ser Thr
                 85                  90                  95

Gly Glu Pro His Arg Asp Pro Arg Arg Phe Pro Gly His Arg Glu Val
            100                 105                 110

Ser Leu Tyr Leu Lys Asp Phe Ala Val Gly Phe Gly Leu Asn Glu Leu
            115                 120                 125

Ile Arg Phe Glu Thr Glu Val Val Tyr Ala Gly Leu Val Glu Asp Glu
        130                 135                 140

Lys Trp Arg Val Lys Ser Arg Ser Gly Asn Asp Ala Ala Ile Asp Val
145                 150                 155                 160

Glu Glu Ile Phe Asp Ala Val Val Val Cys Asn Gly His Tyr Thr Glu
                165                 170                 175

Pro Arg Leu Ala Glu Ile Pro Gly Ile Asp Ala Trp Pro Gly Lys His
            180                 185                 190

Met His Ser His Asn Tyr Arg Ile Pro Glu Pro Phe Arg Asp Gln Val
        195                 200                 205

Val Val Leu Ile Gly Gly Ala Ser Ala Val Asp Ile Ser Met Asp
210                 215                 220

Ile Ala Gln Val Ala Lys Ala Val His Ile Ala Ser Arg Ser Val Glu
225                 230                 235                 240

Ala Gly Ile Leu Lys Lys Leu Ser Gly Asn Ala Ile Asp Asn Met Trp
                245                 250                 255

Leu His Pro Met Ile Glu Ser Val Gln Lys Asp Gly Thr Val Ile Phe
            260                 265                 270

Tyr Asp Gly Ser Val Val Leu Ala Asp Val Ile Leu His Cys Thr Gly
        275                 280                 285

Tyr Lys Tyr His Phe Pro Phe Leu Asp Thr Ser Gly Ile Val Thr Val
290                 295                 300

Asp Asp Asn Arg Val Gly Pro Leu Tyr Lys His Ile Phe Pro Pro His
305                 310                 315                 320

Leu Ala Pro Gly Leu Ser Phe Val Gly Leu Pro Trp Lys Val Leu Pro
                325                 330                 335

Phe Pro Met Phe Glu Phe Gln Ser Lys Trp Ile Ala Gly Ala Leu Ser
            340                 345                 350

Gly Arg Ile Gly Leu Pro Ser Gln Glu Glu Met Met Ala Asp Val Ser
        355                 360                 365

Ala Phe Tyr Leu Ser Leu Glu Ala Ser Asp Thr Pro Lys His Tyr Thr
370                 375                 380

His Asn Leu Ala Asp Ser Gln Val Asn Leu Asn Ser Tyr Ile Ser Gly
385                 390                 395                 400

Leu Gly Tyr Cys His Val His Phe Ser Tyr Trp Leu Ser Leu Lys Val
                405                 410                 415

Met Leu Lys Leu Phe Leu Asp Gly Ile Leu Gln Phe Glu Tyr Asp Asp
            420                 425                 430

Trp Leu Ala Leu Glu Cys Gly Ile Pro Gly Val Glu Glu Trp Arg Lys
        435                 440                 445

Lys Met Tyr Glu Ala Thr Ala Lys Asn Lys Lys Val Arg Pro Asp Lys
450                 455                 460
```

Tyr Arg Asp Lys Trp Glu Asp Glu Asp Leu Met Leu Glu Ala Gln Lys
465                 470                 475                 480

Asp Phe Ala Gly Cys Arg Leu Asn Gly Ala Gly Asp Asn
                485                 490

<210> SEQ ID NO 19
<211> LENGTH: 1444
<212> TYPE: DNA
<213> ORGANISM: Vitis vinifera

<400> SEQUENCE: 19

| | | | | | | |
|---|---|---|---|---|---|---|
| ctctactatc | ttcccatggc | gccctccatc | tccctgttca | aatcacgtga | cgttgccgtc | 60 |
| atcggggctg | gcgctgccgg | tttagtcgcc | gcccgtgagc | tccgccgtga | aggccacaag | 120 |
| gtcgttgtct | tcgagcggga | acgccaagtg | ggtgggacct | gggtctacac | gcccacagtg | 180 |
| gagacggatc | cacttggctc | cgacccgtct | cgacacatag | tccactccag | cctctacgcc | 240 |
| tccctccgca | ccaacctccc | tagagaggtc | atgggttttc | tggactaccc | cttcgtatcc | 300 |
| actggtgaac | cacataggga | ccccagaagg | tttccgggtc | accgagaggt | ctcgctttat | 360 |
| ctcaaggatt | tgcggttgg | gtttggactc | aatgaattaa | tccgcttcga | gacggaggta | 420 |
| gtttatgctg | gtttggtcga | ggatgagaag | tggagggtga | agtctagaag | cggaaacgat | 480 |
| gcggcaattg | atgtggagga | gattttgat | gctgtggttg | tttgcaatgg | ccattacaca | 540 |
| gagccccgtc | ttgcagaaat | tcctggcatt | gatgcatggc | aggaaagca | tatgcatagt | 600 |
| cacaattatc | gtattcctga | gccctttcga | gatcaggttg | tagttttgat | agggggtgct | 660 |
| gcaagtgctg | tcgacatctc | tatggacatt | gctcaagttg | ctaaagcagt | tcatattgca | 720 |
| tctagatcag | ttgaggctgg | aatcttgaaa | aagttatctg | caatgccat | tgataacatg | 780 |
| tggcttcatc | ctatgataga | agtgtccag | aaagatggta | ctgtgatatt | ttatgatggg | 840 |
| agtgtggttc | ttgctgatgt | aattctgcac | tgcacgggat | acaagtatca | tttccctttt | 900 |
| cttgacacca | gtggaattgt | gactgtggat | gacaatcgtg | tgggacctct | atacaagcat | 960 |
| attttccac | cacatttggc | tccagggctt | tcctttgttg | gtttgccatg | gaaggtcctc | 1020 |
| cctttcccca | tgtttgaatt | ccaaagcaaa | tggatagcag | tgctctctc | aggtcggatt | 1080 |
| ggactcccat | cgcaggagga | gatgatggca | gatgtttcag | cctttattt | gtcactagaa | 1140 |
| gcttctgaca | caccaaagca | ctacactcac | aacttggctg | attctcagtt | tgagtatgat | 1200 |
| gattggcttg | ccttggaatg | cgggattcca | ggcgttgaag | aatggagaaa | gaaaatgtat | 1260 |
| gaagcaactg | ccaagaacaa | gaaggtccga | ccagacaaat | accgcgacaa | atgggaagat | 1320 |
| gaagacttaa | tgttggaagc | tcagaaggac | ttcgctggat | gccgcctgaa | tggggctggt | 1380 |
| gacaattgaa | accaacctcc | cctacaaaat | aagcaatgaa | aaaaaaaaa | aagcccgata | 1440 |
| aaga | | | | | | 1444 |

<210> SEQ ID NO 20
<211> LENGTH: 457
<212> TYPE: PRT
<213> ORGANISM: Vitis vinifera

<400> SEQUENCE: 20

Met Ala Pro Ser Ile Ser Leu Phe Lys Ser Arg Asp Val Ala Val Ile
1               5                   10                  15

Gly Ala Gly Ala Ala Gly Leu Val Ala Ala Arg Glu Leu Arg Arg Glu
            20                  25                  30

-continued

Gly His Lys Val Val Phe Glu Arg Glu Arg Gln Val Gly Gly Thr
         35                  40                  45

Trp Val Tyr Thr Pro Thr Val Glu Thr Asp Pro Leu Gly Ser Asp Pro
 50                  55                  60

Ser Arg His Ile Val His Ser Ser Leu Tyr Ala Ser Leu Arg Thr Asn
 65                  70                  75                  80

Leu Pro Arg Glu Val Met Gly Phe Leu Asp Tyr Pro Phe Val Ser Thr
                 85                  90                  95

Gly Glu Pro His Arg Asp Pro Arg Arg Phe Pro Gly His Arg Glu Val
            100                 105                 110

Ser Leu Tyr Leu Lys Asp Phe Ala Val Gly Phe Gly Leu Asn Glu Leu
            115                 120                 125

Ile Arg Phe Glu Thr Glu Val Val Tyr Ala Gly Leu Val Glu Asp Glu
            130                 135                 140

Lys Trp Arg Val Lys Ser Arg Ser Gly Asn Asp Ala Ala Ile Asp Val
145                 150                 155                 160

Glu Glu Ile Phe Asp Ala Val Val Cys Asn Gly His Tyr Thr Glu
                165                 170                 175

Pro Arg Leu Ala Glu Ile Pro Gly Ile Asp Ala Trp Pro Gly Lys His
            180                 185                 190

Met His Ser His Asn Tyr Arg Ile Pro Glu Pro Phe Arg Asp Gln Val
            195                 200                 205

Val Val Leu Ile Gly Gly Ala Ala Ser Ala Val Asp Ile Ser Met Asp
            210                 215                 220

Ile Ala Gln Val Ala Lys Ala Val His Ile Ala Ser Arg Ser Val Glu
225                 230                 235                 240

Ala Gly Ile Leu Lys Lys Leu Ser Gly Asn Ala Ile Asp Asn Met Trp
                245                 250                 255

Leu His Pro Met Ile Glu Ser Val Gln Lys Asp Gly Thr Val Ile Phe
            260                 265                 270

Tyr Asp Gly Ser Val Val Leu Ala Asp Val Ile Leu His Cys Thr Gly
            275                 280                 285

Tyr Lys Tyr His Phe Pro Phe Leu Asp Thr Ser Gly Ile Val Thr Val
            290                 295                 300

Asp Asp Asn Arg Val Gly Pro Leu Tyr Lys His Ile Phe Pro Pro His
305                 310                 315                 320

Leu Ala Pro Gly Leu Ser Phe Val Gly Leu Pro Trp Lys Val Leu Pro
                325                 330                 335

Phe Pro Met Phe Glu Phe Gln Ser Lys Trp Ile Ala Gly Ala Leu Ser
            340                 345                 350

Gly Arg Ile Gly Leu Pro Ser Gln Glu Glu Met Met Ala Asp Val Ser
            355                 360                 365

Ala Phe Tyr Leu Ser Leu Glu Ala Ser Asp Thr Pro Lys His Tyr Thr
            370                 375                 380

His Asn Leu Ala Asp Ser Gln Phe Glu Tyr Asp Asp Trp Leu Ala Leu
385                 390                 395                 400

Glu Cys Gly Ile Pro Gly Val Glu Glu Trp Arg Lys Lys Met Tyr Glu
                405                 410                 415

Ala Thr Ala Lys Asn Lys Lys Val Arg Pro Asp Lys Tyr Arg Asp Lys
            420                 425                 430

Trp Glu Asp Glu Asp Leu Met Leu Glu Ala Gln Lys Asp Phe Ala Gly
            435                 440                 445

Cys Arg Leu Asn Gly Ala Gly Asp Asn

<210> SEQ ID NO 21
<211> LENGTH: 1674
<212> TYPE: DNA
<213> ORGANISM: Vitis vinifera

<400> SEQUENCE: 21

```
ctccactttc ttcccatggc gccctccatc tccctgttca aatcacgtga cgttgccgtc      60
atcgggctg gcgctgccgg tttagttgcc gcccgtgagc tccgccgtga aggccacaag     120
gtcgttgtct tcgagcggga acgccaagtg ggtgggacct gggtctacac gcccacagtg     180
gagacggatc cacttggcgc cgacccgtct cgacacatag tccactccag cctctacgcc     240
tccctccgca ccaacctccc cagagaggtc atgggttttc tggactaccc cttcgtatcc     300
actggtgaac tcataggga ccccagaagg tttccgggtc accgagaggt ctcgctttat     360
ctcaaggatt ttgtggttgg gtttggactc aatgaattaa tccgcttcga dacggaggtg     420
gtttatgctg gtttggttga ggatgagaag tggggagtga agtctagaag cggaaacgat     480
gcggcaattg atgtggagga gattttttgat gctgtggttg tttgcaatgg ccattacaca     540
gagccccgtc ttgcagaaat tcctggcatt gatgcatggc aggaaagca tatgcatagt     600
cacaattatc gtactcctga gcccttttcga gatcaggttg tagttttgat agggagtgct     660
gcaagtgctg ttgacatctc tatggacatt gctcaagttg ctaaagcagt tcatattgca     720
tctagatcag ttgaggctgg aatcttggaa aagttatctg gcaatgctgt tgataacatg     780
tggcttcatc ctatgataga aagtgtccag aaagatggta ctgtgatatt ttatgatggg     840
agtgtggttc ttgctgatgt aattctgcac tgcacgggat acaagtatca tttccctttt     900
cttgacacca gtgggattgt gactgtggat gacaatcgtg tgggacctct atacaagcat     960
attttttccac acatttggc tccagggctt tcctttgttg gtctgctatg gaaggtcctc    1020
cctttcccca tgttttgaatt ccaaagcaaa tggatagcag tgctctctc aggtcggatt    1080
ggactcccat cgcaggagga gatgatggca gatgtttcag ccttttatt gtcacgagaa    1140
gcttctgaca caccaaagca ctacactcac aacttggctg attctcaggt aaatttgagc    1200
tcttatataa gtgggttagg atactgtcat tttcattttt cttactggtt atctctcaaa    1260
gtaatgttga aactgttctt ggatgctatt ttgcagtttg agtatgatga ttggcttgcc    1320
ttggaatgcg ggattccagg cgttgaagaa tggagaaaga aaatgtatca agcaactgct    1380
aagaataaga aggtccgacc agacaaatac cgcgacgaat gggaagatga agacttaacg    1440
ttggaagctc agaaggactt cgccagatgc cgcccgaatg ggggtggcga caattgaaac    1500
caacctcccc tacaaaataa gcaatgaaaa aaaaaaaaaa gcccgataaa gatggatctg    1560
gatattgtct tggttgagtc attcattgtt cttctcttga acttgaggt atattaattg    1620
aataatcagc catagcgtag ataattttt tttttatagc gattgttttg atcg          1674
```

<210> SEQ ID NO 22
<211> LENGTH: 457
<212> TYPE: PRT
<213> ORGANISM: Vitis vinifera

<400> SEQUENCE: 22

```
Met Ala Pro Ser Ile Ser Leu Phe Lys Ser Arg Asp Val Ala Val Ile
1               5                  10                  15

Gly Ala Gly Ala Ala Gly Leu Val Ala Ala Arg Glu Leu Arg Arg Glu
            20                  25                  30
```

-continued

Gly His Lys Val Val Phe Glu Arg Glu Arg Gln Val Gly Gly Thr
         35                  40                  45

Trp Val Tyr Thr Pro Thr Val Glu Thr Asp Pro Leu Gly Ala Asp Pro
 50                  55                  60

Ser Arg His Ile Val His Ser Ser Leu Tyr Ala Ser Leu Arg Thr Asn
 65                  70                  75                  80

Leu Pro Arg Glu Val Met Gly Phe Leu Asp Tyr Pro Phe Val Ser Thr
                 85                  90                  95

Gly Glu Pro His Arg Asp Pro Arg Arg Phe Pro Gly His Arg Glu Val
                100                 105                 110

Ser Leu Tyr Leu Lys Asp Phe Val Gly Phe Gly Leu Asn Glu Leu
            115                 120                 125

Ile Arg Phe Glu Thr Glu Val Val Tyr Ala Gly Leu Val Glu Asp Glu
            130                 135                 140

Lys Trp Gly Val Lys Ser Arg Ser Gly Asn Asp Ala Ala Ile Asp Val
145                 150                 155                 160

Glu Glu Ile Phe Asp Ala Val Val Val Cys Asn Gly His Tyr Thr Glu
                165                 170                 175

Pro Arg Leu Ala Glu Ile Pro Gly Ile Asp Ala Trp Pro Gly Lys His
            180                 185                 190

Met His Ser His Asn Tyr Arg Thr Pro Glu Pro Phe Arg Asp Gln Val
            195                 200                 205

Val Val Leu Ile Gly Ser Ala Ala Ser Ala Val Asp Ile Ser Met Asp
        210                 215                 220

Ile Ala Gln Val Ala Lys Ala Val His Ile Ala Ser Arg Ser Val Glu
225                 230                 235                 240

Ala Gly Ile Leu Glu Lys Leu Ser Gly Asn Ala Val Asp Asn Met Trp
                245                 250                 255

Leu His Pro Met Ile Glu Ser Val Gln Lys Asp Gly Thr Val Ile Phe
            260                 265                 270

Tyr Asp Gly Ser Val Val Leu Ala Asp Val Ile Leu His Cys Thr Gly
        275                 280                 285

Tyr Lys Tyr His Phe Pro Phe Leu Asp Thr Ser Gly Ile Val Thr Val
    290                 295                 300

Asp Asp Asn Arg Val Gly Pro Leu Tyr Lys His Ile Phe Pro Pro His
305                 310                 315                 320

Leu Ala Pro Gly Leu Ser Phe Val Gly Leu Leu Trp Lys Val Leu Pro
                325                 330                 335

Phe Pro Met Phe Glu Phe Gln Ser Lys Trp Ile Ala Gly Ala Leu Ser
            340                 345                 350

Gly Arg Ile Gly Leu Pro Ser Gln Glu Glu Met Met Ala Asp Val Ser
        355                 360                 365

Ala Phe Tyr Leu Ser Arg Glu Ala Ser Asp Thr Pro Lys His Tyr Thr
    370                 375                 380

His Asn Leu Ala Asp Ser Gln Phe Glu Tyr Asp Trp Leu Ala Leu
385                 390                 395                 400

Glu Cys Gly Ile Pro Gly Val Glu Glu Trp Arg Lys Lys Met Tyr Gln
                405                 410                 415

Ala Thr Ala Lys Asn Lys Lys Val Arg Pro Asp Lys Tyr Arg Asp Glu
            420                 425                 430

Trp Glu Asp Glu Asp Leu Thr Leu Glu Ala Gln Lys Asp Phe Ala Arg
        435                 440                 445

Cys Arg Pro Asn Gly Gly Gly Asp Asn
    450                 455

<210> SEQ ID NO 23
<211> LENGTH: 887
<212> TYPE: DNA
<213> ORGANISM: Gossypium hirsutum

<400> SEQUENCE: 23

| ctagatcagt | ggcggatgaa | acgtatatga | aacagcctgg | ttacgataat | ttgtggttcc | 60 |
| attccatgat | agatcatgca | catgaggatg | gcatggtggt | tttccgaaat | gggaaaacag | 120 |
| tgcttgctga | tctcattatg | cactgcactg | ggtacaagta | tcacttccct | ttccttgaca | 180 |
| caaaaggcat | tgtgactgtg | gacgataatc | gtcttggacc | actatacaag | cacgtctttc | 240 |
| ccccagcctt | agccccatac | ctttcattta | ttgggatacc | atggaagatt | gttccttttcc | 300 |
| ccttatttga | gtttcaaagc | aaatggatag | ccggtatttt | gtccggtcgt | attacacttc | 360 |
| catcacaaaa | ggaaatgatg | gaagatattc | aagcatttta | ctcggcactt | gaagattcta | 420 |
| gtataccaaa | acggtatact | cattgcattg | gtcaatctca | ggttgaatac | aataattggc | 480 |
| ttgctacaca | atgtggttgc | caaggtgttg | aaaaatggag | agaagcaatg | tattctatgg | 540 |
| cttcggagaa | tcggcgtctt | ctaccagaga | tgtaccgtga | tgaatgggat | gatcaccacc | 600 |
| tggtttcaga | agcttatgag | gatttcatta | agtacccttc | agcatcaaac | ctttagagac | 660 |
| aaaaaataaa | aataaaaatc | aatttacaat | ggtgaaggat | gtcattcacc | ctgttgtata | 720 |
| caacccgggt | ctgtaccgtg | gcagggtact | attctaccac | tagaccactg | gtgcttgtgc | 780 |
| gatgaaagtc | tcgatataca | taaatctagc | acaagagtta | ctaaacgaag | agaattgaag | 840 |
| gagaatcaac | tatatgaatt | ttattgaata | aaaaaaaaaa | aaaaaaa | | 887 |

<210> SEQ ID NO 24
<211> LENGTH: 217
<212> TYPE: PRT
<213> ORGANISM: Gossypium hirsutum

<400> SEQUENCE: 24

Arg Ser Val Ala Asp Glu Thr Tyr Met Lys Gln Pro Gly Tyr Asp Asn
1               5                   10                  15

Leu Trp Phe His Ser Met Ile Asp His Ala His Glu Asp Gly Met Val
            20                  25                  30

Val Phe Arg Asn Gly Lys Thr Val Leu Ala Asp Leu Ile Met His Cys
        35                  40                  45

Thr Gly Tyr Lys Tyr His Phe Pro Phe Leu Asp Thr Lys Gly Ile Val
    50                  55                  60

Thr Val Asp Asp Asn Arg Leu Gly Pro Leu Tyr Lys His Val Phe Pro
65                  70                  75                  80

Pro Ala Leu Ala Pro Tyr Leu Ser Phe Ile Gly Ile Pro Trp Lys Ile
                85                  90                  95

Val Pro Phe Pro Leu Phe Glu Phe Gln Ser Lys Trp Ile Ala Gly Ile
            100                 105                 110

Leu Ser Gly Arg Ile Thr Leu Pro Ser Gln Lys Glu Met Met Glu Asp
        115                 120                 125

Ile Gln Ala Phe Tyr Ser Ala Leu Glu Asp Ser Ser Ile Pro Lys Arg
    130                 135                 140

Tyr Thr His Cys Ile Gly Gln Ser Gln Val Glu Tyr Asn Asn Trp Leu
145                 150                 155                 160

Ala Thr Gln Cys Gly Cys Gln Gly Val Glu Lys Trp Arg Glu Ala Met
            165                 170                 175

Tyr Ser Met Ala Ser Glu Asn Arg Arg Leu Leu Pro Glu Met Tyr Arg
            180                 185                 190

Asp Glu Trp Asp Asp His His Leu Val Ser Glu Ala Tyr Glu Asp Phe
            195                 200                 205

Ile Lys Tyr Pro Ser Ala Ser Asn Leu
            210                 215

<210> SEQ ID NO 25
<211> LENGTH: 1262
<212> TYPE: DNA
<213> ORGANISM: Zea mays

<400> SEQUENCE: 25
atggaatgtt gttgctgggc tggctacagt acagtacagg tgcaggcttc attcctccag      60
tggcggcgga caacgccgaa cagacagaag aatactgtag agaagatcgt cgcacccacc     120
ggaggacgag acgggcccta ggcacaccac gcaatcagcc gccccgcgcc ccgcccgcg      180
gttggcgatg ttgccgtgac gtcttccagg gaggagaagc caacatcaca aactccacga     240
cgaataactg gcagtagaag ccgagaaggt aggcccgctc gttccaacat acaaactcc      300
acacggctct cctgtctccg ctgcccgctc cacctccctc catgccgtcg gcttccctcc     360
gcctcgccgt cgtcggcgcg ggcgcggcgg gcctggttgc cgcccgcgag ctacgccgcg     420
agggccatgc gcccgtcgtc ttcgagcgcg ccgccgccgt tggggcact tggctctaca     480
cgcctcccgc cacgtcctcc gacccgctcg gcgccgcggc gacgcattcc agcctctacg     540
catcgctccg caccaacctg ccacgcgaga ccatgggctt cctcgacttc cccttcgccg     600
ctggcgccgc gggctcccga cccccgcc ggtttcccgg cacgaggag gtgctccgct        660
acctggaggc gttcgcgcgc cggttcgacc tgctccggct cgtccgcttc gagacggagg     720
tgctcagtgt gaggagggaa gacggaggga ggtgggctgt gacgtcgagg aagctcgggg     780
ataaggggag cggcgaggag gagttctatg atgccgtcgt ggtctgcaat ggtcactaca     840
cggagccacg cctcgccgtc attcccgttt gagtatgatg attggctcgc tgagcaatgt     900
ggccatccac cagtcgaaga atggaggaag cagatgtatg ctgtaacttc aatgaacaag     960
gcagctcgtc ctgagagtta ccgtgatgaa tgggatgacg agcatctggt ggccgaagca    1020
aatgaatact tcaagaaatt cttgtaaatt cttcttact attctcatcc catattcttt      1080
cggcataccc gaggctgatc tcaactgcaa tatgcaaata tgaataacca tttaagtgat    1140
gtggattgga tacacttctg ggttagcatt tcatcgatca ttcgatcgat gtatatatat    1200
gagactgttc tggtagtaaa caatcttgta gtaaactgtg gattggtcat caattaacaa    1260
ca                                                                   1262

<210> SEQ ID NO 26
<211> LENGTH: 176
<212> TYPE: PRT
<213> ORGANISM: Zea mays

<400> SEQUENCE: 26

Met Pro Ser Ala Ser Leu Arg Leu Ala Val Val Gly Ala Gly Ala Ala
1               5                   10                  15

Gly Leu Val Ala Ala Arg Glu Leu Arg Arg Glu Gly His Ala Pro Val
            20                  25                  30

Val Phe Glu Arg Ala Ala Ala Val Gly Gly Thr Trp Leu Tyr Thr Pro

```
                 35                  40                  45
Pro Ala Thr Ser Ser Asp Pro Leu Gly Ala Ala Thr His Ser Ser
             50                  55                  60
Leu Tyr Ala Ser Leu Arg Thr Asn Leu Pro Arg Glu Thr Met Gly Phe
65                  70                  75                  80
Leu Asp Phe Pro Phe Ala Ala Gly Ala Gly Ser Arg Asp Pro Arg
                 85                  90                  95
Arg Phe Pro Gly His Glu Glu Val Leu Arg Tyr Leu Glu Ala Phe Ala
                100                 105                 110
Arg Arg Phe Asp Leu Leu Arg Leu Val Arg Phe Glu Thr Glu Val Leu
             115                 120                 125
Ser Val Arg Arg Glu Asp Gly Gly Arg Trp Ala Val Thr Ser Arg Lys
             130                 135                 140
Leu Gly Asp Lys Gly Ser Gly Glu Glu Glu Phe Tyr Asp Ala Val Val
145                 150                 155                 160
Val Cys Asn Gly His Tyr Thr Glu Pro Arg Leu Ala Val Ile Pro Val
                165                 170                 175
```

<210> SEQ ID NO 27
<211> LENGTH: 1359
<212> TYPE: DNA
<213> ORGANISM: Populus trichocarpa

<400> SEQUENCE: 27

```
atgcaaacat caaatgctac ttcgctcacc tctcgccacg tagctgtcat cggtgccggc    60
gccgccggtt tagtggcggc acgtgagctc cggcgtgaag gtcaccaagt ggttgtcttt   120
gagaaagata gccaaattgg tgggacatgg gtgtacactc cacaggtcga aaccgaccct   180
cttgggctag acccgacccg acacatcgtc cacaccagtt tatacaagtc cctccggacc   240
aacttgccga gagagtcgat gggctttatg gattatccat tcgtgacccg agcgggtgaa   300
gggagcgacc tagaaggttt cccgggtcat gcagaagtgt tgaagtatct gcaagatttt   360
gcaagggagt ttgggattga gaaatggtg aggtttgagt gtgaagtggt tagtgtggag   420
atggttgata tgagaaatt gaaagtgaag tgtaaaagga tgagacctga tggtggtgat   480
gatgatctgc tagatgaggt ttttgatgct gttgttgttt gtaatggaca tttcacatac   540
cctcgtattg ctgaaatccc tggcatcaac ttgtggcccg aatgcaaat acatagccat   600
aactatcgta ctcctgaact cttcaaggat aaagttgtaa ttttaattgg cagttctgca   660
agtgctattg atttatccct tgagattggt ggaattgcca agaggtgca cattgcatct   720
agatcagttg ccaatgatac atatgaaaag cgggctgaat gtgataata tggctacat    780
tctatgataa aaagcgcaca taagatggt tctgtggctt ccgagatgg taacactatc   840
gtcgctgata ttattctgca ttgcacaggg tacaagtatt acttcccatt cctcaaaacc   900
aatggcattg tgactgtgga tgacaatcgt gttggaccac tctacaagca tgttttccca   960
cccatttttg ccccgcagct ttcctttgtc ggactaccct acaggagttt acctttccca  1020
atctttgaaa ttcaaagcaa gtggatttct ggtgttctat ctgatcgaat tgtgctccct  1080
tcacaagagg acatgatgga agatgttaac acccttctact cgacacttga agattctggt  1140
gtgcctaagc atcacactca tagcatgggg gacacaatga ttgactacaa tgcttgggtt  1200
gcttctctgt gtcaatgtcc ttgctttgaa gaatggagag tacaaatgtt ctatgaaacg  1260
gccaagagat tgaacgccaa cccaaagaca tttcgcgatg aatgggaaga tgacaacctg  1320
gtcttgcaag cctgtgaaga tttcagcaaa tacatctga                         1359
```

<210> SEQ ID NO 28
<211> LENGTH: 452
<212> TYPE: PRT
<213> ORGANISM: Populus trichocarpa

<400> SEQUENCE: 28

```
Met Gln Thr Ser Asn Ala Thr Ser Leu Thr Ser Arg His Val Ala Val
1               5                   10                  15

Ile Gly Ala Gly Ala Ala Gly Leu Val Ala Ala Arg Glu Leu Arg Arg
            20                  25                  30

Glu Gly His Gln Val Val Val Phe Glu Lys Asp Ser Gln Ile Gly Gly
        35                  40                  45

Thr Trp Val Tyr Thr Pro Gln Val Glu Thr Asp Pro Leu Gly Leu Asp
    50                  55                  60

Pro Thr Arg His Ile Val His Thr Ser Leu Tyr Lys Ser Leu Arg Thr
65                  70                  75                  80

Asn Leu Pro Arg Glu Ser Met Gly Phe Met Asp Tyr Pro Phe Val Thr
                85                  90                  95

Arg Ala Gly Glu Gly Ser Asp Pro Arg Arg Phe Pro Gly His Ala Glu
            100                 105                 110

Val Leu Lys Tyr Leu Gln Asp Phe Ala Arg Glu Phe Gly Ile Glu Glu
        115                 120                 125

Met Val Arg Phe Glu Cys Glu Val Val Ser Val Glu Met Val Asp Asn
    130                 135                 140

Glu Lys Leu Lys Val Lys Cys Lys Arg Met Arg Pro Asp Gly Gly Asp
145                 150                 155                 160

Asp Asp Leu Leu Asp Glu Val Phe Asp Ala Val Val Cys Asn Gly
                165                 170                 175

His Phe Thr Tyr Pro Arg Ile Ala Glu Ile Pro Gly Ile Asn Leu Trp
            180                 185                 190

Pro Gly Met Gln Ile His Ser His Asn Tyr Arg Thr Pro Glu Leu Phe
        195                 200                 205

Lys Asp Lys Val Val Ile Leu Ile Gly Ser Ser Ala Ser Ala Ile Asp
    210                 215                 220

Leu Ser Leu Glu Ile Gly Gly Ile Ala Lys Glu Val His Ile Ala Ser
225                 230                 235                 240

Arg Ser Val Ala Asn Asp Thr Tyr Glu Lys Arg Ala Glu Cys Asp Asn
                245                 250                 255

Ile Trp Leu His Ser Met Ile Lys Ser Ala His Lys Asp Gly Ser Val
            260                 265                 270

Ala Phe Arg Asp Gly Asn Thr Ile Val Ala Asp Ile Ile Leu His Cys
        275                 280                 285

Thr Gly Tyr Lys Tyr Tyr Phe Pro Phe Leu Lys Thr Asn Gly Ile Val
    290                 295                 300

Thr Val Asp Asp Asn Arg Val Gly Pro Leu Tyr Lys His Val Phe Pro
305                 310                 315                 320

Pro Ile Phe Ala Pro Gln Leu Ser Phe Val Gly Leu Pro Tyr Arg Ser
                325                 330                 335

Leu Pro Phe Pro Ile Phe Glu Ile Gln Ser Lys Trp Ile Ser Gly Val
            340                 345                 350

Leu Ser Asp Arg Ile Val Leu Pro Ser Gln Glu Asp Met Met Glu Asp
        355                 360                 365

Val Asn Thr Phe Tyr Ser Thr Leu Glu Asp Ser Gly Val Pro Lys His
```

His Thr His Ser Met Gly Asp Thr Met Ile Asp Tyr Asn Ala Trp Val
385                 390                 395                 400

Ala Ser Leu Cys Gln Cys Pro Cys Phe Glu Glu Trp Arg Val Gln Met
            405                 410                 415

Phe Tyr Glu Thr Ala Lys Arg Leu Asn Ala Asn Pro Lys Thr Phe Arg
            420                 425                 430

Asp Glu Trp Glu Asp Asp Asn Leu Val Leu Gln Ala Cys Glu Asp Phe
            435                 440                 445

Ser Lys Tyr Ile
    450

<210> SEQ ID NO 29
<211> LENGTH: 1395
<212> TYPE: DNA
<213> ORGANISM: Populus trichocarpa

<400> SEQUENCE: 29

```
atgcaagcat caccgaattt gctctcctcc caccacgtcg ccgtgatcgg ggcaggagcc    60
gccggtctgg tggctgcacg tgagctccac cgagagggtc acaaagtggt ggtctttgag   120
aaagatgacc aagttggtgg tctctggatg tacgatcccc gtgtagaacc cgaccctctc   180
gggcttgacc taacccgacc tgttgttcac tcaagtctct acgagtctct caggaccaac   240
ttgccaaggg agacgatggg tttatggac tacccgtttg tgacccgaga gggtgaggga   300
agagacccga aaggtttcc gggtcataga gaagtgttga tgtatttgca ggattatgcc   360
agggaatttg ggattgaaga gatggtaagg tttgggtgtg aggtggtgaa tgtagagatg   420
attgatagtg ggaaatggaa agtgaagtca aaaaggaaga gacttgatga taatgataga   480
ggtgatgatt ttgctgatca tgaggatttt gatgctgttg ttgtttgcgt tggacattac   540
acccaacctc gtatcgctga aattcctggc atcaatttgt ggccggggaa gcagatacac   600
agccacaact atcgtattcc tgagcctttt agggatcaaa tcataatttt gataggagct   660
tctgcgagcg ctgctgatat atccgtggaa attgctggac ttgccaaaga ggttcacatt   720
gctcgtagat cggctgtaga tgatgataca tacgaaaaaa agcctggata tgataacata   780
tggcttcatt ccacgataga aagagcatgt gaagatggta ctgtcatttt ccgagatggc   840
agtgttatcc tagctgacgt tattctgcac tgcaccgggt acaaatatgg cttcccttt   900
ctgaaaactg atggcatcgt gactgtggat gacaatcgtg tggggccatt gtacaagcat   960
gttttccctc caatcttggc cccgtggctt tcctttgtcg ggatacccta ttggactttc  1020
cctttcccaa cgttcgaagt tcaaagcaag tggattgctg tgtttttatc aggtcgaatt  1080
gctcttcctt cacaagagga catggtgaa gatgttaaga tctactactc tgaacttgaa  1140
gcttctggtg tacctaagca tcacactcat aacttagctc attctacaaa tgactacaac  1200
atgtggcttg cctcccagtg tcagtgttca tgctttgaag aatggagaat tgaaatgtcc  1260
catgaaattc ttaagaactg gcgtgccagg ccaaatatgt atcgtgacga atgggacgac  1320
gaccacctga tcttgcaagc ccatgaagac ttcaacagac gcatctcaaa caaagccagt  1380
aatggtcata tctga                                                   1395
```

<210> SEQ ID NO 30
<211> LENGTH: 464
<212> TYPE: PRT
<213> ORGANISM: Populus trichocarpa

```
<400> SEQUENCE: 30

Met Gln Ala Ser Pro Asn Leu Leu Ser Ser His His Val Ala Val Ile
1               5                   10                  15

Gly Ala Gly Ala Ala Gly Leu Val Ala Ala Arg Glu Leu His Arg Glu
            20                  25                  30

Gly His Lys Val Val Phe Glu Lys Asp Asp Gln Val Gly Gly Leu
        35                  40                  45

Trp Met Tyr Asp Pro Arg Val Glu Pro Asp Pro Leu Gly Leu Asp Leu
    50                  55                  60

Thr Arg Pro Val Val His Ser Ser Leu Tyr Glu Ser Leu Arg Thr Asn
65                  70                  75                  80

Leu Pro Arg Glu Thr Met Gly Phe Met Asp Tyr Pro Phe Val Thr Arg
                85                  90                  95

Glu Gly Glu Gly Arg Asp Pro Arg Phe Pro Gly His Arg Glu Val
            100                 105                 110

Leu Met Tyr Leu Gln Asp Tyr Ala Arg Glu Phe Gly Ile Glu Glu Met
        115                 120                 125

Val Arg Phe Gly Cys Glu Val Val Asn Val Glu Met Ile Asp Ser Gly
    130                 135                 140

Lys Trp Lys Val Lys Ser Lys Arg Lys Arg Leu Asp Asp Asn Asp Arg
145                 150                 155                 160

Gly Asp Asp Phe Ala Asp His Glu Asp Phe Asp Ala Val Val Val Cys
                165                 170                 175

Val Gly His Tyr Thr Gln Pro Arg Ile Ala Glu Ile Pro Gly Ile Asn
        180                 185                 190

Leu Trp Pro Gly Lys Gln Ile His Ser His Asn Tyr Arg Ile Pro Glu
    195                 200                 205

Pro Phe Arg Asp Gln Ile Ile Ile Leu Ile Gly Ala Ser Ala Ser Ala
    210                 215                 220

Ala Asp Ile Ser Val Glu Ile Ala Gly Leu Ala Lys Glu Val His Ile
225                 230                 235                 240

Ala Arg Arg Ser Ala Val Asp Asp Thr Tyr Glu Lys Lys Pro Gly
                245                 250                 255

Tyr Asp Asn Ile Trp Leu His Ser Thr Ile Glu Arg Ala Cys Glu Asp
                260                 265                 270

Gly Thr Val Ile Phe Arg Asp Gly Ser Val Ile Leu Ala Asp Val Ile
            275                 280                 285

Leu His Cys Thr Gly Tyr Lys Tyr Gly Phe Pro Phe Leu Lys Thr Asp
    290                 295                 300

Gly Ile Val Thr Val Asp Asp Asn Arg Val Gly Pro Leu Tyr Lys His
305                 310                 315                 320

Val Phe Pro Pro Ile Leu Ala Pro Trp Leu Ser Phe Val Gly Ile Pro
                325                 330                 335

Tyr Trp Thr Phe Pro Phe Pro Thr Phe Glu Val Gln Ser Lys Trp Ile
            340                 345                 350

Ala Gly Val Leu Ser Gly Arg Ile Ala Leu Pro Ser Gln Glu Asp Met
        355                 360                 365

Val Glu Asp Val Lys Ile Tyr Tyr Ser Glu Leu Glu Ala Ser Gly Val
    370                 375                 380

Pro Lys His His Thr His Asn Leu Ala His Ser Thr Asn Asp Tyr Asn
385                 390                 395                 400

Met Trp Leu Ala Ser Gln Cys Gln Cys Ser Cys Phe Glu Glu Trp Arg
                405                 410                 415
```

Ile Glu Met Ser His Glu Ile Leu Lys Asn Trp Arg Ala Arg Pro Asn
              420                 425                 430

Met Tyr Arg Asp Glu Trp Asp Asp His Leu Ile Leu Gln Ala His
              435                 440                 445

Glu Asp Phe Asn Arg Arg Ile Ser Asn Lys Ala Ser Asn Gly His Ile
450                 455                 460

<210> SEQ ID NO 31
<211> LENGTH: 1680
<212> TYPE: DNA
<213> ORGANISM: Populus trichocarpa

<400> SEQUENCE: 31

```
tggggaccct gctgacgcta gcatttctca agtgtccaaa aaaccgaact ctcttcgaca    60
ggtcaccaca acaaccaccaa tcaaacattt atcaatgcca ccacctcaac ttcctccacc   120
aatctcccgc cacgtggcgg tgatcggtgc cggagccgcc ggcctcgtta gtgcccgtga   180
gctccggaga gagggtcatg atgttgtagt ctttgaaaga gacaaccaag taggtggcac   240
atgggtgtac aatccccgag tcgagcccga cccgttaagc ctcgacccga atcgacgcat   300
aattcactcg agcctctata gctccctccg gaccaacctc ccaagagaag taatgggttt   360
caaagattat ccctttatag caaaaaatga taaaaagaga gaccagagaa ggtttccggg   420
ccatcgagag gtgttgttgt atttgcagga ttttgcaagt gagtttggga ttgaagaaat   480
ggtgaggttt gatactgaag tggttcatgt ggggcctgtt gaggataata ttggaaagtg   540
gattgtgagg tctaaaagga aaataagtga tgatgatagg gaggttagtt ttggatttga   600
tgttgacgag gagatttatg atgctgttgt tatctgtaat ggacattaca ctgaacctcg   660
tattgctcaa ataccaggga tcagttcatg gccaggaaaa cagatgcata gccacaatta   720
tcgtactcct gagggctttc aagatcaagt ggcaattttg attggaagtt cagctagttc   780
tgatgatata tccagagaaa ttgctggagt tgctaaagag gtccatgttg cctcaagatc   840
agttgcggac gaaacatatc aagagcagcc tggatatgat aatatgtggc ttcattctat   900
gatagaaagt gtgcatgatg atggttctgt gatcttcaga aatgggagag ttgtcgttgc   960
tgacattatt ctacattgca ctgggtacaa gtatcacttc cctttttctag acaccaatgg  1020
cattgtgacc atggatgaaa atcgtgtggc cccctgtac aagcaagttt ttccaccagt   1080
tctggcccca tggctttcat tgttgggtt accgtggaag gttgtccctt ttcccttggt   1140
tgaacttcaa accaagtgga ttgctggtgt tttatcaggt catattgcac ttccgtcacc   1200
tgaggagatg atggaagatg ttaaagcctt ctatgagaca ctagaatctt ccaacaaacc   1260
caaacactac actcataatt tgggtggttg tcagttcgag tacgacaact ggcttgcttc   1320
tcagtgcggt tgcccaggga tcgaagaatg gagaaggcaa atgtatgatg cagctagcaa   1380
gagtaagcgg ctccggccag agatataccg tgatgaatgg gatgatgatg acctggtctt   1440
ggaagcctac ggggacttca caaagtacac ttgaaaaagt tgaagcaaca gctgcatctc   1500
tcaatggagg tgttcgaagg ataggaaagg aagacgataa attattaggc tggcctaatt   1560
gtcaacatct gaatttgtgg atcaatcat catcgttgtt aatttggact tgtatttcca   1620
tgattcgcag ttctttacgt gaataaagaa tcaatgaaga tatccatatc catatatgaa  1680
```

<210> SEQ ID NO 32
<211> LENGTH: 459
<212> TYPE: PRT
<213> ORGANISM: Populus trichocarpa

<400> SEQUENCE: 32

```
Met Pro Pro Pro Gln Leu Pro Pro Ile Ser Arg His Val Ala Val
1               5                   10                  15

Ile Gly Ala Gly Ala Ala Gly Leu Val Ser Ala Arg Glu Leu Arg Arg
                20                  25                  30

Glu Gly His Asp Val Val Phe Glu Arg Asp Asn Gln Val Gly Gly
            35                  40                  45

Thr Trp Val Tyr Asn Pro Arg Val Glu Pro Asp Leu Ser Leu Asp
    50                  55                  60

Pro Asn Arg Arg Ile Ile His Ser Ser Leu Tyr Ser Ser Leu Arg Thr
65                  70                  75                  80

Asn Leu Pro Arg Glu Val Met Gly Phe Lys Asp Tyr Pro Phe Ile Ala
                85                  90                  95

Lys Asn Asp Lys Lys Arg Asp Gln Arg Arg Phe Pro Gly His Arg Glu
                100                 105                 110

Val Leu Leu Tyr Leu Gln Asp Phe Ala Ser Glu Phe Gly Ile Glu Glu
            115                 120                 125

Met Val Arg Phe Asp Thr Glu Val Val His Val Gly Pro Val Glu Asp
130                 135                 140

Asn Ile Gly Lys Trp Ile Val Arg Ser Lys Arg Lys Ile Ser Asp Asp
145                 150                 155                 160

Asp Arg Glu Val Ser Phe Gly Phe Asp Val Asp Glu Glu Ile Tyr Asp
                165                 170                 175

Ala Val Val Ile Cys Asn Gly His Tyr Thr Glu Pro Arg Ile Ala Gln
            180                 185                 190

Ile Pro Gly Ile Ser Ser Trp Pro Gly Lys Gln Met His Ser His Asn
            195                 200                 205

Tyr Arg Thr Pro Glu Gly Phe Gln Asp Gln Val Ala Ile Leu Ile Gly
            210                 215                 220

Ser Ser Ala Ser Ser Asp Asp Ile Ser Arg Glu Ile Ala Gly Val Ala
225                 230                 235                 240

Lys Glu Val His Val Ala Ser Arg Ser Val Ala Asp Glu Thr Tyr Gln
                245                 250                 255

Glu Gln Pro Gly Tyr Asp Asn Met Trp Leu His Ser Met Ile Glu Ser
                260                 265                 270

Val His Asp Asp Gly Ser Val Ile Phe Arg Asn Gly Arg Val Val Val
            275                 280                 285

Ala Asp Ile Ile Leu His Cys Thr Gly Tyr Lys Tyr His Phe Pro Phe
290                 295                 300

Leu Asp Thr Asn Gly Ile Val Thr Met Asp Glu Asn Arg Val Ala Pro
305                 310                 315                 320

Leu Tyr Lys Gln Val Phe Pro Pro Val Leu Ala Pro Trp Leu Ser Phe
                325                 330                 335

Val Gly Leu Pro Trp Lys Val Val Pro Phe Pro Leu Val Glu Leu Gln
            340                 345                 350

Thr Lys Trp Ile Ala Gly Val Leu Ser Gly His Ile Ala Leu Pro Ser
            355                 360                 365

Pro Glu Glu Met Met Glu Asp Val Lys Ala Phe Tyr Gly Thr Leu Glu
            370                 375                 380

Ser Ser Asn Lys Pro Lys His Tyr Thr His Asn Leu Gly Gly Cys Gln
385                 390                 395                 400

Phe Glu Tyr Asp Asn Trp Leu Ala Ser Gln Cys Gly Cys Pro Gly Ile
```

```
                    405                 410                 415
Glu Glu Trp Arg Arg Gln Met Tyr Asp Ala Ala Ser Lys Ser Lys Arg
            420                 425                 430

Leu Arg Pro Glu Ile Tyr Arg Asp Glu Trp Asp Asp Asp Leu Val
        435                 440                 445

Leu Glu Ala Tyr Gly Asp Phe Thr Lys Tyr Thr
        450                 455
```

<210> SEQ ID NO 33
<211> LENGTH: 1347
<212> TYPE: DNA
<213> ORGANISM: Glycine max

<400> SEQUENCE: 33

```
atgatgtcca gcgcagtcac actcctgacg ccgcgccacg tggcagtgat cggcgcgggc       60
gccgccggcc tagtggcggc tcgggagctc cggcgagaag gcatcgcgt ggtggttttc       120
gagaaagggg aggaagtggg tggcatgtgg gtgtacagtc cggaggtgga ttcggatccg      180
ctgggtttgg aggcgaagcg agattagtc cactcgagcc tctacgattc gctccgaacg       240
aatctgtctc gggagagcat gagtttccga gattacccctt tcaggaggag ggaggggaaa    300
gggagggatt ctcgaaggtt cccgggtcac agagaggtgt tactgtactt gcaggatttc    360
gctgctgaat ttgaaatcgg agaattggtg aggtttggaa cggaggtttt gtttgctgga   420
ttggatcagt gtggaaagtg gaggctgact tcaacatcac cccatactca tcctgtggat    480
gagatttacg acgcccttat catttgcaac ggccattacg ttcagcctcg tcttcctcat   540
atccccggga ttaatgcatg gccagggaag cagatgcata gccataatta tagaacacct    600
gagccctttc aagatcaagt tgtagttcta attggtagtt ctgctagtgc ggttgatatc    660
tctcgagata tcgcaacagt tgctaaagaa gtccacattg cagctaggtc agttgaagaa   720
gataagctag gaaaggtgcc tggccatgag aatatgtggc ttcattctat gattgacagc    780
gttcatgaag atggtacagt ggtttttcaa gatggaaatg cagttggtgc tgacttcatc    840
atacattgca cagggtacaa gtatgatttt cccttccttg aaaccaatgg ggaggtgact    900
gtagatgaca accgtgtagg accactctac aaacatgttt cccaccagc cttggctcca     960
tggctttctt tgttgggtt gccttggaag gttgctccct ctccttgtt cgaactgcag    1020
agcaagtgga tagctggaat cttgtctaat cgcattgcac ttccttcgaa agaggagatg    1080
gctaaagacg ttgatgcttt ttactcatca cttgaagcct ctggcactcc taagcgttac   1140
actcataata tgggcattct tcagtgggac tacaataact ggattgcgga tcagtgtggg   1200
gttccttcta ttgaagaatg gagaaggcaa atgtatatag ccacatctaa gaacagggtg    1260
ctgcgacccg agtcttaccg tgacgagtgg gacgatgatg acttggttct gcaagctcaa    1320
caggattttg ccaattatct cacttga                                        1347
```

<210> SEQ ID NO 34
<211> LENGTH: 448
<212> TYPE: PRT
<213> ORGANISM: Glycine max

<400> SEQUENCE: 34

```
Met Met Ser Ser Ala Val Thr Leu Leu Thr Pro Arg His Val Ala Val
1               5                   10                  15

Ile Gly Ala Gly Ala Ala Gly Leu Val Ala Ala Arg Glu Leu Arg Arg
            20                  25                  30
```

```
Glu Gly His Arg Val Val Phe Glu Lys Gly Glu Val Gly Gly
         35                  40                  45

Met Trp Val Tyr Ser Pro Glu Val Asp Ser Asp Pro Leu Gly Leu Glu
 50                  55                  60

Ala Lys Arg Arg Leu Val His Ser Ser Leu Tyr Asp Ser Leu Arg Thr
 65                  70                  75                  80

Asn Leu Ser Arg Glu Ser Met Ser Phe Arg Asp Tyr Pro Phe Arg Arg
                 85                  90                  95

Arg Glu Gly Lys Gly Arg Asp Ser Arg Arg Phe Pro Gly His Arg Glu
            100                 105                 110

Val Leu Leu Tyr Leu Gln Asp Phe Ala Glu Phe Glu Ile Gly Glu
            115                 120                 125

Leu Val Arg Phe Gly Thr Glu Val Leu Phe Ala Gly Leu Asp Gln Cys
        130                 135                 140

Gly Lys Trp Arg Leu Thr Ser Thr Ser Pro His Thr His Pro Val Asp
145                 150                 155                 160

Glu Ile Tyr Asp Ala Leu Ile Ile Cys Asn Gly His Tyr Val Gln Pro
                165                 170                 175

Arg Leu Pro His Ile Pro Gly Ile Asn Ala Trp Pro Gly Lys Gln Met
            180                 185                 190

His Ser His Asn Tyr Arg Thr Pro Glu Pro Phe Gln Asp Gln Val Val
            195                 200                 205

Val Leu Ile Gly Ser Ser Ala Ser Val Asp Ile Ser Arg Asp Ile
        210                 215                 220

Ala Thr Val Ala Lys Glu Val His Ile Ala Ala Arg Ser Val Glu Glu
225                 230                 235                 240

Asp Lys Leu Gly Lys Val Pro Gly His Glu Asn Met Trp Leu His Ser
                245                 250                 255

Met Ile Asp Ser Val His Glu Asp Gly Thr Val Val Phe Gln Asp Gly
            260                 265                 270

Asn Ala Val Gly Ala Asp Phe Ile Ile His Cys Thr Gly Tyr Lys Tyr
            275                 280                 285

Asp Phe Pro Phe Leu Glu Thr Asn Gly Glu Val Thr Val Asp Asp Asn
290                 295                 300

Arg Val Gly Pro Leu Tyr Lys His Val Phe Pro Pro Ala Leu Ala Pro
305                 310                 315                 320

Trp Leu Ser Phe Val Gly Leu Pro Trp Lys Val Ala Pro Phe Ser Leu
                325                 330                 335

Phe Glu Leu Gln Ser Lys Trp Ile Ala Gly Ile Leu Ser Asn Arg Ile
            340                 345                 350

Ala Leu Pro Ser Lys Glu Glu Met Ala Lys Asp Val Asp Ala Phe Tyr
            355                 360                 365

Ser Ser Leu Glu Ala Ser Gly Thr Pro Lys Arg Tyr Thr His Asn Met
370                 375                 380

Gly Ile Leu Gln Trp Asp Tyr Asn Asn Trp Ile Ala Asp Gln Cys Gly
385                 390                 395                 400

Val Pro Ser Ile Glu Glu Trp Arg Arg Gln Met Tyr Ile Ala Thr Ser
                405                 410                 415

Lys Asn Arg Val Leu Arg Pro Glu Ser Tyr Arg Asp Glu Trp Asp Asp
            420                 425                 430

Asp Asp Leu Val Leu Gln Ala Gln Gln Asp Phe Ala Asn Tyr Leu Thr
            435                 440                 445
```

<210> SEQ ID NO 35
<211> LENGTH: 1703
<212> TYPE: DNA
<213> ORGANISM: Solanum lycopersicum

<400> SEQUENCE: 35

```
ggtggcgtga cactcccgct gcctttagta gatccgcccc cgctgaatgt ggtgaggaat      60
caaccaacaa atccacatgc aaagatactc aaatacaaaa ctcaaccaaa caaatccaca     120
tgcaaactca aacacaacat aaaatattac tttagtcatg attcttaaaa atgtcatctt     180
ttcaaaccaa ccttatactc gtacacttgt atgccatttg cccatgtctc aaaattcctc     240
caaaaacgtc gccgttattg gtgcgggctc cgcgggcctc gttgcggccc gagaactcca     300
acgagaaggt catagagtag ttgtattcga acgagaaaat caattaggag gcacatgggt     360
ttacacgccc gatacagaat ccgacccggt gggatcgac  ccgaatcggg agattgttca     420
ttcaagtctt tattcatctc tccgtgttaa tcttccccgg gaagtaatgg gttttgggga     480
ttacccgttt gtggccaaga aaagcccgg  tagagaccg  agaaggtatc cgagtcatgg     540
ggaggtgttg gagtatttga atgattttgc tgttgatttt gggattattg gggttgtgag     600
gtttgggatg gaagtggggt ttgtgggaaa gatggagaat ggaaaatgga aggttagttg     660
tagaaagagg gaaaatgatg atttgtttgc taatgaggag tatgatgctg ttgtaatatg     720
taatggacac tatactgaac caagaattgc tgatattcct ggaatcgaag tatggcctgg     780
aaagcaaatt cacagccaca actaccgtgt tcctgaccct tttcgagacc aagttgttgt     840
gctgataggt ggtgctgcaa gtgctactga tatctccagg gaaattgctg aagttgctaa     900
agaggtccac atttcttcta ggtcagctac tagtggagtt ccgatgaagc tgcctggtta     960
tgataatatt tggctccata atatgattga agctgttggc agtgatggtg gcgtgaattt    1020
tcaagatggg tcgaaaatcc ttgctgacat catcctacac tgcacagggt acaaatatca    1080
tttccttc ctcgaaacta acgggatagt gactgtggat gacaaccgtg ttggtccact    1140
ttacaagcac gttttcccac cagcctttgc accaagcctt tcatttgttg ggctgccttg    1200
gaaggttata ccattcttct gtgtgaatt  gcaaagcaag tggatcgctg gtgttttatc    1260
tggtcgaatt tctctcccat caaaggaaga tatgaatgct gatattgaag ctttctactc    1320
atccatggca gcctcttgca ttccaaaacg gtacactcac aatatggacg actctcagtt    1380
tgactacgat gattggttgg ctgctcagtg tggatctaca ccctttgaag aatggagaaa    1440
acaaatgtac ttaatctcaa gaaagaacaa aaggactctg cccgagacat atcgtgacga    1500
gtgggacgat gatgacttga tcattcaagc tcatgaagac ttcgtaaaat atattcctga    1560
actagctcaa gaacagaagc tctcaagatg attaattttg ttgttacatg aaaatatagc    1620
tgaataaatc gagaagtact gtaaataaac aggaaattac tcaattaatt tcaattgcaa    1680
ctcttgccac atgaaaaaaa aaa                                             1703
```

<210> SEQ ID NO 36
<211> LENGTH: 477
<212> TYPE: PRT
<213> ORGANISM: Solanum lycopersicum

<400> SEQUENCE: 36

```
Met Ile Leu Lys Asn Val Ile Phe Ser Asn Gln Pro Tyr Thr Arg Thr
1               5                   10                  15

Leu Val Cys His Leu Pro Met Ser Gln Asn Ser Ser Lys Asn Val Ala
            20                  25                  30
```

-continued

```
Val Ile Gly Ala Gly Ser Ala Gly Leu Val Ala Ala Arg Glu Leu Gln
         35                  40                  45
Arg Glu Gly His Arg Val Val Phe Glu Arg Glu Asn Gln Leu Gly
 50                  55                  60
Gly Thr Trp Val Tyr Thr Pro Asp Thr Glu Ser Asp Pro Val Gly Ile
 65                  70                  75                  80
Asp Pro Asn Arg Glu Ile Val His Ser Ser Leu Tyr Ser Ser Leu Arg
                 85                  90                  95
Val Asn Leu Pro Arg Glu Val Met Gly Phe Gly Asp Tyr Pro Phe Val
            100                 105                 110
Ala Lys Lys Lys Pro Gly Arg Asp Pro Arg Arg Tyr Pro Ser His Gly
        115                 120                 125
Glu Val Leu Glu Tyr Leu Asn Asp Phe Ala Val Asp Phe Gly Ile Ile
    130                 135                 140
Gly Val Val Arg Phe Gly Met Glu Val Gly Phe Val Gly Lys Met Glu
145                 150                 155                 160
Asn Gly Lys Trp Lys Val Ser Cys Arg Lys Arg Glu Asn Asp Asp Leu
                165                 170                 175
Phe Ala Asn Glu Glu Tyr Asp Ala Val Val Ile Cys Asn Gly His Tyr
            180                 185                 190
Thr Glu Pro Arg Ile Ala Asp Ile Pro Gly Ile Glu Val Trp Pro Gly
        195                 200                 205
Lys Gln Ile His Ser His Asn Tyr Arg Val Pro Asp Pro Phe Arg Asp
    210                 215                 220
Gln Val Val Leu Ile Gly Gly Ala Ala Ser Ala Thr Asp Ile Ser
225                 230                 235                 240
Arg Glu Ile Ala Glu Val Ala Lys Glu Val His Ile Ser Ser Arg Ser
                245                 250                 255
Ala Thr Ser Gly Val Pro Met Lys Leu Pro Gly Tyr Asp Asn Ile Trp
            260                 265                 270
Leu His Asn Met Ile Glu Ala Val Gly Ser Asp Gly Val Asn Phe
        275                 280                 285
Gln Asp Gly Ser Lys Ile Leu Ala Asp Ile Ile Leu His Cys Thr Gly
    290                 295                 300
Tyr Lys Tyr His Phe Pro Phe Leu Glu Thr Asn Gly Ile Val Thr Val
305                 310                 315                 320
Asp Asp Asn Arg Val Gly Pro Leu Tyr Lys His Val Phe Pro Pro Ala
                325                 330                 335
Phe Ala Pro Ser Leu Ser Phe Val Gly Leu Pro Trp Lys Val Ile Pro
            340                 345                 350
Phe Phe Leu Cys Glu Leu Gln Ser Lys Trp Ile Ala Gly Val Leu Ser
        355                 360                 365
Gly Arg Ile Ser Leu Pro Ser Lys Glu Asp Met Asn Ala Asp Ile Glu
    370                 375                 380
Ala Phe Tyr Ser Ser Met Ala Ala Ser Cys Ile Pro Lys Arg Tyr Thr
385                 390                 395                 400
His Asn Met Asp Asp Ser Gln Phe Asp Tyr Asp Asp Trp Leu Ala Ala
                405                 410                 415
Gln Cys Gly Ser Thr Pro Phe Glu Glu Trp Arg Lys Gln Met Tyr Leu
            420                 425                 430
Ile Ser Arg Lys Asn Lys Arg Thr Leu Pro Glu Thr Tyr Arg Asp Glu
        435                 440                 445
Trp Asp Asp Asp Asp Leu Ile Ile Gln Ala His Glu Asp Phe Val Lys
```

Tyr Ile Pro Glu Leu Ala Gln Glu Gln Lys Leu Ser Arg
465                 470                 475

<210> SEQ ID NO 37
<211> LENGTH: 4956
<212> TYPE: DNA
<213> ORGANISM: Solanum lycopersicum

<400> SEQUENCE: 37

| | | | | | |
|---|---|---|---|---|---|
| atgattctta | aaaatgtcat | cttttcaaac | caaccttata | ctcgtacact | tgtatgccat | 60 |
| ttgcccatgt | ctcaaaattc | ctccaaaaac | gtcgccgtta | ttggtgcggg | ctccgcgggc | 120 |
| ctcgttgcgg | cccgagaact | ccaacgagaa | ggtcatagag | tagttgtatt | cgaacgagaa | 180 |
| aatcaattag | gaggcacatg | ggtttacacg | cccgatacag | aatccgaccc | ggttgggatc | 240 |
| gacccgaatc | gggagattgt | tcattcaagt | ctttattcat | ctctccgtgt | taatcttccc | 300 |
| cgggaagtaa | tgggttttgg | ggattacccg | tttgtggcca | agaaaaagcc | cggtagagac | 360 |
| ccgagaaggt | atccgagtca | tggggaggtg | ttggagtatt | tgaatgattt | tgctgttgat | 420 |
| tttgggatta | ttggggttgt | gaggtttggg | atggaagtgg | ggtttgtggg | aaagatggag | 480 |
| aatggaaaat | ggaaggttag | ttgtagaaag | agggaaaatg | atgatttgtt | tgctaatgag | 540 |
| gagtatgatg | ctgttgtaat | atgtaatgga | cactatactg | aaccaagaat | tgctgatatt | 600 |
| cctggtaatt | tattgaaaaa | atttgatctt | tatgttgaat | aaagtaccat | atctccttta | 660 |
| gtcactatca | gatttttcga | aattatagat | tctttggtga | ataagtttta | atgctgatga | 720 |
| acttttttac | acttctgtgc | ttttagtaat | ccagttgtag | tacctttttt | ttagcttttg | 780 |
| tgcaccaggt | atttgataac | tttgtcctag | gacaaatgga | aaaaatgatt | taacttgac | 840 |
| attttattga | cctctagatc | atgcccttgg | gtgcatccaa | ttgtactttg | atctttagtt | 900 |
| gttcatactt | gaatagaata | ttatctccag | gagttatgtt | tctctttgta | gtaattgtag | 960 |
| attcgtttag | ttgagggaat | aagtctaaag | tgttgatgaa | atttttgttt | tagtgataac | 1020 |
| gtttgatatg | aagatttcaa | acatctgtac | attgtgctaa | tagttacatc | ctactaactg | 1080 |
| aaatataagt | tgtaccctgt | gggcgagcaa | agttgatctt | tttatgacaa | agatcaacct | 1140 |
| tcttcttttc | tctttctgtt | gttaaggcag | tgtccacgag | aaagaatgaa | tattgtacag | 1200 |
| ttaagattag | tcttttttca | gtggaaagat | tccagccttc | tttttggctt | agacataatt | 1260 |
| ttgtttctct | tatgtggcac | acatatgtta | agtaactttt | ttcctgttat | ggttttatac | 1320 |
| gttgtgagca | gttcaaaatt | tgattttta | tttgaattcg | cacatctttt | ccatttctg | 1380 |
| tcttgttcag | aacaaccata | taacaaagtg | aagtattctg | aaattcaata | gtgtcttttt | 1440 |
| taacttgaaa | gtgtggctga | aattttcttt | tttccatttt | aacatcattt | tgtggcaata | 1500 |
| ctatatgatt | agctctgaga | atatctgtga | gttgccaaac | tattgacata | ctaagtcaat | 1560 |
| atgcagtttt | tgaagtttct | aactggaggc | ctctagcctt | tcaggaatcg | aagtatggcc | 1620 |
| tggaaagcaa | attcacagcc | acaactaccg | tgttcctgac | ccttttcgag | accaagtatg | 1680 |
| tgtcaggttc | attgtttctt | taagatgttg | atgtttctga | actaatactg | ttgtgactga | 1740 |
| aatgcttgca | gttacttcaa | ttatgaattt | gctctactta | ttggaagcga | tcttttaatt | 1800 |
| acttactaaa | agtgttctgt | gatattctat | tgcgtgaagt | ttcaggccag | atataataga | 1860 |
| ttattgaatg | gaacgttctt | gaacaattct | attattgaat | tcttactttt | gcatgaagca | 1920 |
| ctggatgtat | gagtgatgac | gccaaaaaca | aagaaaactt | taaattttaa | atctaccttt | 1980 |

```
tcttcataaa tgaatattaa tagttagtac aagtatagta gtcctccttc ctaggaagct    2040
gtttagaaac gatggactat acagaaaatg aacattatgt atatatgctt atatgagcct    2100
aggtatgact tgggaaaaat gctccttggt tatatcagct tctaatattt gacaaatata    2160
gctcaagaaa tagtatcatc ttttgcctg atcccatggc ataactacca cccttttgtac    2220 caagttcaga gtaaatgaca atggtttttt tgccaggttg ttgtgctgat aggtggtgct    2280
gcaagtgcta ctgatatctc cagggaaatt gctgaagttg ctaaagaggt ccacatttct    2340
tctaggtcag ctactagtgg agttccgatg aagctgcctg ttatgataa tatttggctc    2400 cataatatgg taaagtggtt aataacttgt atattcatgt ggaggtttgt caacgcttga    2460
tgctgaatct gtacttcaca tcccctggat actatttaat gaaatcctct tacgtcataa    2520
aaagaaaaga aaaaaacaca tgatactgaa tcgtcagttg cgtaggaaaa aatttatact    2580
agctaatgat gcagattgaa gctgttggca gtgatggtgg cgtgaatttt caagatgggt    2640
cgaaaatcct tgctgacatc atcctacact gcacagggtg agtgattagt cctattgaaa    2700 cttcccttt cgcctacggt taaagaaaat gaaagaaagc tgacattgat agcctattct    2760 tttcttttt gaggaaatgt gaagggtaat gcatgcctgt ttttctgagg gtcataatga    2820
tatgaaattg cgaggtgaac tgaccttata aaatagcaaa agaatgatga ggtcaacaga    2880
tagttaaagt aggaactggc atgataaggg tagataatgg atccaaaggc aagaaacagt    2940
aaataaagta gttgatctgc tcttgagtag gcagtctcaa aatgaacctc ccatattata    3000
tgtttaattt cataattgta agcgtaaaaa gatattctaa tctataggtt agaaacagta    3060
aattaagtag ttaatctcct tgagtacgcc aatctaaaaa taaaccttgt agcctttaat    3120
acctttaggg gctgtttggt tgatgggatg gcatagacaa ggatatccca ttggattatt    3180
ttgtcttacc ttctacaagg gataaaaatat cccatcattt atactaaagt ggtgggtcaa    3240
aataatacct atcaccaatc acaagataaa ataaccacat gggatatatc gggattatta    3300
tcgttatccc atctaccaaa tgaccctaa gtataagctt aaaggaatgt ctattaatat    3360
tgtcttatcc cagacccctaa aaagattgaa gaatgtctat taatattttc atagcctata    3420
agaacatcag aaatccagta gttatctatt taagtattac agtttagtga ggcagatttg    3480
gttagatatt gtgaaggtag ccaaagacta aggagtgtaa attttctgt tccgggttac    3540 agaaacgaag ggaagttatc ttcagctaaa atgaatacta atttatgtga gtttggtagt    3600
acaggcctcc taattcatag taagatgtct ctaaccttta cgattgtaat aaaaaataat    3660
tgctagtaat cttacaaaat aatcaaattg atgggagaat aagtatcatg aatgtttctt    3720
atctttgttt cccaggtaca aatatcattt tcctttcctc gaaactaacg ggatagtgac    3780
tgtggatgac aaccgtgttg gtccactta caagcacgtt ttcccaccag cctttgcacc    3840
aagcctttca tttgttgggc tgccttggaa ggtaaaattt agagggtttg tgctggggtt    3900
tatagattta cattttaaat ggtggacttg aacgtaatat ttgtcctggt tggcaccagg    3960
ttataccatt cttcttgtgt gaattgcaaa gcaagtggat cgctggtgtt ttatctggtc    4020
gaatttctct cccatcaaag gaagatatga atgctgatat tgaagctttc tactcatcca    4080
tggcagcctc ttgcattcca aaacggtaca ctcacaatat ggacgactct caggtataac    4140
atctgccaaa aaaccttgtc gaatggtttt aggttttttg ttttgttcta tgggtaaagt    4200
gtggtagaaa cagctgaaca cttcatgcct acccgtaaca tacagaagtt cttggttaca    4260
ccatcttagt taagttagaa aagaaaagaa agaaacagaa aaaagaatcg aaactgaaga    4320
attagagtgt agtaagcttc tgtcattaat tcagtgcacg atcctgattt agttggggtt    4380
```

```
ccaatgtggg cttcaaacac cgggtgggaa acccaaaaag aaagaaaaag aaagaaagcg    4440
agtgtagagc ttctgtcatt gattaacata gactgctaat atgaacacat ccaagttggg    4500
ggttctttag cacggtgaca ttatagtcgt cctttatgag atatgaatct ctgagcgtgt    4560
tgagcatgtt tactttctgt atatgctggc taaacaagat tgttgcacag caacaccaaa    4620
ccaaatggct ttgccccttt tatacaagag tgtagctctg gtgttcatta tgttatgtat    4680
tatagattac caaaacagta ttacatatag ttcgtgcctc gtaaataatc cctctcttta    4740
cagtttgact acgatgattg gttggctgct cagtgtggat ctacaccctt tgaagaatgg    4800
agaaaacaaa tgtacttaat ctcaagaaag aacaaaagga ctctgcccga gacatatcgt    4860
gacgagtggg acgatgatga cttgatcatt caagctcatg aagacttcgt aaaatatatt    4920
cctgaactag ctcaagaaca gaagctctca agatga                              4956
```

<210> SEQ ID NO 38
<211> LENGTH: 213
<212> TYPE: PRT
<213> ORGANISM: Solanum lycopersicum

<400> SEQUENCE: 38

```
Met Ile Leu Lys Asn Val Ile Phe Ser Asn Gln Pro Tyr Thr Arg Thr
1               5                   10                  15

Leu Val Cys His Leu Pro Met Ser Gln Asn Ser Ser Lys Asn Val Ala
            20                  25                  30

Val Ile Gly Ala Gly Ser Ala Gly Leu Val Ala Ala Arg Glu Leu Gln
        35                  40                  45

Arg Glu Gly His Arg Val Val Val Phe Glu Arg Glu Asn Gln Leu Gly
    50                  55                  60

Gly Thr Trp Val Tyr Thr Pro Asp Thr Glu Ser Asp Pro Val Gly Ile
65                  70                  75                  80

Asp Pro Asn Arg Glu Ile Val His Ser Ser Leu Tyr Ser Ser Leu Arg
                85                  90                  95

Val Asn Leu Pro Arg Glu Val Met Gly Phe Gly Asp Tyr Pro Phe Val
            100                 105                 110

Ala Lys Lys Lys Pro Gly Arg Asp Pro Arg Arg Tyr Pro Ser His Gly
        115                 120                 125

Glu Val Leu Glu Tyr Leu Asn Asp Phe Ala Val Asp Phe Gly Ile Ile
    130                 135                 140

Gly Val Val Arg Phe Gly Met Glu Val Gly Phe Val Gly Lys Met Glu
145                 150                 155                 160

Asn Gly Lys Trp Lys Val Ser Cys Arg Lys Arg Glu Asn Asp Asp Leu
                165                 170                 175

Phe Ala Asn Glu Glu Tyr Asp Ala Val Val Ile Cys Asn Gly His Tyr
            180                 185                 190

Thr Glu Pro Arg Ile Ala Asp Ile Pro Gly Asn Leu Leu Lys Lys Phe
        195                 200                 205

Asp Leu Tyr Val Glu
    210
```

<210> SEQ ID NO 39
<211> LENGTH: 2044
<212> TYPE: DNA
<213> ORGANISM: Homo sapiens

<400> SEQUENCE: 39

| | | |
|---|---|---|
| caggacgtag acacacagaa gaaaagaaga caaagaacgg gttaccatgg ggaagaaagt | 60 | |
| ggccatcatt ggagctggtg tgagtggctt ggcctccatc aggagctgtc tggaagaggg | 120 | |
| gctggagccc acctgctttg agaagagcaa tgacattggg ggcctgtgga aattttcaga | 180 | |
| ccatgcagag gagggcaggg ctagcattta caaatcagtc tttccaact cttccaaaga | 240 | |
| gatgatgtgt ttcccagact tcccatttcc cgatgacttc cccaacttta tgcacaacag | 300 | |
| caagatccag gaatatatca ttgcatttgc caaagaaaag aacctcctga agtacataca | 360 | |
| atttaagaca tttgtatcca gtgtaaataa acatcctgat tttgcaacta ctggccagtg | 420 | |
| ggatgttacc actgaaaggg atggtaaaaa agaatcggct gtctttgatg ctgtaatggt | 480 | |
| ttgttccgga catcatgtgt atcccaacct accaaaagag tcctttccag gactaaacca | 540 | |
| ctttaaaggc aaatgcttcc acagcaggga ctataaagaa ccaggtgtat tcaatggaaa | 600 | |
| gcgtgtcctg gtggttggcc tggggaattc gggctgtgat attgccacag aactcagccg | 660 | |
| cacagcagaa caggtcatga tcagttccag aagtggctcc tgggtgatga gccgggtctg | 720 | |
| ggacaatggt tatccttggg acatgctgct cgtcactcga tttggaaccct tcctcaagaa | 780 | |
| caatttaccg acagccatct ctgactggtt gtacatgaag cagatgaatg caagattcaa | 840 | |
| gcatgaaaac tatggcttga tgcctttaaa tggagtcctg aggaaagagc ctgtatttaa | 900 | |
| cgatgagctc ccagcaagca ttctgtgtgg cattgtgtcc gtaaagccta acgtgaagga | 960 | |
| attcacagag acctcggcca tttttgagga tgggaccata tttgagggca ttgactgtgt | 1020 | |
| aatctttgca cagggtata gttttgccta cccttcctt gatgagtcta tcatcaaaag | 1080 | |
| cagaaacaat gagatcattt tatttaaagg agtatttcct cctctacttg agaagtcaac | 1140 | |
| catagcagtg attggctttg tccagtccct tgggctgcc attcccacag ttgacctcca | 1200 | |
| gtcccgctgg gcagcacaag taataaaggg aacttgtact ttgccttcta tggaagacat | 1260 | |
| gatgaatgat attaatgaga aaatggagaa aaagcgcaaa tggtttggca aaagcgagac | 1320 | |
| catacagaca gattacattg tttatatgga tgaactctcc tccttcattg gggcaaagcc | 1380 | |
| caacatccca tggctgtttc tcacagatcc caaattggcc atggaagttt attttggccc | 1440 | |
| ttgtagtccc taccagtttta ggctggtggg cccaggcag tggccaggag ccagaaatgc | 1500 | |
| catactgacc cagtgggacc ggtcgttgaa acccatgcag acacgagtgg tcgggagact | 1560 | |
| tcagaagcct tgcttctttt tccattggct gaagctcttt gcaattccta ttctgttaat | 1620 | |
| cgctgttttc cttgtgttga cctaatcatc attttctcta ggatttctga agttactga | 1680 | |
| caatacccag acaggggctt tgctatttaa aaattaaaat tttcacacca cctgcttttc | 1740 | |
| tattcagcat cttttgcagt actctgtaga cattagtcag taatacagtg ttatttctag | 1800 | |
| gctctgaaat agccacttta agaatcatgt catgatctta agagagcact aatcatttct | 1860 | |
| gtttgagttc cactaacact tcaaaatcag aactatgttc tttatatcta acttaaatca | 1920 | |
| tttcctgaaa cattttgaca tgattccttt ttccttttaa acaatgtatg aaagatgtat | 1980 | |
| tttaaatcta aataaagagc aaattaagca gaataaaaaa aaaaaaaaa aaaaaaaaa | 2040 | |
| aaaa | 2044 | |

<210> SEQ ID NO 40
<211> LENGTH: 532
<212> TYPE: PRT
<213> ORGANISM: Homo sapiens

<400> SEQUENCE: 40

Met Gly Lys Lys Val Ala Ile Ile Gly Ala Gly Val Ser Gly Leu Ala

-continued

```
1               5                   10                  15
Ser Ile Arg Ser Cys Leu Glu Glu Gly Leu Glu Pro Thr Cys Phe Glu
                20                  25                  30
Lys Ser Asn Asp Ile Gly Gly Leu Trp Lys Phe Ser Asp His Ala Glu
                35                  40                  45
Glu Gly Arg Ala Ser Ile Tyr Lys Ser Val Phe Ser Asn Ser Ser Lys
                50                  55                  60
Glu Met Met Cys Phe Pro Asp Phe Pro Phe Pro Asp Asp Phe Pro Asn
 65                 70                  75                  80
Phe Met His Asn Ser Lys Ile Gln Glu Tyr Ile Ile Ala Phe Ala Lys
                85                  90                  95
Glu Lys Asn Leu Leu Lys Tyr Ile Gln Phe Lys Thr Phe Val Ser Ser
                100                 105                 110
Val Asn Lys His Pro Asp Phe Ala Thr Thr Gly Gln Trp Asp Val Thr
                115                 120                 125
Thr Glu Arg Asp Gly Lys Lys Glu Ser Ala Val Phe Asp Ala Val Met
                130                 135                 140
Val Cys Ser Gly His His Val Tyr Pro Asn Leu Pro Lys Glu Ser Phe
145                 150                 155                 160
Pro Gly Leu Asn His Phe Lys Gly Lys Cys Phe His Ser Arg Asp Tyr
                165                 170                 175
Lys Glu Pro Gly Val Phe Asn Gly Lys Arg Val Leu Val Val Gly Leu
                180                 185                 190
Gly Asn Ser Gly Cys Asp Ile Ala Thr Glu Leu Ser Arg Thr Ala Glu
                195                 200                 205
Gln Val Met Ile Ser Ser Arg Ser Gly Ser Trp Val Met Ser Arg Val
                210                 215                 220
Trp Asp Asn Gly Tyr Pro Trp Asp Met Leu Leu Val Thr Arg Phe Gly
225                 230                 235                 240
Thr Phe Leu Lys Asn Asn Leu Pro Thr Ala Ile Ser Asp Trp Leu Tyr
                245                 250                 255
Met Lys Gln Met Asn Ala Arg Phe Lys His Glu Asn Tyr Gly Leu Met
                260                 265                 270
Pro Leu Asn Gly Val Leu Arg Lys Glu Pro Val Phe Asn Asp Glu Leu
                275                 280                 285
Pro Ala Ser Ile Leu Cys Gly Ile Val Ser Val Lys Pro Asn Val Lys
                290                 295                 300
Glu Phe Thr Glu Thr Ser Ala Ile Phe Glu Asp Gly Thr Ile Phe Glu
305                 310                 315                 320
Gly Ile Asp Cys Val Ile Phe Ala Thr Gly Tyr Ser Phe Ala Tyr Pro
                325                 330                 335
Phe Leu Asp Glu Ser Ile Ile Lys Ser Arg Asn Asn Glu Ile Ile Leu
                340                 345                 350
Phe Lys Gly Val Phe Pro Pro Leu Leu Glu Lys Ser Thr Ile Ala Val
                355                 360                 365
Ile Gly Phe Val Gln Ser Leu Gly Ala Ala Ile Pro Thr Val Asp Leu
                370                 375                 380
Gln Ser Arg Trp Ala Ala Gln Val Ile Lys Gly Thr Cys Thr Leu Pro
385                 390                 395                 400
Ser Met Glu Asp Met Met Asn Asp Ile Asn Glu Lys Met Glu Lys Lys
                405                 410                 415
Arg Lys Trp Phe Gly Lys Ser Glu Thr Ile Gln Thr Asp Tyr Ile Val
                420                 425                 430
```

```
                Tyr Met Asp Glu Leu Ser Ser Phe Ile Gly Ala Lys Pro Asn Ile Pro
                        435                 440                 445

Trp Leu Phe Leu Thr Asp Pro Lys Leu Ala Met Glu Val Tyr Phe Gly
                    450                 455                 460

Pro Cys Ser Pro Tyr Gln Phe Arg Leu Val Gly Pro Gly Gln Trp Pro
                465                 470                 475                 480

Gly Ala Arg Asn Ala Ile Leu Thr Gln Trp Asp Arg Ser Leu Lys Pro
                                485                 490                 495

Met Gln Thr Arg Val Val Gly Arg Leu Gln Lys Pro Cys Phe Phe
                            500                 505                 510

His Trp Leu Lys Leu Phe Ala Ile Pro Ile Leu Leu Ile Ala Val Phe
                        515                 520                 525

Leu Val Leu Thr
                        530

<210> SEQ ID NO 41
<211> LENGTH: 2190
<212> TYPE: DNA
<213> ORGANISM: Oryctolagus cuniculus

<400> SEQUENCE: 41
tcacagcatc ggcggctcg cagcggcggg acatcgcgga cgttcgcgca ggcggactag        60
tgacttccac gcaagacagg cgacgctgcc gggagaccat ggccgggaaa agagtggcgg      120
tgattggggc gggagcgagc gggctggctt gcatcaagtg ctgcctggaa gagggcttgg      180
agcccgtctg cttcgaaagg accgacgaca tcggaggtct gtggaggttc caggaaagtc      240
ccgacgaagg aagggccagt atctacaaat ccgtgatcat caacacctcc aaggagatga      300
tgtgcttcag tgactacccc atcccggatc attttcctaa cttcatgcac aactcccagg      360
tcctggagta cttcaggatg tacgccaaag aatttggtct tctgaagtat attcagttta      420
agaccactgt gtgcagtgtg aagaagcggc ctgatttctc cacgtcgggc aatgggagg      480 tgctgactga gtgcgaaggg aaaaaggaga gtgctgtctt cgatggggtc ctggtttgca      540
ccggccatca caccagtgct cacctgccac tggaaagctt ccctgggatt gagaagttca      600
aagggcagta cttgcacagt cgagactata agaacccaga gaaattcact ggaaagagag      660
tcattgtcat tggcattggg aattctggag gggacctggc tgtggagatc agccacacag      720
ccaagcaggt cttcctcagc accaggagag gggcttggat catgaatcgt gtcggcgacc      780
atggatatcc tattgatata ctgctgtctt ctcgatttag tcaattttg aagaagatta      840 ctggtgaaac aatagcaaat tcatttttgg aaagaaagat gaaccaaagg tttgaccatg      900
caatgtttgg tctgaagcct aaacacagag ctttgagtca cacccaaca gtaaatgatg      960 acctgccaaa tcgtatcatt tctggctctg tcaagatcaa aggaaatgtg aaggaattca     1020
cagaaacagc tgccatattt gaagatggct ccagggagga tgacattgat gctgttattt     1080
ttgccacagg ctatagcttt ccttttcctt tcttgaaga ctctgtcaaa gtggtgaaaa     1140
acaaggtatc tctgtataaa aaggtcttcc cccctaacct ggaaaagcca actcttgcaa     1200
tcataggctt gatccagccc ctgggagcca ttatgcccat ttcagagctc aagcacgat     1260 gggccaccct agtgttaaa gggctaaga ctttaccctc acaaagtgaa atgatgacag     1320
aaatatctca ggttcaagag aaaatggcaa aaggtatgt ggagagccaa cgccatacca     1380
ttcagggaga ctacatagag accatggaag aaattgctga tttggtgggg gtcaggccaa     1440
atttgctgtc tctggctttc accgacccca ggctggcatt acaattactt tgggacct     1500
```

```
gtactccagt ccattatcgt ctccagggcc gtggaaagtg ggatggggct cggaaaacca    1560
tccttaccgt agaagatcgg atcaggaagc ctctgatgac aagagtcacg gaaagcagta    1620
actctgtgac ctcgatgatg acaatgggca agtttatgct agctattgct ttcttagcca    1680
tagctgtggt ttattttag ctgtccctttt gtcattgcct ctgctttcat tgggaagctt    1740
aacttagaga gagataccttt cagaatttta caagatcaaa tgaccctcct ctttcaaatt    1800
gccccatttc tctttcaaaa gcattaattc tctcttcatt ttcctacagt gagatccaag    1860
cttttcattt gcactaagca tctcctcacc tctcatgagc cttcactttc tctctccaga    1920
gcagctcggg tactcttagt catctttgta tgtccctagc agagtagttg acatttggct    1980
ggtgtttaac caatgtttgg tgttgtggct caaagtctgt ttttgtatgg gaaatgactg    2040
actgtataac tctgcttggg atggaatttg gttttccatt attttttgtct ttaacattat    2100 aacaaatgta tgtttcctga gaaataagat taataatgac cttcgtaatt gtagacaaat    2160
aaatacttaa gttactttgt tctacatgcc                                    2190

<210> SEQ ID NO 42
<211> LENGTH: 533
<212> TYPE: PRT
<213> ORGANISM: Oryctolagus cuniculus

<400> SEQUENCE: 42

Met Ala Gly Lys Arg Val Ala Val Ile Gly Ala Gly Ala Ser Gly Leu
1               5                   10                  15

Ala Cys Ile Lys Cys Cys Leu Glu Glu Gly Leu Glu Pro Val Cys Phe
            20                  25                  30

Glu Arg Thr Asp Asp Ile Gly Gly Leu Trp Arg Phe Gln Glu Ser Pro
        35                  40                  45

Asp Glu Gly Arg Ala Ser Ile Tyr Lys Ser Val Ile Ile Asn Thr Ser
    50                  55                  60

Lys Glu Met Met Cys Phe Ser Asp Tyr Pro Ile Pro Asp His Phe Pro
65                  70                  75                  80

Asn Phe Met His Asn Ser Gln Val Leu Glu Tyr Phe Arg Met Tyr Ala
                85                  90                  95

Lys Glu Phe Gly Leu Leu Lys Tyr Ile Gln Phe Lys Thr Thr Val Cys
            100                 105                 110

Ser Val Lys Lys Arg Pro Asp Phe Ser Thr Ser Gly Gln Trp Glu Val
        115                 120                 125

Leu Thr Glu Cys Glu Gly Lys Lys Glu Ser Ala Val Phe Asp Gly Val
    130                 135                 140

Leu Val Cys Thr Gly His His Thr Ser Ala His Leu Pro Leu Glu Ser
145                 150                 155                 160

Phe Pro Gly Ile Glu Lys Phe Lys Gly Gln Tyr Leu His Ser Arg Asp
                165                 170                 175

Tyr Lys Asn Pro Glu Lys Phe Thr Gly Lys Arg Val Ile Val Ile Gly
            180                 185                 190

Ile Gly Asn Ser Gly Gly Asp Leu Ala Val Glu Ile Ser His Thr Ala
        195                 200                 205

Lys Gln Val Phe Leu Ser Thr Arg Arg Gly Ala Trp Ile Met Asn Arg
    210                 215                 220

Val Gly Asp His Gly Tyr Pro Ile Asp Ile Leu Leu Ser Ser Arg Phe
225                 230                 235                 240

Ser Gln Phe Leu Lys Lys Ile Thr Gly Glu Thr Ile Ala Asn Ser Phe
```

```
                245                 250                 255
Leu Glu Arg Lys Met Asn Gln Arg Phe Asp His Ala Met Phe Gly Leu
            260                 265                 270
Lys Pro Lys His Arg Ala Leu Ser Gln His Pro Thr Val Asn Asp Asp
            275                 280                 285
Leu Pro Asn Arg Ile Ile Ser Gly Ser Val Lys Ile Lys Gly Asn Val
        290                 295                 300
Lys Glu Phe Thr Glu Thr Ala Ala Ile Phe Glu Asp Gly Ser Arg Glu
305                 310                 315                 320
Asp Asp Ile Asp Ala Val Ile Phe Ala Thr Gly Tyr Ser Phe Ser Phe
                325                 330                 335
Pro Phe Leu Glu Asp Ser Val Lys Val Lys Asn Lys Val Ser Leu
            340                 345                 350
Tyr Lys Lys Val Phe Pro Pro Asn Leu Glu Lys Pro Thr Leu Ala Ile
            355                 360                 365
Ile Gly Leu Ile Gln Pro Leu Gly Ala Ile Met Pro Ile Ser Glu Leu
        370                 375                 380
Gln Ala Arg Trp Ala Thr Leu Val Phe Lys Gly Leu Lys Thr Leu Pro
385                 390                 395                 400
Ser Gln Ser Glu Met Met Thr Glu Ile Ser Gln Val Gln Glu Lys Met
                405                 410                 415
Ala Lys Arg Tyr Val Glu Ser Gln Arg His Thr Ile Gly Asp Tyr
            420                 425                 430
Ile Glu Thr Met Glu Glu Ile Ala Asp Leu Val Gly Val Arg Pro Asn
            435                 440                 445
Leu Leu Ser Leu Ala Phe Thr Asp Pro Arg Leu Ala Leu Gln Leu Leu
        450                 455                 460
Leu Gly Pro Cys Thr Pro Val His Tyr Arg Leu Gln Gly Arg Gly Lys
465                 470                 475                 480
Trp Asp Gly Ala Arg Lys Thr Ile Leu Thr Val Glu Asp Arg Ile Arg
                485                 490                 495
Lys Pro Leu Met Thr Arg Val Thr Glu Ser Ser Asn Ser Val Thr Ser
            500                 505                 510
Met Met Thr Met Gly Lys Phe Met Leu Ala Ile Ala Phe Leu Ala Ile
            515                 520                 525
Ala Val Val Tyr Phe
        530

<210> SEQ ID NO 43
<211> LENGTH: 445
<212> TYPE: PRT
<213> ORGANISM: Artificial Sequence
<220> FEATURE:
<223> OTHER INFORMATION: Unknown organism
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
```

```
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (141)..(141)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid
<220> FEATURE:
<221> NAME/KEY: misc_feature
<222> LOCATION: (158)..(158)
<223> OTHER INFORMATION: Xaa can be any naturally occurring amino acid
<220> FEATURE:
<221> NAME/KEY: misc_feature
<222> LOCATION: (211)..(211)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (330)..(330)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid
<220> FEATURE:
<221> NAME/KEY: misc_feature
<222> LOCATION: (387)..(387)
<223> OTHER INFORMATION: Xaa can be any naturally occurring amino acid
<220> FEATURE:
<221> NAME/KEY: misc_feature
<222> LOCATION: (394)..(394)
<223> OTHER INFORMATION: Xaa can be any naturally occurring amino acid
<220> FEATURE:
<221> NAME/KEY: misc_feature
<222> LOCATION: (417)..(417)
<223> OTHER INFORMATION: Xaa can be any naturally occurring amino acid
<220> FEATURE:
<221> NAME/KEY: misc_feature
<222> LOCATION: (444)..(444)
<223> OTHER INFORMATION: Xaa can be any naturally occurring amino acid
<220> FEATURE:
<221> NAME/KEY: misc_feature
<222> LOCATION: (445)..(445)
<223> OTHER INFORMATION: Xaa can be any naturally occurring amino acid

<400> SEQUENCE: 43

Met Ala Pro Xaa Ile Xaa Leu Xaa Thr Ser Arg Xaa Val Ala Val Ile
1               5                   10                  15

Gly Ala Gly Ala Ala Gly Leu Val Ala Ala Arg Glu Leu Arg Arg Glu
```

```
                    20                  25                  30
Gly His Lys Val Val Phe Glu Arg Glu Asn Gln Val Gly Gly Thr
        35                  40                  45
Trp Val Tyr Thr Pro Glu Val Glu Ser Asp Pro Leu Gly Leu Asp Pro
50                  55                  60
Asn Arg Thr Ile Val His Ser Ser Leu Tyr Xaa Ser Leu Arg Thr Asn
65                  70                  75                  80
Leu Pro Arg Glu Val Met Gly Phe Arg Asp Tyr Pro Phe Val Pro Arg
                    85                  90                  95
Glu Gly Glu Gly Arg Asp Pro Arg Arg Phe Pro Xaa His Arg Glu Val
                    100                 105                 110
Leu Xaa Tyr Leu Glu Asp Phe Ala Arg Glu Phe Gly Ile Glu Glu Leu
        115                 120                 125
Val Arg Phe Gly Thr Glu Val Val Phe Xaa Gly Leu Xaa Asp Gly Lys
        130                 135                 140
Trp Arg Val Lys Ser Arg Ser Glu Asp Gly Asp Xaa Val Xaa Glu Ile
145                 150                 155                 160
Phe Asp Ala Val Val Cys Asn Gly His Tyr Thr Glu Pro Arg Val
                165                 170                 175
Ala Glu Ile Pro Gly Ile Asp Ala Trp Pro Gly Lys Gln Met His Ser
                180                 185                 190
His Asn Tyr Arg Thr Pro Glu Pro Phe Arg Asp Gln Val Val Val Leu
                195                 200                 205
Ile Gly Xaa Ser Ala Ser Ala Val Asp Ile Ser Arg Xaa Ile Ala Gly
        210                 215                 220
Val Ala Lys Glu Val His Ile Ala Ser Arg Ser Val Glu Ala Glu Thr
225                 230                 235                 240
Leu Glu Lys Leu Xaa Gly Xaa Asp Asn Met Trp Leu His Ser Met Ile
                245                 250                 255
Glu Ser Val His Lys Asp Gly Thr Val Val Phe Gln Asp Gly Ser Val
                260                 265                 270
Val Leu Ala Asp Val Ile Leu His Cys Thr Gly Tyr Lys Tyr His Phe
                275                 280                 285
Pro Phe Leu Glu Thr Asn Gly Ile Val Thr Val Asp Asp Asn Arg Val
                290                 295                 300
Gly Pro Leu Tyr Lys His Val Phe Pro Ala Leu Ala Pro Gly Leu
305                 310                 315                 320
Ser Phe Val Gly Leu Pro Trp Lys Val Xaa Pro Phe Pro Leu Phe Glu
                325                 330                 335
Leu Gln Ser Lys Trp Ile Ala Gly Val Leu Ser Gly Arg Ile Ala Leu
                340                 345                 350
Pro Ser Xaa Glu Glu Met Met Ala Asp Val Lys Ala Phe Tyr Ser Ser
        355                 360                 365
Leu Glu Ala Ser Gly Lys Pro Lys His Tyr Thr His Asn Leu Gly Asp
        370                 375                 380
Ser Gln Xaa Tyr Asp Asn Trp Leu Ala Xaa Gln Cys Gly Cys Pro Pro
385                 390                 395                 400
Val Glu Glu Trp Arg Lys Gln Met Tyr Ile Ala Thr Ser Lys Asn Lys
                405                 410                 415
Xaa Ala Arg Pro Glu Thr Tyr Arg Asp Glu Trp Asp Asp Asp Leu
        420                 425                 430
Ile Leu Glx Ala Tyr Glu Asp Phe Ala Lys Tyr Xaa Xaa
        435                 440                 445
```

```
<210> SEQ ID NO 44
<211> LENGTH: 1397
<212> TYPE: DNA
<213> ORGANISM: Artificial Sequence
<220> FEATURE:
<223> OTHER INFORMATION: Unknown organism

<400> SEQUENCE: 44
atcatcacac aaaaaagatg gcaccagcac gaacccgagt caactcactc aacgtggcag      60
tgatcggagc cggagccgcc ggactcgtag ctgcaagaga gctccgccgc gagaatcaca     120
ccgtcgtcgt tttcgaacgt gactcaaaag tcggaggtct ctgggtatac acacctaaca     180
gcgaaccaga cccgcttagc ctcgatccaa accgaaccat cgtccattca agcgtctatg     240
attctctccg aaccaatctc ccacgagagt gcatgggtta cagagacttc cccttcgtgc     300
ctcgacctga agatgacgaa tcaagagact cgagaaggta ccctagtcac agagaagttc     360
ttgcttacct tgaagacttc gctagagaat tcaaacttgt ggagatggtt cgatttaaga     420
ccgaagtagt tcttgtcgag cctgaagata agaaatggag ggttcaatcc aaaaattcag     480
atgggatctc caaagatgag atctttgatg ctgttgttgt ttgtaatgga cattatacag     540
aacctagagt tgctcatgtt cctggtatag attcatggcc agggaagcag attcatagcc     600
acaattaccg tgttcctgat caattcaaag accaggtggt ggtagtgata ggaaattttg     660
cgagtggagc tgatatcagc agggacataa cgggagtggc taaagaagtc catatcgcgt     720
ctagatcgaa tccatctaag acatactcaa aacttcccgg gtcaaacaat ctatggcttc     780
actctatgat agaaagtgta cacgaagatg ggacgattgt ttttcagaac ggtaaggttg     840
tacaagctga taccattgtg cattgcactg gttacaaata tcacttccca tttctcaaca     900
ccaatggcta tattactgtt gaggataact gtgttggacc gctttacgaa catgtctttc     960
cgcctgcgct tgctcccggg cttttccttca tcggtttacc ctggatgaca ctgcaattct    1020
ttatgtttga gctccaaagc aagtgggtgg ctgcagcttt gtctggccgg gtcacacttc    1080
cttcagaaga gaaaatgatg gaagacgtta ccgcctacta tgcaaagcgt gaggctttcg    1140
ggcaacctaa gagatacaca catcgacttg gtggaggtca ggttgattac cttaattgga    1200
tagcagagca aattggtgca ccgcccggtg aacaatggag atatcaggaa ataaatggcg    1260
gatactacag acttgctaca caatcagaca ctttccgtga taagtgggac gatgatcatc    1320
tcatagttga ggcttatgag gatttcttga gacagaagct gattagtagt cttccttctc    1380
agttattgga atcttga                                                   1397
```